US009101620B2

(12) United States Patent
Yan et al.

(10) Patent No.: US 9,101,620 B2
(45) Date of Patent: Aug. 11, 2015

(54) POLYMORPH OF 3-(SUBSTITUTED DIHYDROISOINDOLINONE-2-YL)-2,6-DIOXOPIPERIDINE, AND PHARMACEUTICAL COMPOSITIONS THEREOF

(75) Inventors: Rong Yan, Nanjing (CN); Hao Yang, Nanjing (CN); Yongxiang Xu, Nanjing (CN)

(73) Assignee: Nanjing Cavendish Bio-Engineering Technology Co., Ltd., Nanjing (CN)

( * ) Notice: Subject to any disclaimer, the term of this patent is extended or adjusted under 35 U.S.C. 154(b) by 36 days.

(21) Appl. No.: 13/501,437

(22) PCT Filed: Nov. 2, 2010

(86) PCT No.: PCT/CN2010/001751
§ 371 (c)(1),
(2), (4) Date: Apr. 11, 2012

(87) PCT Pub. No.: WO2011/050590
PCT Pub. Date: May 5, 2011

(65) Prior Publication Data
US 2012/0203005 A1    Aug. 9, 2012

(30) Foreign Application Priority Data
Nov. 2, 2009    (CN) .......................... 2009 1 0210392

(51) Int. Cl.
*C07D 401/04*    (2006.01)
*A61K 31/445*    (2006.01)
*A61K 31/454*    (2006.01)

(52) U.S. Cl.
CPC ............ *A61K 31/454* (2013.01); *C07D 401/04* (2013.01)

(58) Field of Classification Search
CPC ........................... C07D 401/04; A61K 31/445
USPC .......................................... 514/323; 546/200
See application file for complete search history.

(56) References Cited

U.S. PATENT DOCUMENTS

| 7,465,800 B2 * | 12/2008 | Jaworsky et al. ............. 546/200 |
| 2005/0096351 A1 | 5/2005 | Jaworsky et al. |
| 2006/0069065 A1 | 3/2006 | Zeldis |

FOREIGN PATENT DOCUMENTS

| CN | 1258293 A | 6/2000 |
| CN | 1117089 C | 8/2003 |
| CN | 1658848 A | 8/2005 |
| CN | 1697655 A | 11/2005 |
| CN | 1732001 A | 2/2006 |
| CN | 1735415 A | 2/2006 |
| CN | 1822834 A | 8/2006 |
| CN | 1871003 A | 11/2006 |
| CN | 1886131 A | 12/2006 |
| CN | 1897945 A | 1/2007 |
| CN | 1913896 A | 2/2007 |

(Continued)

OTHER PUBLICATIONS

APS "Scientific consideration . . ." p. 1-11 (2002).*

(Continued)

*Primary Examiner* — Celia Chang
(74) *Attorney, Agent, or Firm* — Christie, Parker & Hale, LLP

(57) ABSTRACT

The present invention provides polymorph of 3-(4-amino-1-oxo-1,3-dihydro-2H-isoindole-2-yl)-piperidine-2,6-dione, and also the preparing methods and pharmaceutical compositions thereof.

6 Claims, 44 Drawing Sheets

(56) References Cited

FOREIGN PATENT DOCUMENTS

| | | |
|---|---|---|
| CN | 1921758 A | 2/2007 |
| CN | 1956718 A | 5/2007 |
| CN | 1968695 A | 5/2007 |
| CN | 1980667 A | 6/2007 |
| CN | 1984657 A | 6/2007 |
| CN | 1326522 C | 7/2007 |
| CN | 101080400 A | 11/2007 |
| CN | 101098694 A | 1/2008 |
| CN | 101102771 A | 1/2008 |
| CN | 101108185 A | 1/2008 |
| CN | 101111234 A | 1/2008 |
| CN | 101124215 A | 2/2008 |
| CN | 101163489 A | 4/2008 |
| CN | 101531653 A | 9/2009 |
| CN | 100579527 C | 1/2010 |
| CN | 100584331 C | 1/2010 |
| CN | 101696205 A | 4/2010 |
| CN | 1981761 B | 10/2011 |
| WO | WO 98/03502 | 1/1998 |
| WO | WO 98/54170 | 12/1998 |
| WO | WO 03/086373 A1 | 10/2003 |
| WO | WO 03/097052 A2 | 11/2003 |
| WO | WO 2004/035064 A1 | 4/2004 |
| WO | WO 2004/037199 A2 | 5/2004 |
| WO | WO 2004/041190 A2 | 5/2004 |
| WO | WO 2004/043377 A2 | 5/2004 |
| WO | WO 2004/043464 A1 | 5/2004 |
| WO | WO 2004/103274 A2 | 12/2004 |
| WO | WO 2005/044178 A2 | 5/2005 |
| WO | WO 2005/044259 A1 | 5/2005 |
| WO | WO 2005/046318 A2 | 5/2005 |
| WO | WO 2005/055929 A2 | 6/2005 |
| WO | WO 2005/065455 A1 | 7/2005 |
| WO | WO 2005/091991 A2 | 10/2005 |
| WO | WO 2005/097125 A2 | 10/2005 |
| WO | WO 2005/105088 A2 | 11/2005 |
| WO | WO 2005/110408 A1 | 11/2005 |
| WO | WO 2005/112928 A1 | 12/2005 |
| WO | WO 2006/028964 A1 | 3/2006 |
| WO | WO 2006/053160 A2 | 5/2006 |
| WO | WO 2006/058008 A1 | 6/2006 |
| WO | WO 2006/060507 A2 | 6/2006 |

OTHER PUBLICATIONS

Kiek-Other "Crystallization" p. 95-147 (2002).*
Bernstein "polymorphism in molecular crystals" p. 430 (2007).*
Berstein "polymorphism in molecular cyrstals" p. 115-118 (2002).*
Byrn et al. "Solid state chemistry of drugs" p. 63 (1999).*
Davidovich et al. "detection of polymorphism . . . " Am. Pharm. Rev. v.7(1) p. 10, 12, 14, 16, 100 (2004).*
Dean "Analytical chemistry handbook" p. 10.24-10.26 (1995).*
Vippagunta et al. "Crystalline solids" Adv. Drug. Delivery Rev. 48, p. 3-26 (2001).*
PCT International Search Report dated Dec. 28, 2010 for International Application No. PCT/CN2010/001751, 7 pages.
Muller, George W. et al.; Amino-Substituted Thalidomide Analogs: Potent Inhibitors of Tnf-α Production; Bioorganic & Medical Chemistry Letters; 1999, vol. 9, 6 pages.
Chinese Patent Abstract for CN 101696205 A, 2 pgs., (2010).
Chinese Patent Abstract for CN 101531653 A, 2 pgs., (2009).
Chinese Patent Abstract for CN 1871003 A, 2 pgs., (2006).

* cited by examiner

POLYMORPH OF 3-(SUBSTITUTED DIHYDROISOINDOLINONE-2-YL)-2,6-DIOXOPIPERIDINE, AND PHARMACEUTICAL COMPOSITIONS THEREOF

CROSS-REFERENCE TO RELATED APPLICATION(S)

This application is a National Phase Patent Application and claims priority to and benefit of International Application Number PCT/CN2010/001751, filed on Nov. 2, 2010, which claims priority to and benefit of Chinese Patent Application Number 200910210392.3, filed on Nov. 2, 2009, the entire disclosure of which are incorporated herein by reference.

FIELD OF THE INVENTION

The present invention is in the field of polymorph of pharmaceutical compounds, and more specifically it relates to polymorph of 3-(4-amino-1-oxo-1,3-dihydro-2H-isoindole-2-yl)-piperidine-2,6-dione, and as well the preparing methods and pharmaceutical compositions thereof.

BACKGROUND OF THE INVENTION

One kind of 3-(substituted dihydroisoindolinone-2-yl)-2,6-dioxopiperidine, in particular 3-(4-amino-1-oxo-1,3-dihydro-2H-isoindole-2-yl)-piperidine-2,6-dione was disclosed in the article "Amino-substituted thalidomide analogs: Potent inhibitors of TNF-α production" (Muller etc., Bioorganic & Medicinal Chemistry Letters, Vol. 9, Issue 11, 7 Jun., 1999: pp 1625-1630) and Chinese Patent ZL97180299.8. In December 2005, 3-(4-amino-1-oxo-1,3-dihydro-2H-isoindole-2-yl)-piperidine-2,6-dione was approved as a kind of immunomodulator with anti-tumor activities, indicated for the treatment of myelodysplastic syndromes and multiple myeloma.

The diseases and syndromes which can be treated by 3-(4-amino-1-oxo-1,3-dihydro-2H-isoindole-2-yl)-piperidine-2,6-dione include, but are not limited to: myeloproliferative disorder, myelodysplasia syndrome, vasculogenesis, cancer, pain, macular degeneration, asbestosis, anaemia, nervous system disease, dyssomnia, dermatosis, pulmonary hypertension, immune deficiency disorder, parasitic diseases, central lesion etc., namely that were described in the following Chinese Patents with the application numbers, which are incorporated herein in their entirety by reference: 97180299.8, 98805614.3, 03825761.0, 03825567.7, 03813733.X, 03816899.5, 200610150484.3, 200380107531.0, 200710103924.4, 200380108093.X, 200380108398.0, 200480043341.1, 200480038171.8, 200480035556.9, 200480020445.0, 200480043535.1, 200480040004.7, 200480041252.3, 200480042208.4, 200580017546.7, 200580016344.0, 200580020628.7, 200580037220.0, 200580047364.4, 200580046371.2, 200580047031.1 etc.

Eight polymorphs of 3-(4-amino-1-oxo-1,3-dihydro-2H-isoindole-2-yl)-piperidine-2,6-dione and the preparation methods thereof were described by the US Celgene Corporation in the Chinese Patent CN 1871003A (publication number). By the methods, 3-4-amino-1-oxo-1,3-dihydro-2H-isoindole-2-yl)-piperidine-2,6-dione was added into water or organic solvent (e.g. hexane, toluene, acetone, acetonitrile, methanol, ethyl acetate) where it is practically insoluble, and then was dissolved by heating. It will crystallize when being cooled or crystal transform when being stirred for long time in slurrying system of solid-liquid diphase.

Because 3-(4-amino-1-oxo-1,3-dihydro-2H-isoindole-2-yl)-piperidine-2,6-dione is practically insoluble in water or organic solvent (e.g. hexane, toluene, acetone, acetonitrile, methanol, ethyl acetate etc.), even in the condition of heating, a large amount (over 100 times) of solvent is needed, which is disadvantageous in industrial production; in addition, with the method described in the Patent CN 1871003A, the appearance, color and luster of the products can not be improved from light yellow to white or off-white; also, it was not taken into consideration that harmful organic solvent sorted in or above class II (e.g. toluene and acetonitrile etc.) should be tried not to use in synthesis of final products to minimize the negative effects of the residual organic solvent in products on human body.

In terms of polymorphs of drug, each polymorph has different chemical and physical characteristics, including melting point, chemical stability, apparent solubility, rate of dissolution, optical and mechanical properties, vapor pressure as well as density. Such characteristics can directly influence the work-up or manufacture of bulk drug and formulation, and also affect the stability, solubility and bioavailability of formulation. Consequently, polymorph of drug is of great importance to quality, safety and efficacy of pharmaceutical preparation. When it comes to 3-(4-amino-1-oxo-1,3-dihydro-2H-isoindole-2-yl)-piperidine-2,6-dione, there are still needs in the art for new polymorphs suitable for industrial production and with excellent physical and chemical properties as well.

SUMMARY OF THE INVENTION

The inventors of this invention have experienced a large amount of researches and unexpectedly found new polymorphs of 3-(4-amino-1-oxo-1,3-dihydro-2H-isoindole-2-yl)-piperidine-2,6-dione to overcome the deficiencies of the prior art, and the new polymorphic forms have excellent physical and chemical properties and good stabilities, which are suitable for industrial production.

A purpose of this invention is to provide new polymorphs of 3-(4-amino-1-oxo-1,3-dihydro-2H-isoindole-2-yl)-piperidine-2,6-dione.

Another purpose of this invention is to provide the synthetic methods of these new polymorphs mentioned above.

The third purpose of this invention is to provide pharmaceutical compositions comprising the mentioned new polymorphs.

BRIEF DESCRIPTION OF THE DRAWINGS

FIG. 3-1 and FIG. 3-2 are respectively DSC diagram and TGA diagram of the Polymorph I of 3-(4-amino-1-oxo-1,3-dihydro-2H-isoindole-2-yl)-piperidine-2,6-dione of this invention.

FIG. 10-1 and FIG. 10-2 are respectively DSC diagram and TGA diagram of the Polymorph I of 3-(4-amino-1-oxo-1,3-dihydro-2H-isoindole-2-yl)-piperidine-2,6-dione of this invention after high humidity for 10 days.

FIG. 12-1 and FIG. 12-2 are respectively DSC diagram and TGA diagram of the Polymorph I of 3-(4-amino-1-oxo-1,3-dihydro-2H-isoindole-2-yl)-piperidine-2,6-dione of this invention after accelerated test at 40° C. for six months.

FIG. 15-1 and FIG. 15-2 are respectively DSC diagram and TGA diagram of the Polymorph II of 3-(4-amino-1-oxo-1,3-dihydro-2H-isoindole-2-yl)-piperidine-2,6-dione of this invention.

FIG. 21-1 and FIG. 21-2 are respectively DSC diagram and TGA diagram of the Polymorph II of 3-(4-amino-1-oxo-1,3-dihydro-2H-isoindole-2-yl)-piperidine-2,6-dione of this invention after high humidity for 10 days.

FIG. 23-1 and FIG. 23-2 are respectively DSC diagram and TGA diagram of the Polymorph II of 3-(4-amino-1-oxo-1,3-dihydro-2H-isoindole-2-yl)-piperidine-2,6-dione of this invention after accelerated test at 40° C. for six months.

FIG. 26-1 and FIG. 26-2 are respectively DSC diagram and TGA diagram of the Polymorph III of 3-(4-amino-1-oxo-1,3-dihydro-2H-isoindole-2-yl)-piperidine-2,6-dione of this invention.

FIG. 32-1 and FIG. 32-2 are respectively DSC diagram and TGA diagram of the Polymorph III of 3-(4-amino-1-oxo-1,3-dihydro-2H-isoindole-2-yl)-piperidine-2,6-dione of this invention after high humidity for 10 days.

FIG. 34-1 and FIG. 34-2 are respectively DSC diagram and TGA diagram of the Polymorph III of 3-(4-amino-1-oxo-1,3-dihydro-2H-isoindole-2-yl)-piperidine-2,6-dione of this invention after accelerated test at 40° C. for six months.

DETAILED DESCRIPTION OF THE INVENTION

More specifically, this invention provides a Polymorph I of 3-(4-amino-1-oxo-1,3-dihydro-2H-isoindole-2-yl)-piperidine-2,6-dione with a half-molecule water and substantially without other solvents.

Figure 1:
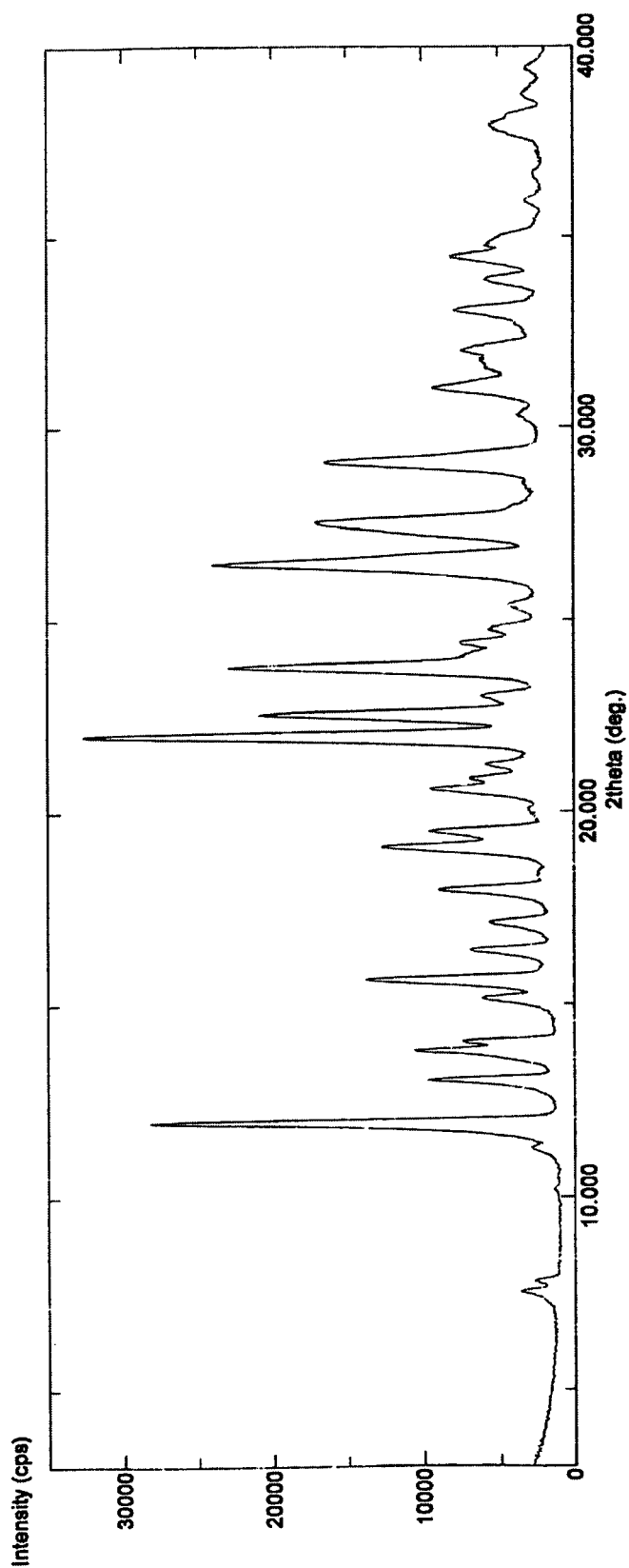
FIG. 1 is an XRPD pattern of the Polymorph I of 3-(4-amino-1-oxo-1,3-dihydro-2H-isoindole-2-yl)-piperidine-2,6-dione of this invention.

The invention provides a Polymorph I of 3-(4-amino-1-oxo-1,3-dihydro-2H-isoindole-2-yl)-piperidine-2,6-dione hemihydrate having the X-ray powder diffraction pattern by using Cu—Ka radiation, characterized by diffraction peaks at 11.9±0.2 and 22.0±0.2 of 2θ indicated with degree, further, one or multiple (in optional combination, including two or more peaks, or all peaks) of diffraction peaks at 15.6±0.2, 22.5±0.2, 23.8±0.2, 26.4±0.2, 27.5±0.2 and 29.1±0.2; as is shown in FIG. 1.

The Polymorph I of 3-(4-amino-1-oxo-1,3-dihydro-2H-isoindole-2-yl)-piperidine-2,6-dione hemihydrate:

| Peak Number | 2θ | Flex Width | d-Value | Intensity | L/LO |
|---|---|---|---|---|---|
| 1 | 11.940 | 0.212 | 7.4060 | 17891 | 84 |
| 2 | 13.020 | 0.235 | 6.7940 | 5996 | 28 |
| 3 | 13.780 | 0.188 | 6.4210 | 6550 | 31 |
| 6 | 15.620 | 0.235 | 5.6685 | 9017 | 42 |
| 9 | 17.960 | 0.259 | 4.9349 | 5895 | 28 |

-continued

| Peak Number | 2θ | Flex Width | d-Value | Intensity | L/LO |
|---|---|---|---|---|---|
| 10 | 19.080 | 0.235 | 4.6476 | 8374 | 39 |
| 11 | 19.480 | 0.235 | 4.5531 | 6273 | 30 |
| 12 | 20.580 | 0.235 | 4.3121 | 6162 | 29 |
| 15 | 21.980 | 0.235 | 4.0405 | 21530 | 100 |
| 16 | 22.520 | 0.259 | 3.9449 | 13747 | 64 |
| 18 | 23.760 | 0.259 | 3.7417 | 15053 | 70 |
| 19 | 24.400 | 0.212 | 3.6450 | 5016 | 24 |
| 21 | 26.440 | 0.282 | 3.3682 | 15819 | 74 |
| 22 | 27.520 | 0.353 | 3.2384 | 11455 | 54 |
| 23 | 29.060 | 0.306 | 3.0702 | 11190 | 52 |
| 24 | 30.980 | 0.306 | 2.8842 | 6238 | 29 |
| 25 | 32.000 | 0.376 | 2.7945 | 4934 | 23 |
| 26 | 33.040 | 0.306 | 2.7089 | 5313 | 25 |
| 28 | 34.440 | 0.259 | 2.6019 | 5469 | 26 |

The Polymorph I of 3-(4-amino-1-oxo-1,3-dihydro-2H-isoindole-2-yl)-piperidine-2,6-dione hemihydrate provided by this invention is characterized in that its DSC (differential scanning calorimetry) has the first endothermic peak between 140° C. and 180° C., more specifically, at about 164.87° C., and the second endothermic peak, namely the maximal endothermic transformation, at about 268.86° C. DSC diagram of the Polymorph I of 3-(4-amino-1-oxo-1,3-dihydro-2H-isoindole-2-yl)-piperidine-2,6-dione hemihydrate of this invention is as in FIG. 3-1, and TGA (Thermal Gravimetric Analysis) diagram is as in FIG. 3-2.

Figure 2:
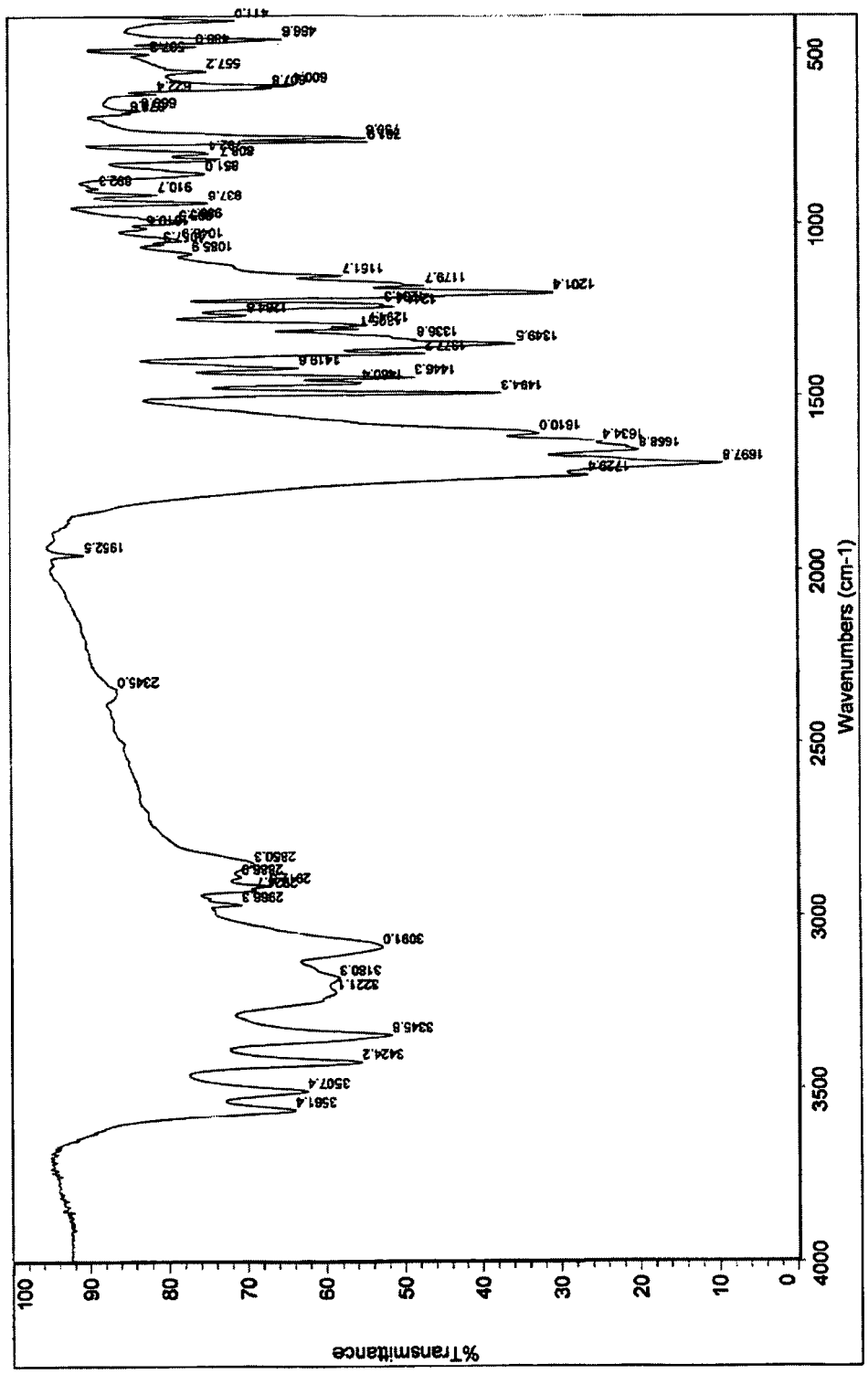
FIG. 2 is an IR diagram of the Polymorph I of 3-(4-amino-1-oxo-1,3-dihydro-2H-isoindole-2-yl)-piperidine-2,6-dione of this invention.
Figures 1, 3:
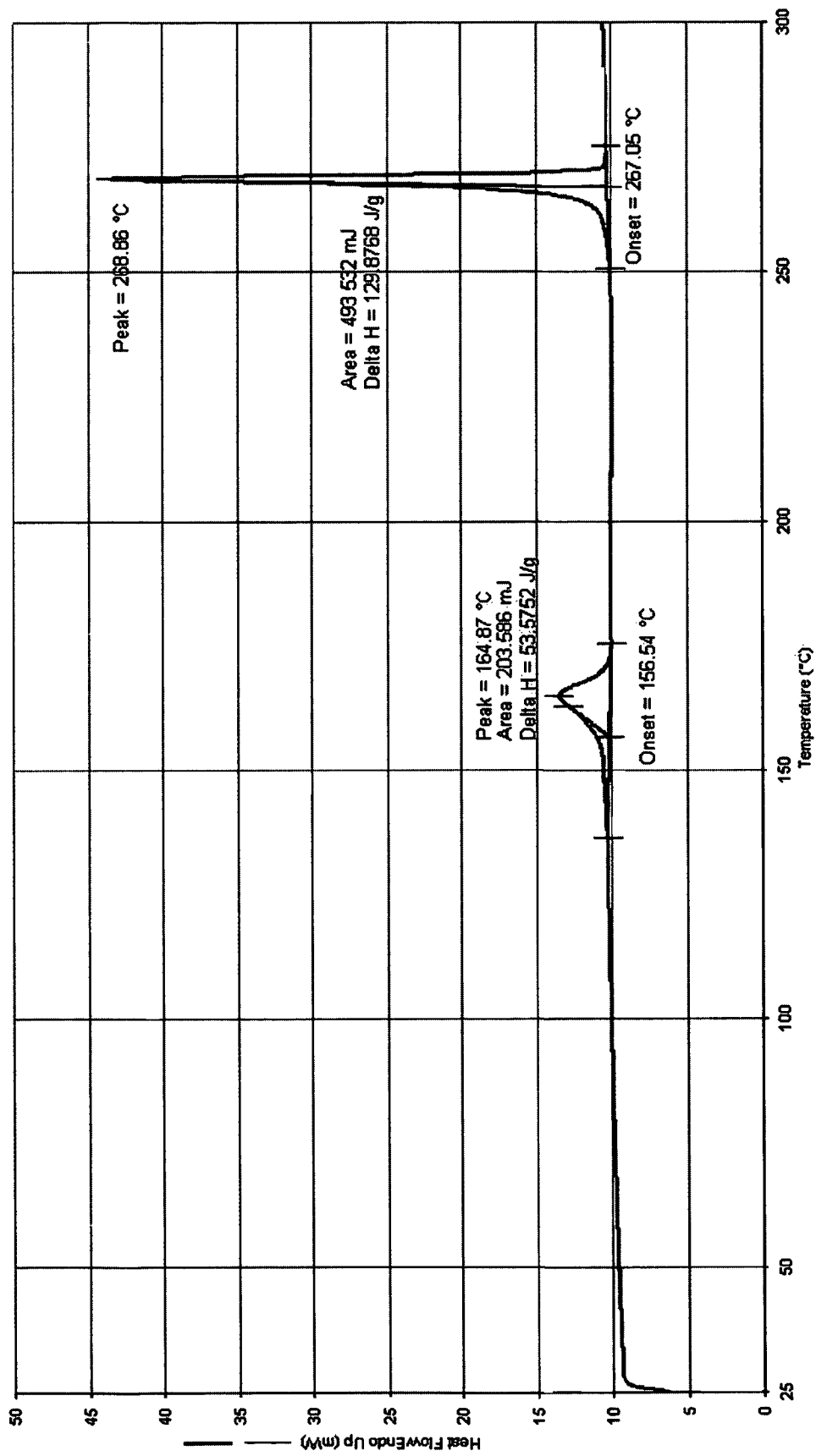
Figures 2, 3:
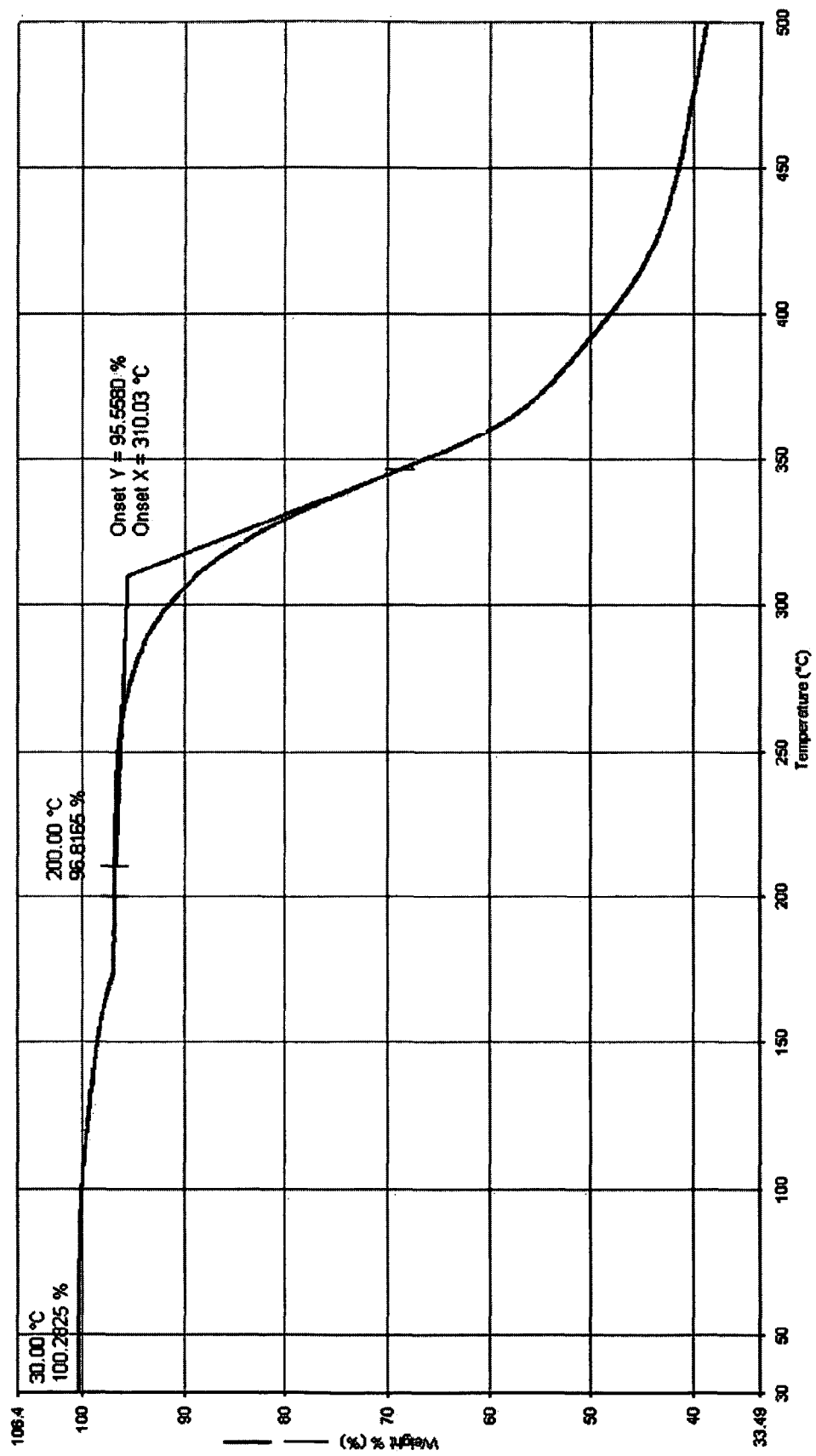

In addition, the Polymorph I of 3-(4-amino-1-oxo-1,3-dihydro-2H-isoindole-2-yl)-piperidine-2,6-dione hemihydrate in this invention has IR (Infrared Spectrum) in KBr disc, which is characterized by absorption peaks at about 3561.4 cm$^{-1}$, 3507.4 cm$^{-1}$, 3424.2 cm$^{-1}$, 3345.8 cm$^{-1}$, 3091.0 cm$^{-1}$, 2912.5 cm$^{-1}$, 1697.8 cm$^{-1}$, 1658.8 cm$^{-1}$, 1610.0 cm$^{-1}$, 1494.3 cm$^{-1}$, 1349.5 cm$^{-1}$, 1201.4 cm$^{-1}$; as in FIG. 2.

Figure 4:
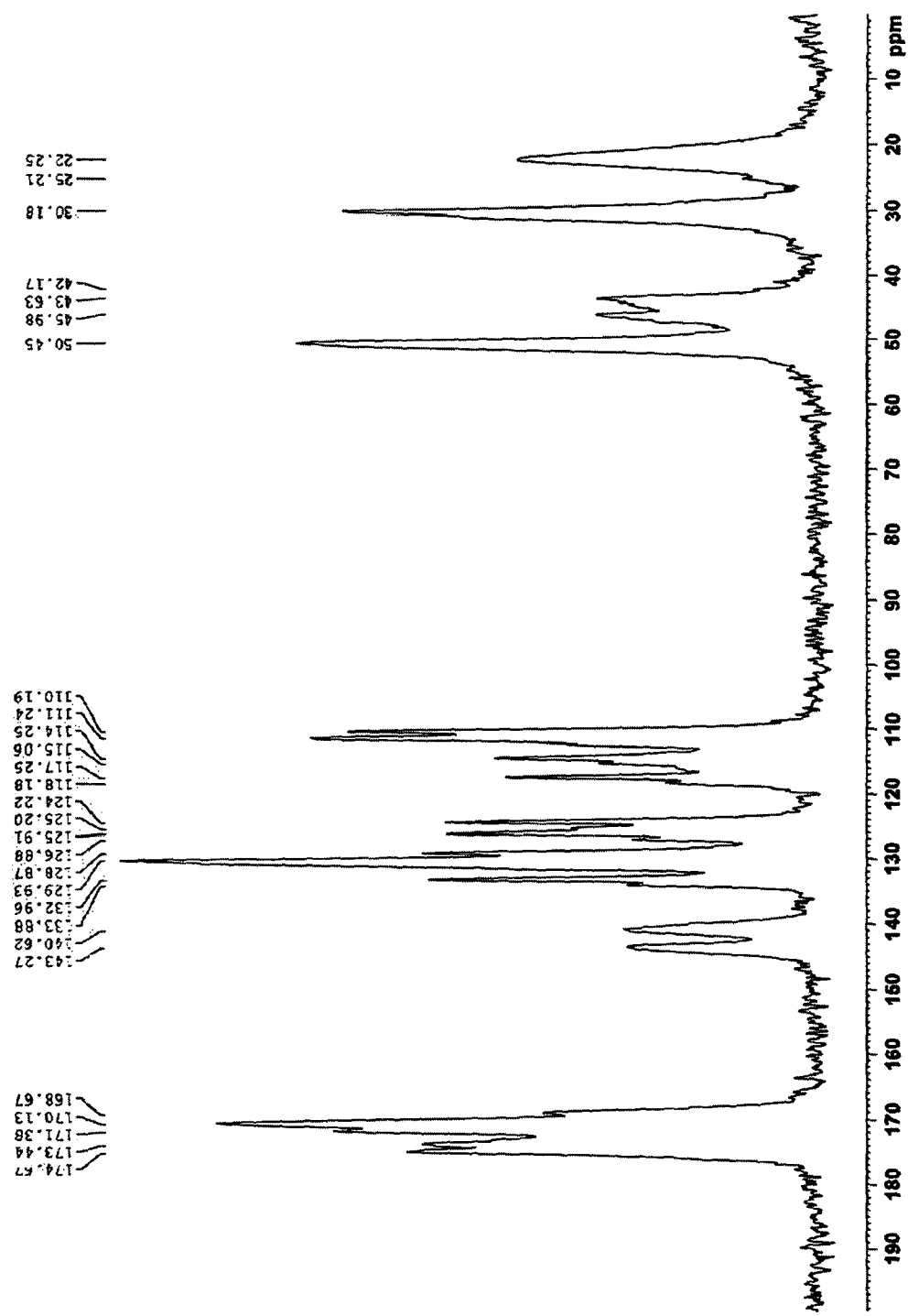
FIG. 4 is a 13C MAS NMR spectrum of the Polymorph I of 3-(4-amino-1-oxo-1,3-dihydro-2H-isoindole-2-yl)-piperidine-2,6-dione of this invention.

The Polymorph I of 3-(4-amino-1-oxo-1,3-dihydro-2H-isoindole-2-yl)-piperidine-2,6-dione hemihydrate in this invention has characteristic chemical shifts δ(ppm) in $^{13}$C solid-state NMR spectrum: 22.25 ppm, 30.18 ppm, 43.63 ppm, 45.98 ppm, 50.45 ppm, 110.19 ppm, 111.24 ppm, 114.25 ppm, 115.06 ppm, 117.25 ppm, 118.18 ppm, 124.22 ppm, 125.20 ppm, 125.91 ppm, 126.88 ppm, 128.87 ppm, 129.93 ppm, 132.96 ppm, 133.88 ppm, 140.62 ppm, 143.27 ppm, 168.67 ppm, 170.13 ppm, 171.38 ppm, 173.44 ppm, 174.67 ppm; as is shown in FIG. 4.

In one embodiment of the invention, this invention provides a preparing method of the Polymorph I of 3-(4-amino-1-oxo-1,3-dihydro-2H-isoindole-2-yl)-piperidine-2,6-dione hemihydrates, including the following steps:

(1). 3-(4-amino-1-oxo-1,3-dihydro-2H-isoindole-2-yl)-piperidine-2,6-dione is added into dimethylformamide (DMF) or dimethylsulfoxide (DMSO), in which: the volume to weight ratio of DMF to 3-(4-amino-1-oxo-1,3-dihydro-2H-isoindole-2-yl)-piperidine-2,6-dione is generally over 1:1; preferably, the volume to weight ratio is over 2:1; more preferably, the volume to weight ratio is from 3.5:1 to 4:1, whereas the volume to weight ratio of DMSO to 3-(4-amino-1-oxo-1,3-dihydro-2H-isoindole-2-yl)-piperidine-2,6-dione is generally over 1:1; preferably, the volume to weight ratio is over 1.5:1; more preferably, the volume to weight ratio is from 2.5:1 to 3:1; and dissolved by stirring and heating.

(2). purified water or a mixed solvent system of purified water and an organic solvent is added; wherein: the volume ratio of purified water or the mixed solvent system to DMF or DMSO is generally over 1:1; preferably, the volume ratio is over 2:1; more preferably, the volume ratio is over 3:1; wherein, the mentioned organic solvent is one kind of solvent or a mixed solvent of several kinds, to which 3-(4-amino-1-oxo-1,3-dihydro-2H-isoindole-2-yl)-piperidine-2,6-dione is insoluble or slightly soluble; preferably, is selected from the group consisting of acetonitrile, trichloromethane, cyclohexane, 1,2-dichloroethene, dichloromethane, 1,2-dimethoxyethane, dioxane, 2-ethoxyethanol, ethylene glycol, n-hexane, methanol, 2-methoxyethanol, methylbutyl ketone, methylcyclohexane, N-methylpyrrolidone, pyridine, tetralin, tetrahydrofuran, toluene, 1,1,2-trichloroethylene, dimethylbenzene, acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether; more preferably, is selected from one or more mixtures of acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether etc., wherein the mixed solvent system is a dual or multiple mixture system consisting of water and organic solvent, and the weight ratio of water to organic solvent mentioned above is generally over 10%; preferably, this ratio was over 20%; more preferably this ratio was over 30%;

(3). Crystalline solid is precipitated by stirring and cooling down slowly;

(4). recover the solid and dry it under vacuum.

Figure 13:
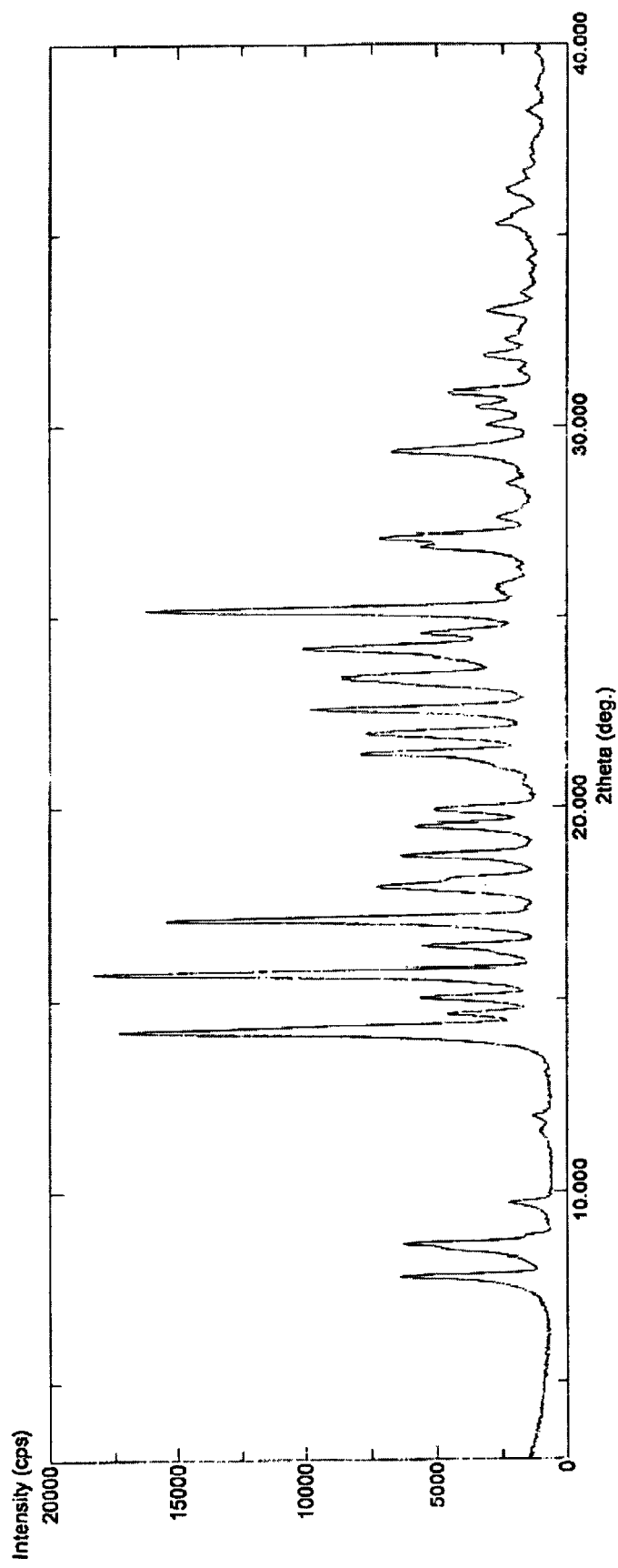
FIG. 13 is an XRPD pattern of the Polymorph II of 3-(4-amino-1-oxo-1,3-dihydro-2H-isoindole-2-yl)-piperidine-2,6-dione of this invention.

In another embodiment, this invention provides a solvated Polymorph II of 3-(4-amino-1-oxo-1,3-dihydro-2H-isoindole-2-yl)-piperidine-2,6-dione having the X-ray powder diffraction pattern by using Cu—Ka radiation, characterized by diffraction peaks at 15.7±0.2 and 25.2±0.2 of 2θ indicated with degree, further, one or multiple (in optional combination, including two or more peaks, or all peaks) of diffraction peaks at 7.8±0.2, 8.6±0.2, 14.2±0.2, 17.1±0.2, 17.9±0.2, 18.8±0.2, 21.4±0.2, 21.9±0.2, 22.6±0.2, 23.4±0.2, 24.2±0.2, 27.1±0.2 and 29.3±0.2; as is shown in FIG. 13

The solvated Polymorph II of 3-(4-amino-1-oxo-1,3-dihydro-2H-isoindole-2-yl)-piperidine-2,6-dione:

| Peak number | 2θ | Flex Width | d-Value | Intensity | L/LO |
|---|---|---|---|---|---|
| 1 | 7.780 | 0.212 | 11.3542 | 3887 | 35 |
| 2 | 8.580 | 0.259 | 10.2972 | 3889 | 35 |
| 4 | 14.180 | 0.259 | 6.2407 | 10819 | 95 |
| 5 | 14.600 | 0.188 | 6.0621 | 2759 | 25 |
| 6 | 15.040 | 0.235 | 5.8857 | 3457 | 31 |
| 7 | 15.680 | 0.212 | 5.6469 | 11410 | 100 |
| 8 | 16.360 | 0.212 | 5.4137 | 3413 | 30 |
| 9 | 17.060 | 0.212 | 5.1931 | 9678 | 85 |
| 10 | 17.920 | 0.259 | 4.9458 | 4770 | 42 |
| 11 | 18.760 | 0.235 | 4.7262 | 4035 | 36 |

-continued

| Peak number | 2θ | Flex Width | d-Value | Intensity | L/LO |
|---|---|---|---|---|---|
| 12 | 19.520 | 0.212 | 4.5439 | 3733 | 33 |
| 13 | 19.920 | 0.235 | 4.4535 | 3350 | 30 |
| 14 | 21.400 | 0.212 | 4.1487 | 5096 | 45 |
| 15 | 21.940 | 0.259 | 4.0478 | 5065 | 45 |
| 16 | 22.580 | 0.235 | 3.9345 | 6307 | 56 |
| 17 | 23.380 | 0.376 | 3.8017 | 5613 | 50 |
| 18 | 24.160 | 0.235 | 3.6807 | 6624 | 59 |
| 19 | 24.540 | 0.235 | 3.6245 | 3649 | 32 |
| 20 | 25.160 | 0.235 | 3.5366 | 10617 | 94 |
| 21 | 26.800 | 0.188 | 3.3238 | 3634 | 32 |
| 22 | 27.060 | 0.188 | 3.2924 | 4818 | 43 |
| 24 | 29.300 | 0.259 | 3.0456 | 4521 | 40 |
| 26 | 30.480 | 0.212 | 2.9304 | 2319 | 21 |
| 27 | 30.860 | 0.235 | 2.8951 | 3105 | 28 |

Figures 1, 15:
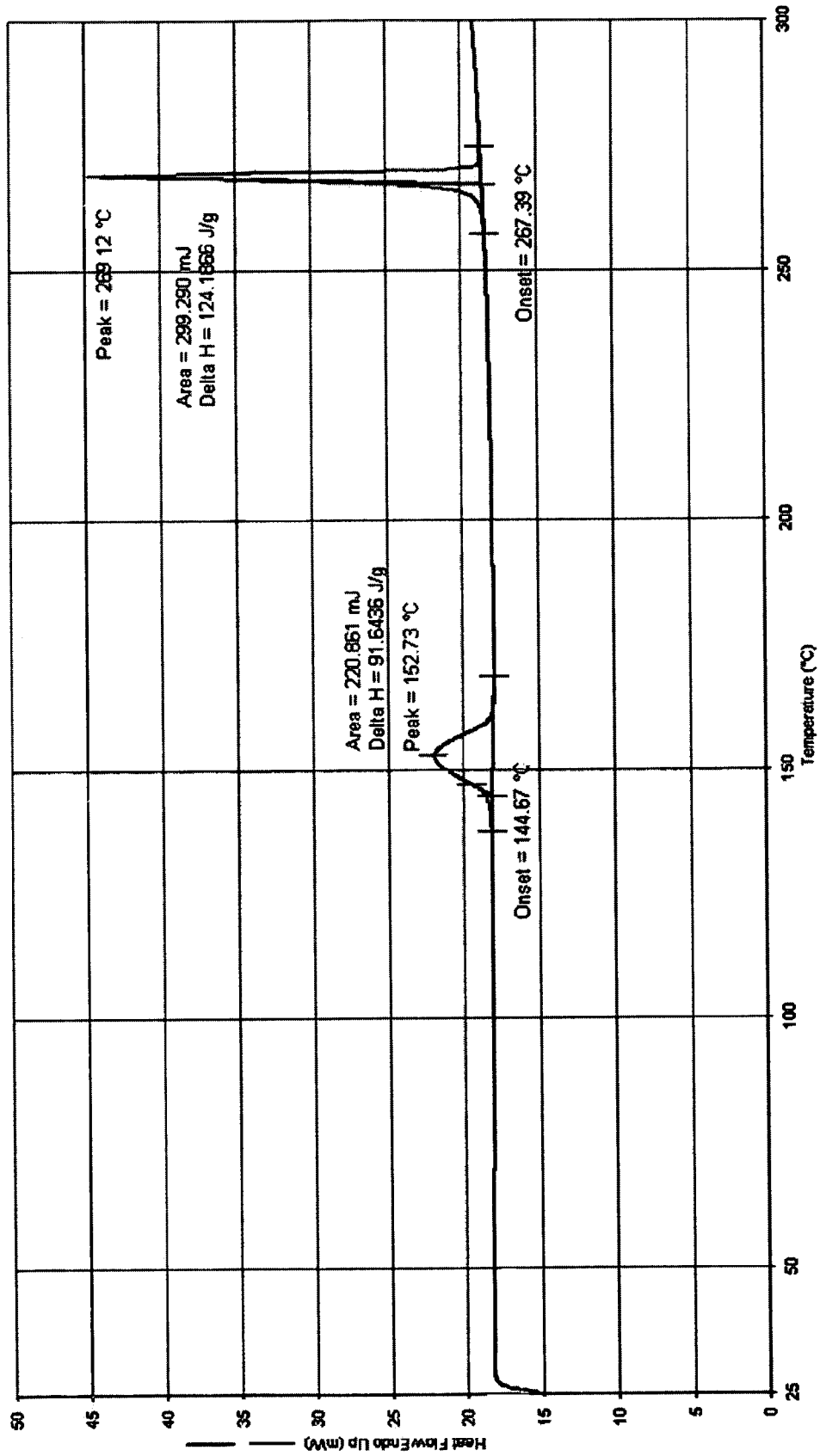
Figures 2, 15:
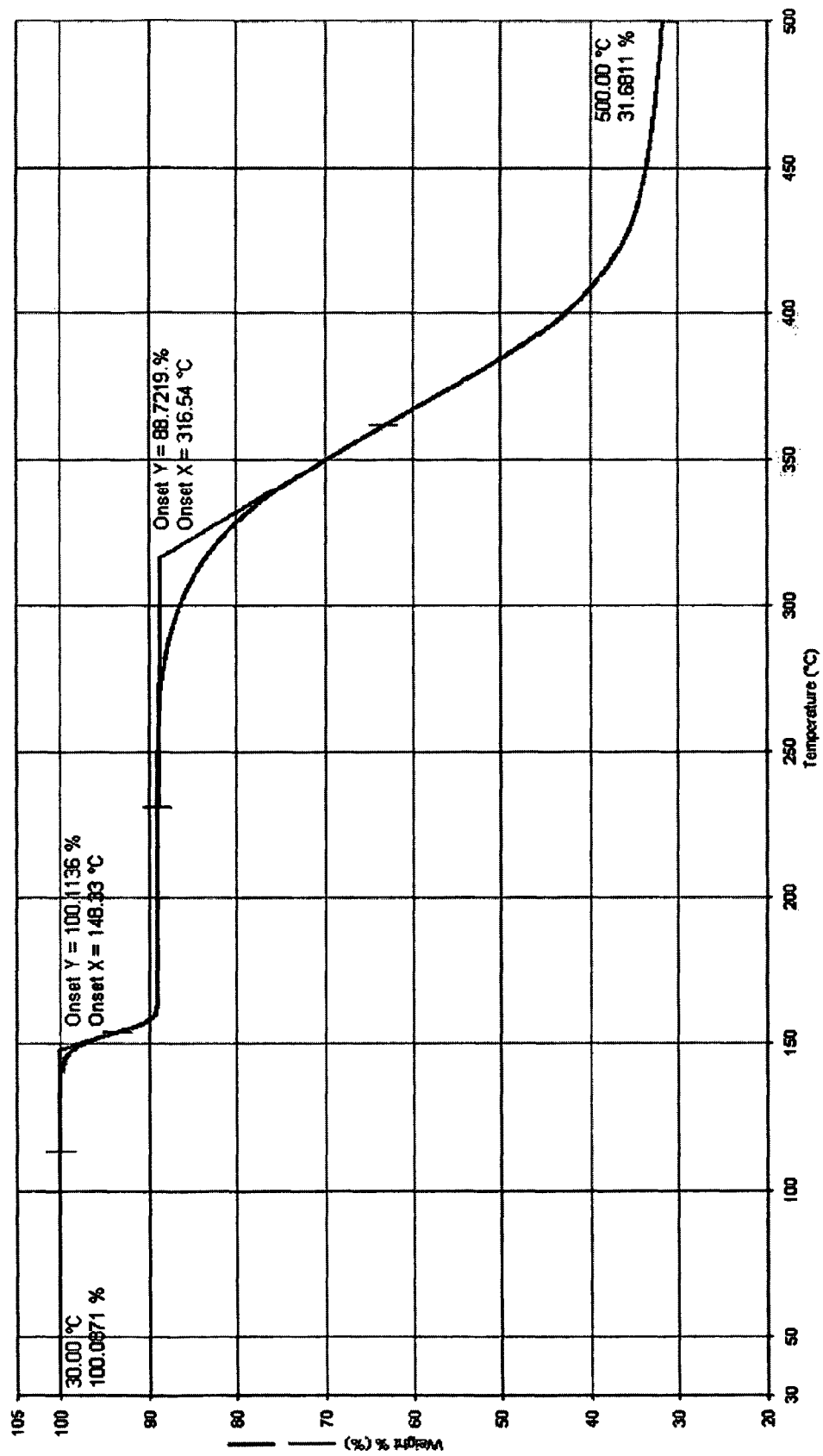

The (acetonitrile) solvated Polymorph II of 3-(4-amino-1-oxo-1,3-dihydro-2H-isoindole-2-yl)-piperidine-2,6-dione provided by this invention is characterized in that its DSC has the first endothermic peak between 140° C. and 170° C., more specifically, at about 152.73° C., and the second endothermic peak, namely the maximal endothermic transformation, at about 269.12° C. DSC diagram of the (acetonitrile) solvated Polymorph II of 3-(4-amino-1-oxo-1,3-dihydro-2H-isoindole-2-yl)-piperidine-2,6-dione of this invention is as in FIG. 15-1, and TGA diagram is as in FIG. 15-2.

Figure 14:
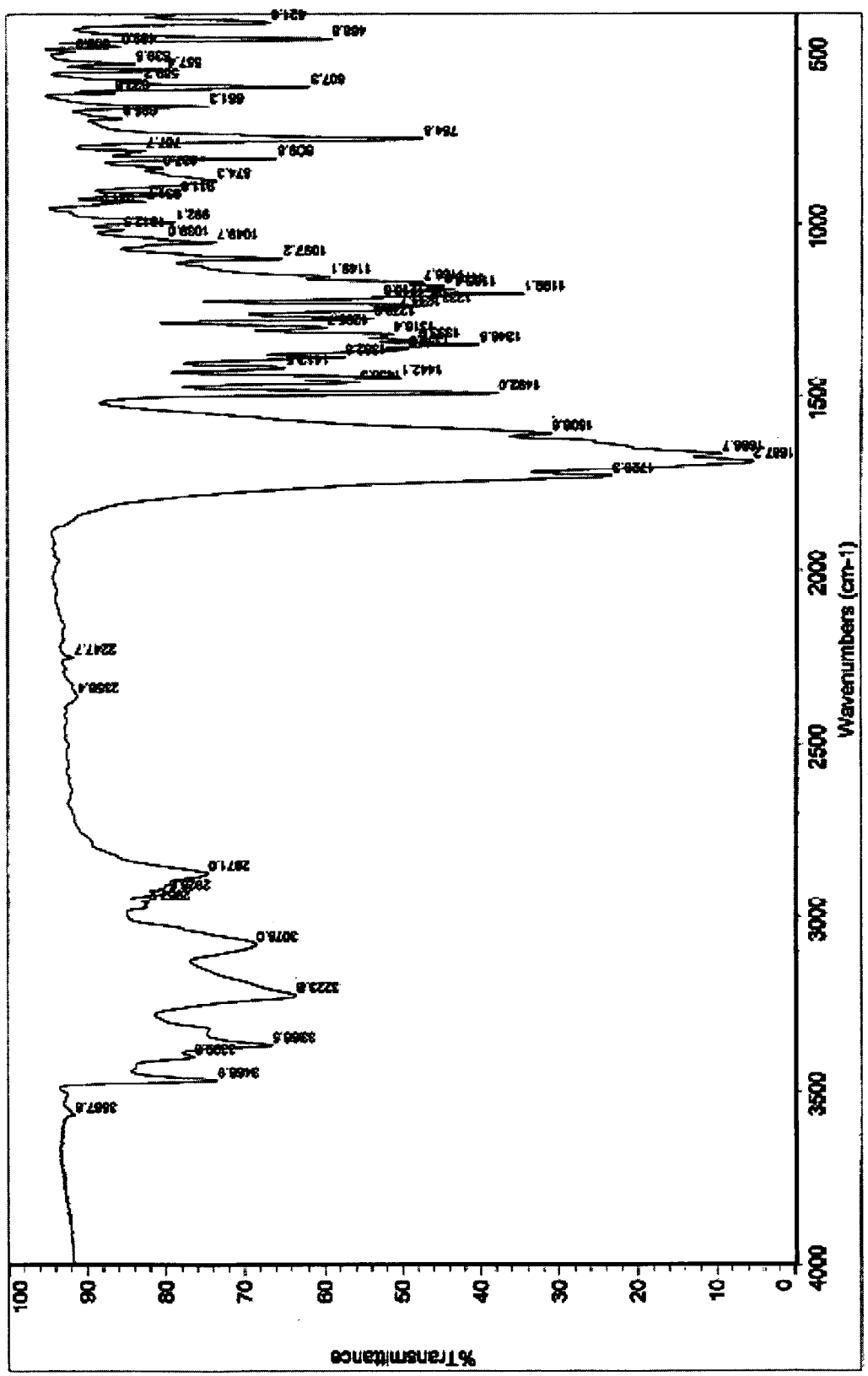
FIG. 14 is an IR diagram of the Polymorph II of 3-(4-amino-1-oxo-1,3-dihydro-2H-isoindole-2-yl)-piperidine-2,6-dione of this invention.

The (acetonitrile) solvated Polymorph II of 3-(4-amino-1-oxo-1,3-dihydro-2H-isoindole-2-yl)-piperidine-2,6-dione provided by this invention has IR in KBr disc, which is characterized by absorption peaks at about 3466.9 $cm^{-1}$, 3366.5 $cm^{-1}$, 3223.8 $cm^{-1}$, 3078.0 $cm^{-1}$, 2957.2 $cm^{-1}$, 2871.0 $cm^{-1}$, 1687.2 $cm^{-1}$, 1666.7 $cm^{-1}$, 1346.5 $cm^{-1}$ and 1199.1 $cm^{-1}$; as in FIG. 14.

In an embodiment, this invention provides preparing method of the (acetonitrile) solvated Polymorph II of 3-(4-amino-1-oxo-1,3-dihydro-2H-isoindole-2-yl)-piperidine-2,6-dione, including the following steps:
(1). 3-(4-amino-1-oxo-1,3-dihydro-2H-isoindole-2-yl)-piperidine-2,6-dione is added into anhydrous dimethylformamide (DMF), in which: the volume to weight ratio of anhydrous DMF to 3-(4-amino-1-oxo-1,3-dihydro-2H-isoindole-2-yl)-piperidine-2,6-dione is generally over 1:1; preferably, the volume to weight ratio is over 2:1; more preferably, the volume to weight ratio is from 3.5:1 to 4:1; and dissolved by stirring and heating;
(2). several times of the volume of an anhydrous organic solvent to DMF is added, wherein, 3-(4-amino-1-oxo-1,3-dihydro-2H-isoindole-2-yl)-piperidine-2,6-dione is insoluble or slightly soluble to the anhydrous organic solvent, and the volume ratio of the organic solvent to DMF is generally over 1:1; preferably, the volume ratio is over 2:1; more preferably, the volume ratio is over 3:1. Here, the mentioned organic solvent is one kind of solvent or a mixed solvent of several kinds; preferably, is selected from the group consisting of acetonitrile, trichloromethane, cyclohexane, 1,2-dichloroethene, dichloromethane, 1,2-dimethoxyethane, dioxane, 2-ethoxyethanol, ethylene glycol, n-hexane, methanol, 2-methoxyethanol, methylbutyl ketone, methylcyclohexane, N-methylpyrrolidone, pyridine, tetralin, tetrahydrofuran, toluene, 1,1,2-trichloroethylene, dimethylbenzene, acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether; more preferably, is selected from one or more mixtures of acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether etc.
(3). crystalline solid is precipitated by stirring and cooling down slowly;
(4). recover the solid and dry it under vacuum.

Figure 24:
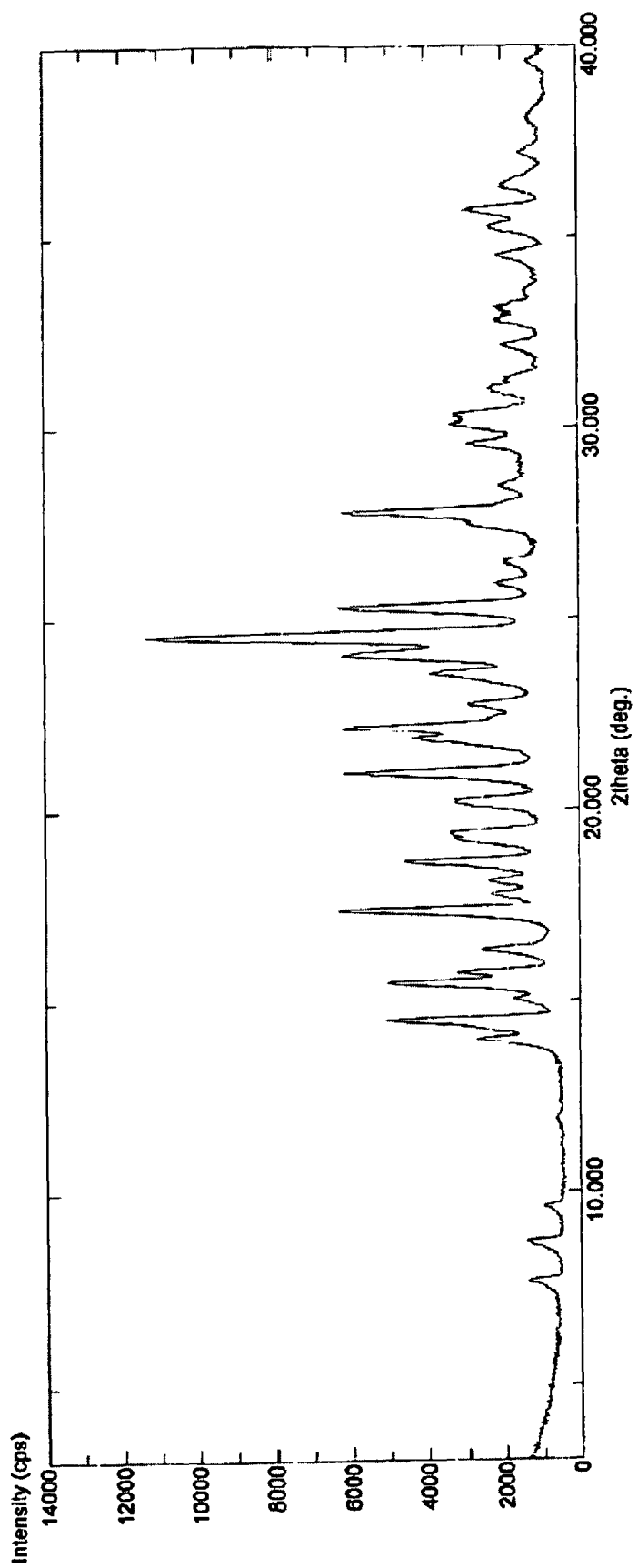
FIG. 24 is an XRPD pattern of the Polymorph III of 3-(4-amino-1-oxo-1,3-dihydro-2H-isoindole-2-yl)-piperidine-2,6-dione of this invention.

In another embodiment, this invention provides a solvated polymorph III of 3-(4-amino-1-oxo-1,3-dihydro-2H-isoindole-2-yl)-piperidine-2,6-dione having X-ray powder diffraction pattern by using Cu—Kα radiation, characterized by diffraction peaks at 17.4±0.2 and 24.5±0.2 of 2θ indicated with degree, further, one or multiple (in optional combination, including two or more peaks, or all peaks) of diffraction peaks at 14.5±0.2, 15.5±0.2, 18.7±0.2, 21.0±0.2, 21.9±0.2, 22.1±0.2, 24.0±0.2, 25.3±0.2 and 27.8±0.2; as is shown in FIG. 24.

The solvated Polymorph III of 3-(4-amino-1-oxo-1,3-dihydro-2H-isoindole-2-yl)-piperidine-2,6-dione:

| Peak number | 2θ | Flex Width | d-Value | Intensity | L/LO |
|---|---|---|---|---|---|
| 1 | 7.660 | 0.165 | 11.5318 | 911 | 12 |
| 2 | 8.700 | 0.212 | 10.1555 | 970 | 13 |
| 3 | 13.980 | 0.212 | 6.3295 | 1777 | 24 |
| 4 | 14.480 | 0.212 | 6.1121 | 3334 | 44 |
| 6 | 15.440 | 0.212 | 5.7342 | 3384 | 45 |
| 7 | 15.720 | 0.165 | 5.6326 | 2108 | 28 |
| 8 | 16.300 | 0.212 | 5.4335 | 1679 | 23 |
| 9 | 17.340 | 0.235 | 5.1099 | 4285 | 57 |
| 10 | 17.780 | 0.235 | 4.9844 | 1551 | 21 |
| 11 | 18.140 | 0.212 | 4.8863 | 1585 | 21 |
| 12 | 18.640 | 0.212 | 4.7563 | 3080 | 41 |
| 13 | 19.380 | 0.188 | 4.5764 | 2319 | 31 |
| 14 | 20.200 | 0.329 | 4.3924 | 2199 | 29 |
| 15 | 20.920 | 0.235 | 4.2428 | 4001 | 53 |
| 16 | 21.820 | 0.188 | 4.0698 | 2919 | 39 |
| 17 | 22.120 | 0.188 | 4.0153 | 4094 | 54 |
| 18 | 22.740 | 0.235 | 3.9072 | 1962 | 26 |
| 19 | 23.540 | 0.235 | 3.7762 | 2590 | 35 |
| 20 | 24.020 | 0.282 | 3.7018 | 4122 | 55 |
| 21 | 24.520 | 0.282 | 3.6274 | 7608 | 100 |
| 22 | 25.240 | 0.235 | 3.5256 | 4272 | 57 |
| 23 | 27.760 | 0.235 | 3.2110 | 4234 | 56 |
| 24 | 29.540 | 0.212 | 3.0214 | 1965 | 26 |
| 25 | 30.040 | 0.235 | 2.9723 | 2254 | 30 |
| 26 | 30.300 | 0.212 | 2.9474 | 2162 | 29 |
| 30 | 35.700 | 0.306 | 2.5129 | 2036 | 27 |

Figures 1, 26:
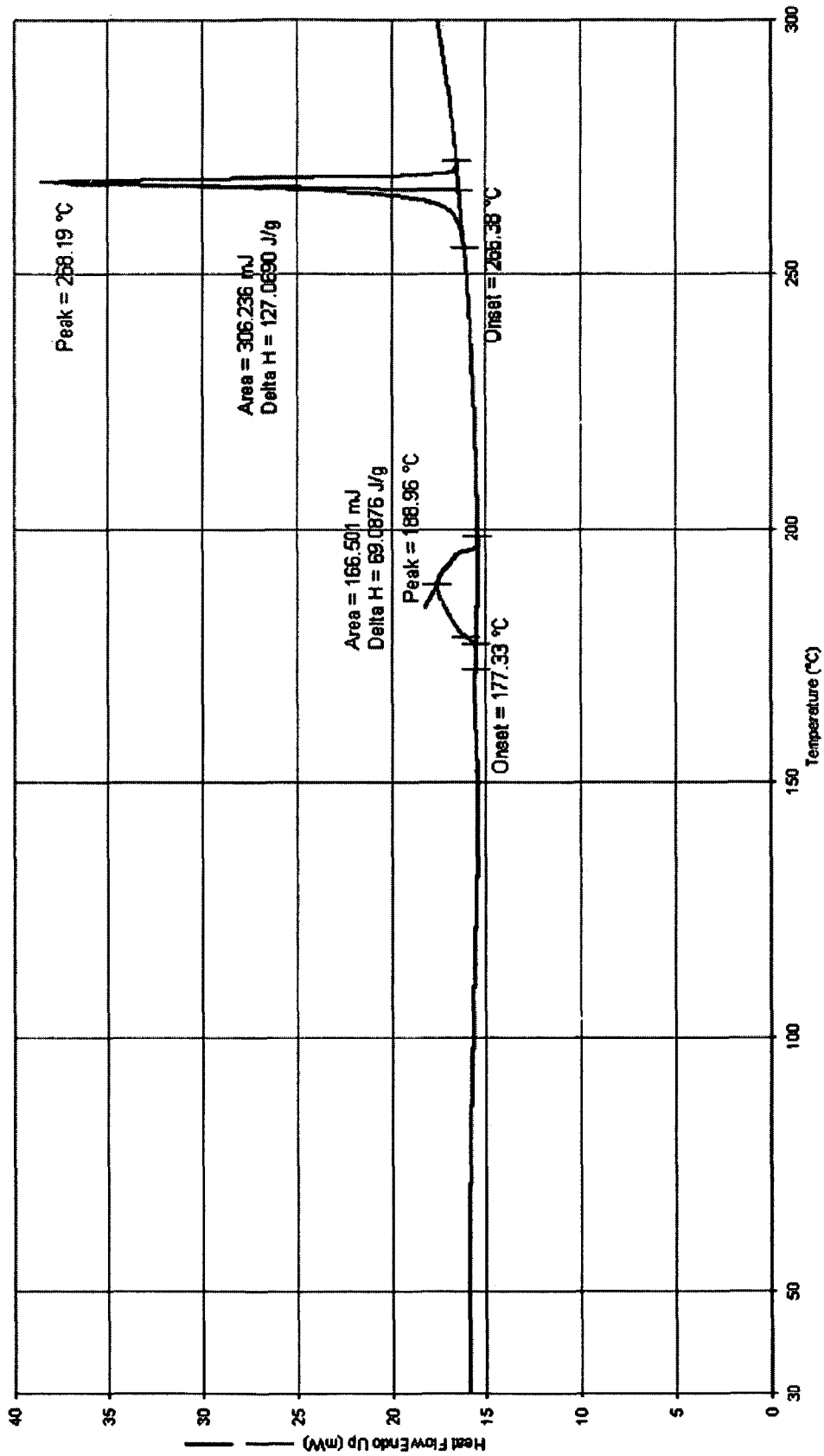
Figures 2, 26:
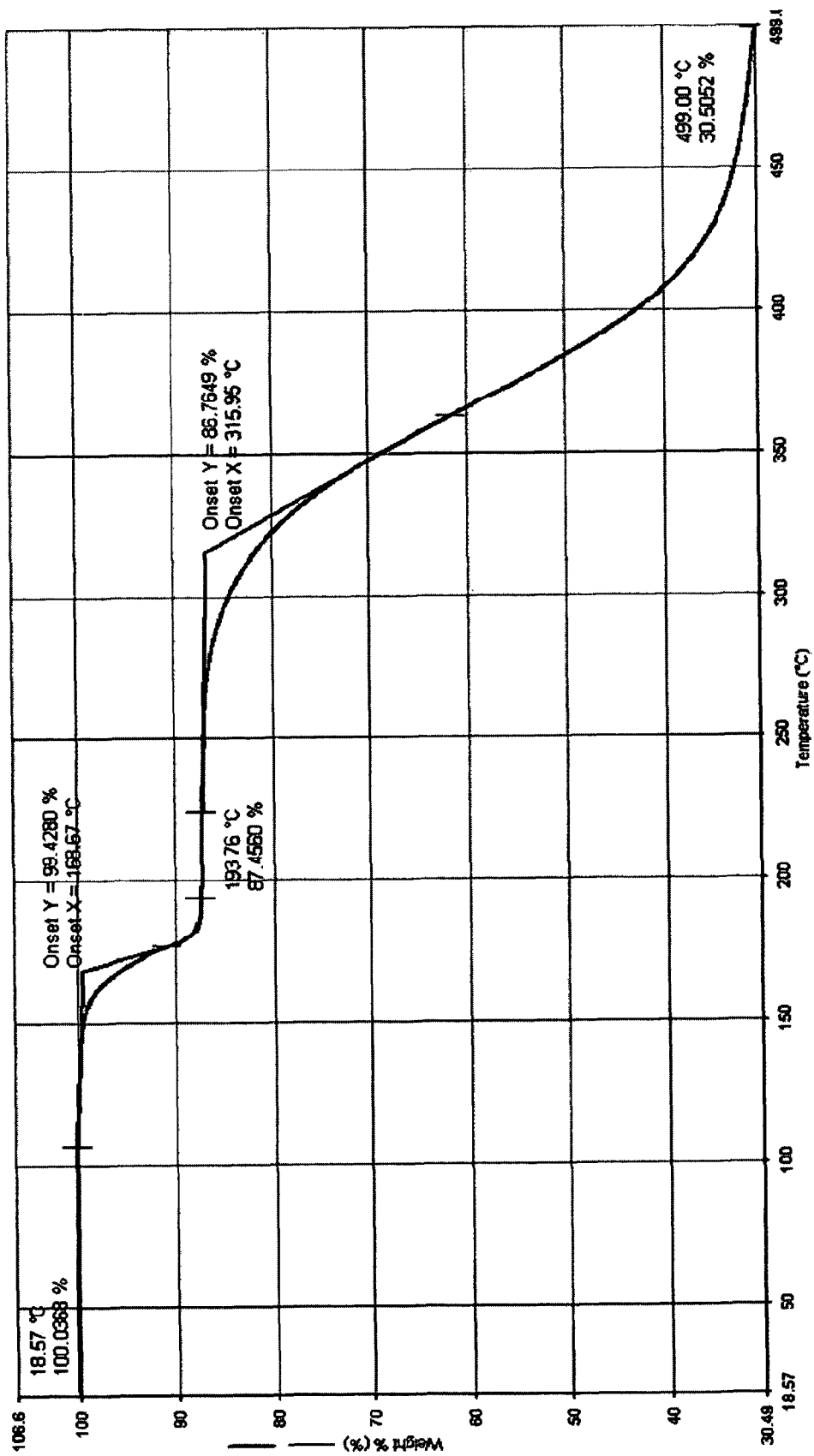

The (acetone) solvated Polymorph III of 3-(4-amino-1-oxo-1,3-dihydro-2H-isoindole-2-yl)-piperidine-2,6-dione provided by this invention is characterized in that its DSC has the first endothermic peak between 150° C. and 200° C., more specifically, at about 188.96° C., and the second endothermic peak, namely the maximal endothermic transform, at about 268.19° C. DSC diagram of the (acetone) solvated Polymorph III of 3-(4-amino-1-oxo-1,3-dihydro-2H-isoindole-2- yl)-piperidine-2,6-dione of this invention is as in FIG. 26-1, and TGA diagram is as in FIG. 26-2.

Figure 25:
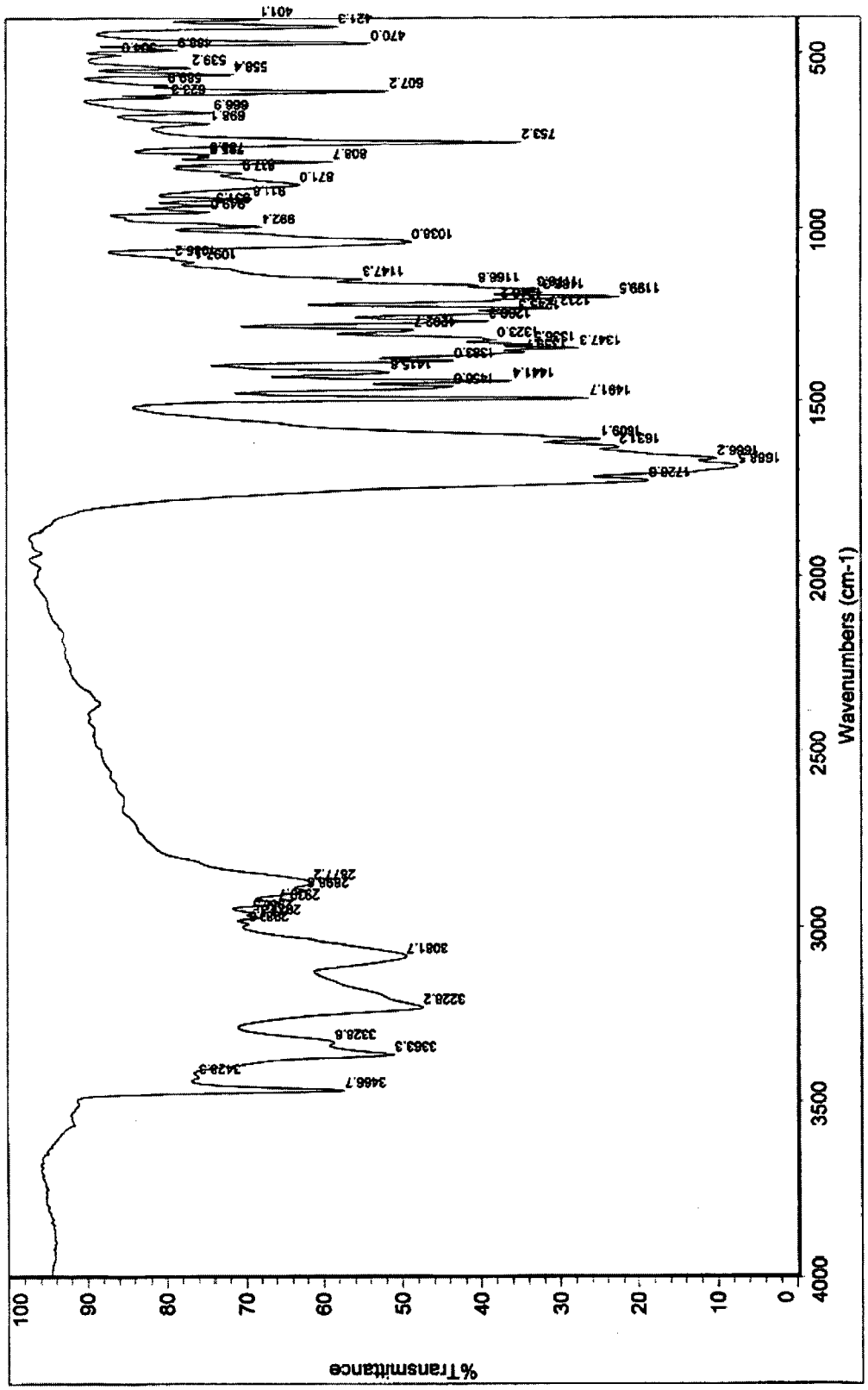
FIG. 25 is an IR diagram of the Polymorph III of 3-(4-amino-1-oxo-1,3-dihydro-2H-isoindole-2-yl)-piperidine-2,6-dione of this invention.

The (acetone) solvated polymorph III of 3-(4-amino-1-oxo-1,3-dihydro-2H-isoindole-2-yl)-piperidine-2,6-dione provided by this invention has IR in KBr disc, which is characterized by absorption peaks at about 3466.7 cm$^{-1}$, 3363.3 cm$^{-1}$, 3228.2 cm$^{-1}$, 3081.7 cm$^{-1}$, 2958.5 cm$^{-1}$, 2877.2 cm$^{-1}$, 1688.5 cm$^{-1}$, 1666.2 cm$^{-1}$, 1609.1 cm$^{-1}$, 1491.7 cm$^{-1}$, 1347.3 cm$^{-1}$ and 1199.5 cm$^{-1}$; as in FIG. 25.

In one embodiment, this invention provided a preparing method of the (acetone) solvated Polymorph III of 3-(4-amino-1-oxo-1,3-dihydro-2H-isoindole-2-yl)-piperidine-2,6-dione, which including the following steps:

(1). 3-(4-amino-1-oxo-1,3-dihydro-2H-isoindole-2-yl)-piperidine-2,6-dione is added into anhydrous dimethylsulfoxide (DMSO), wherein: the volume to weight ratio of anhydrous DMSO to 3-(4-amino-1-oxo-1,3-dihydro-2H-isoindole-2-yl)-piperidine-2,6-dione is generally over 1:1; preferably, the volume to weight ratio is over 2:1; more preferably, the volume to weight ratio is over 3:1; and dissolved by stirring and heating;

(2). several times of the volume of an anhydrous organic solvent to DMSO is added, wherein, 3-(4-amino-1-oxo-1,3-dihydro-2H-isoindole-2-yl)-piperidine-2,6-dione is insoluble or slightly soluble to the anhydrous organic solvent, and the volume ratio of organic solvent to DMSO is generally over 1:1; preferably, the volume ratio is over 2:1; more preferably, the volume ratio is over 3:1. Here, the mentioned organic solvent is one kind of solvent or a mixed solvent of several kinds; preferably, is selected from the group consisting of acetonitrile, trichloromethane, cyclohexane, 1,2-dichloroethene, dichloromethane, 1,2-dimethoxyethane, dioxane, 2-ethoxyethanol, ethylene glycol, n-hexane, methanol, 2-methoxyethanol, methylbutyl ketone, methylcyclohexane, N-methylpyrrolidone, pyridine, tetralin, tetrahydrofuran, toluene, 1,1,2-trichloroethylene, dimethylbenzene, acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum ether; more preferably, is selected from one or more mixtures of acetone, methoxybenzene, n-butanol, 2-butanol, butyl acetate, methyl tertiary-butyl ether, isopropylbenzene, ethanol, ethyl acetate, ethyl ether, ethyl formate, n-heptane, isobutyl acetate, isopropyl acetate, methyl acetate, 3-methyl-1-butanol, butanone, methyl isobutyl ketone, isobutanol, n-pentane, n-pentanol, n-propanol, isopropanol, propyl acetate, 1,1-diethoxypropane, 1,1-dimethoxymethane, 2,2-dimethoxypropane, isooctane, isopropyl ether, methyl isopropyl ketone, methyltetrahydrofuran and petroleum, ether etc.

(3). crystalline solid is precipitated by stirring and cooling down slowly;

(4). recover the solid and dry it under vacuum.

In this invention, the scientific instruments and the test conditions involved in X-ray powder diffraction were: anode target-rotating X-ray diffractometer D/max-2500/PC-type (Japan Rigaku); Cu-target, graphite monochromator, tube voltage of 40 kV, tube current of 100 mA, both divergence slit and antidivergence slit of 1°, receiving slit of 0.3 mm, scanning speed of 5°/min and scanning range of from 3 to 40°.

The scientific instruments and the test conditions involved in DSC in this invention were: US Perkin Elmer Diamond DSC; heating from 25° C. to 300° C. at the rate of 10° C./min.

The scientific instruments and the test conditions involved in TGA in this invention were: US Perkin Elmer Thermal Analysis Pyris 1 TGA; heating from 25° C. to 300° C. at the rate of 10° C./min.

The scientific instruments and the test conditions involved in solid-state NMR in this invention were: instruments: wide-bore solid-state NMR spectrometer AVANCE III 400MH-type (BRUKER); test conditions: CP-MAS; methods: rotating speed of 14000 Hz, scanning times of 1404, relaxation delay of 40 s, contact time of 2 ms, 13 C frequency of 100.6234936 MHz and 1H frequency of 400.1413530 MHz.

The conditions and methods of related substance test involved in this invention were in accordance with HPLC (Appendix VD of Chinese Pharmacopoeia Edition 2005).

Chromatographic conditions and system applicability: octadecylsilane bonded silica as the filler; 0.01 mol/L of potassium dihydrogen phosphate (adjusted to pH 3.5 by phosphoric acid)-methanol-acetonitrile (80:15:5) as the mobile phase; detection wavelength was 240 nm; the number of theoretical plates should be not less than 2000, calculated according to the peak of 3-(4-amino-1-oxo-1,3-dihydro-2H-isoindole-2-yl)-piperidine-2,6-dione. The resolution of the peak of 3-(4-amino-1-oxo-1,3-dihydro-2H-isoindole-2-yl)-piperidine-2,6-dione from the peaks of adjacent impurities should meet requirements.

The test conditions and method of dissolution test were referred to Method 1 in Appendix XC of Chinese Pharmacopoeia Edition 2005.

According to the method of dissolution test, the sample was added into 500 ml (for 5 mg strength) or 1000 ml (for 10 mg or 25 mg of strength) of water as medium, and stirred at 100 rounds per minute, then preceded the procedure in the Method 1. After 45 minutes, a quantity of the solution was filtered, and the first filtrate was discarded and the following filtrate was taken as test solution for study (for 5 mg or 10 mg of strength); 10 ml of the following filtrate was measured accurately to be sample solution for study (for 25 mg of strength). Then a proper quantity of standard 3-(4-amino-1-oxo-1,3-dihydro-2H-isoindole-2-yl)-piperidine-2,6-dione was measured accurately and mixed with water to be the standard solution containing 10 μg 3-(4-amino-1-oxo-1,3-dihydro-2H-isoindole-2-yl)-piperidine-2,6-dione per ml. According to UV-vis spectrophotometry (Appendix IVA of Chinese Pharmacopoeia Edition 2005), absorbency of sample solution and standard solution were determined at 240 nm wavelength and the dissolving-out amount of per pill (or tablet) was calculated by absorbency on the basis of ESTD.

The characteristics of the Polymorph I of 3-(4-amino-1-oxo-1,3-dihydro-2H-isoindole-2-yl)-piperidine-2,6-dione (hemihydrate)

1. Solubility

Test was performed according to the Examples of Chinese Pharmacopoeia Edition 2005. Method: a definite quantity of the Polymorph I of 3-(4-amino-1-oxo-1,3-dihydro-2H-isoindole-2-yl)-piperidine-2,6-dione (hemihydrate) measured accurately was added into a certain quantity of solvent slowly, while the mixture was shaken strongly for 30 seconds every 5 minutes and the dissolving status within 30 minutes was observed. Results were listed in Tab. 1.

TABLE 1 solubility test of the Polymorph I of 3-(4-amino-1-oxo-1,3-dihydro-2H-isoindole-2-yl)-piperidine-2,6-dione (hemihydrate)

| Solvent | Sample quantity (g) | Solvent quantity (ml) | Solute: Solvent | Dissolving status | Conclusion |
|---|---|---|---|---|---|
| water | 0.0113 | 100 | 1:8849.6 | fully dissolved | very slightly soluble |
| 0.1 mol/L NaOH solution | 0.0516 | 5 | 1:97.5 | fully dissolved | sparingly soluble |
| 0.1 mol/L HCl solution | 0.1019 | 100 | 1:981.4 | fully dissolved | slightly soluble |
| ethanol | 0.0109 | 70 | 1:6422.0 | fully dissolved | very slightly soluble |
| acetonitrile | 0.0520 | 50 | 1:961.5 | fully dissolved | slightly soluble |
| ethyl acetate | 0.0111 | 70 | 1:6306.3 | fully dissolved | very slightly soluble |
| methanol | 0.0115 | 10 | 1:869.6 | fully dissolved | slightly soluble |
| acetic acid | 0.1008 | 3 | 1:29.8 | fully dissolved | soluble |
| acetone | 0.0521 | 25 | 1:479.8 | fully dissolved | slightly soluble |
| DMSO | 0.1003 | 1 | 1:9.97 | fully dissolved | freely soluble |
| DMF | 0.1011 | 3 | 1:29.7 | fully dissolved | soluble |

The Polymorph 1 of 3-(4-amino-1-oxo-1,3-dihydro-2H-isoindole-2-yl)-piperidine-2,6-dione (hemihydrate) was: freely soluble in dimethylsulfoxide; soluble in N,N-dimethylformamide and acetic acid; sparingly soluble in 0.1 mol/L NaOH solution; slightly soluble in 0.1 mol/L HCL solution, acetonitrile, methanol and acetone; very slightly soluble in water, ethanol and ethyl acetate.

2. Stability 2.1 Photostability Test

Figure 5:
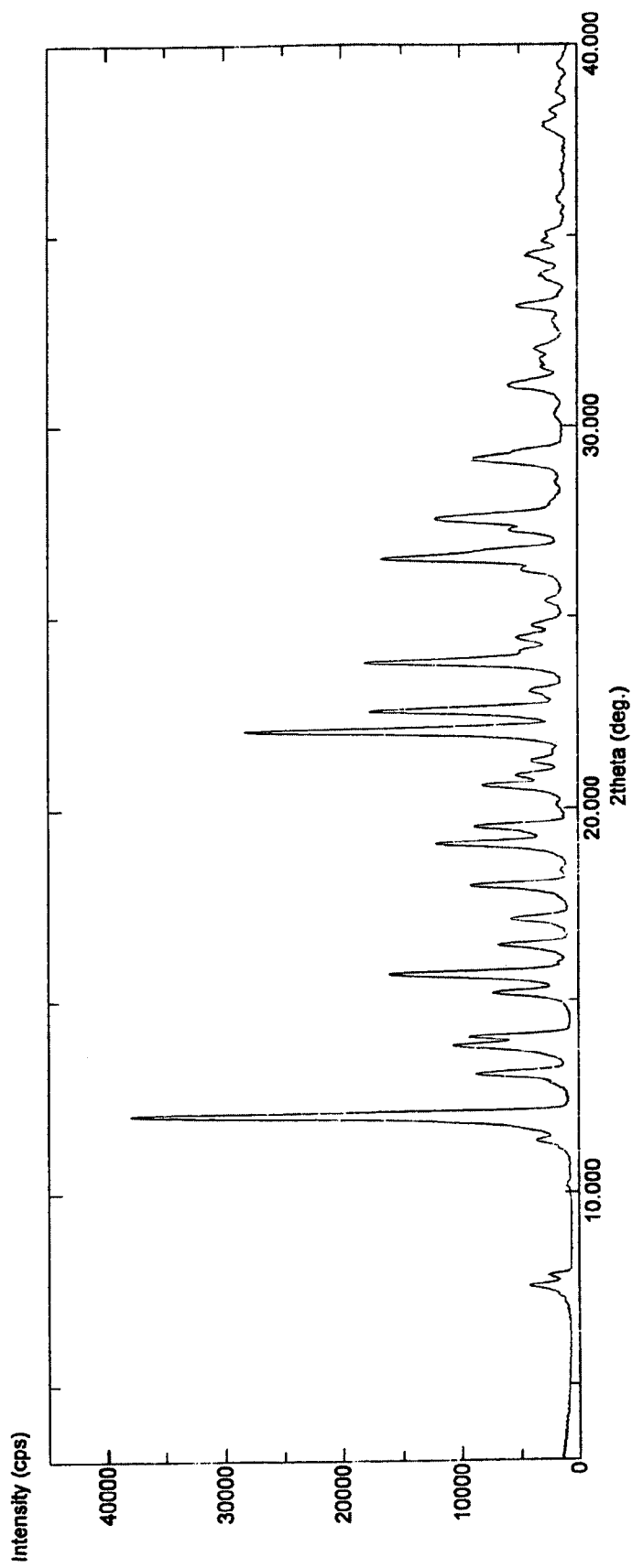
FIG. 5 is an XRPD pattern of the Polymorph I of 3-(4-amino-1-oxo-1,3-dihydro-2H-isoindole-2-yl)-piperidine-2,6-dione of this invention after strong illumination for 10 days.
Figure 6:
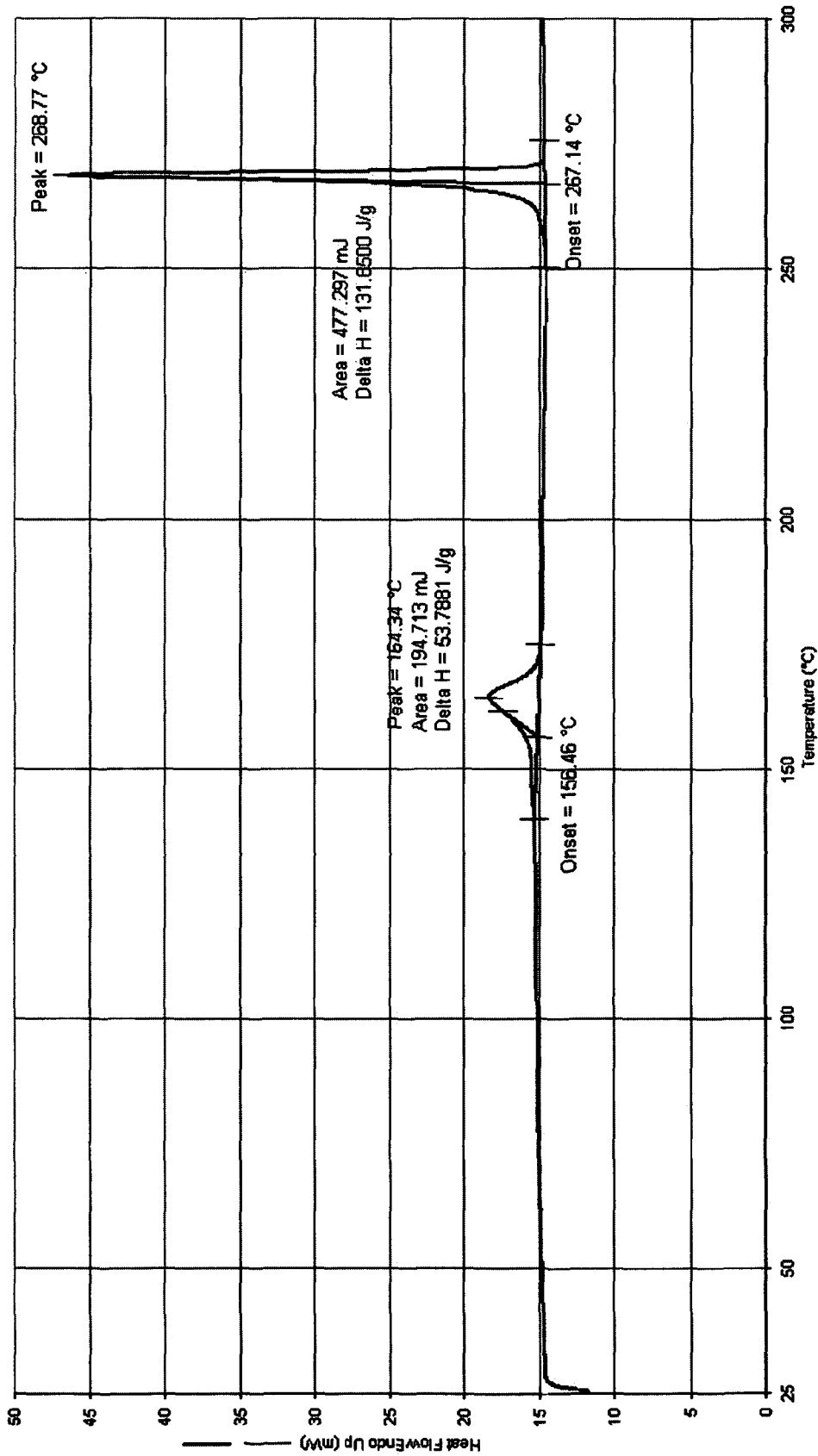
FIG. 6 is a DSC diagram of the Polymorph I of 3-(4-amino-1-oxo-1,3-dihydro-2H-isoindole-2-yl)-piperidine-2,6-dione of this invention after strong illumination for 10 days.

The Polymorph I of 3-(4-amino-1-oxo-1,3-dihydro-2H-isoindole-2-yl)-piperidine-2,6-dione (hemihydrate) was distributed homogeneously in open petri dish with the thickness of the raw material not more than 5 mm, and the distance was adjusted to make illumination intensity at 4500±500 Lx. Sample was tested at the 5$^{th}$ and 10$^{th}$ day respectively and the results were contrasted with that of the Day 0. Results were listed in Tab. 2. After strong illumination for 10 days, the X-ray powder diffraction pattern was shown in FIG. 5; DSC diagram of the Polymorph I of 3-(4-amino-1-oxo-1,3-dihydro-2H-isoindole-2-yl)-piperidine-2,6-dione (hemihydrate) was in FIG. 6.

TABLE 2

Photostability Test (4500 ± 500 lx)

Items

| Time (days) | Appearance | Related substance | Content | Melting point (Decomposition point) |
|---|---|---|---|---|
| 0 | off-white powder | 0.05% | 99.87% | 268.66° C. |
| 5 | off-white powder | 0.05% | 99.85% | / |
| 10 | off-white powder | 0.05% | 99.86% | 267.08° C. |

Note:
the fluctuation of temperature was between 23° C. and 26° C.; relative humidity was between 56% and 63%.

2.2 High Temperature Test

Figure 7:
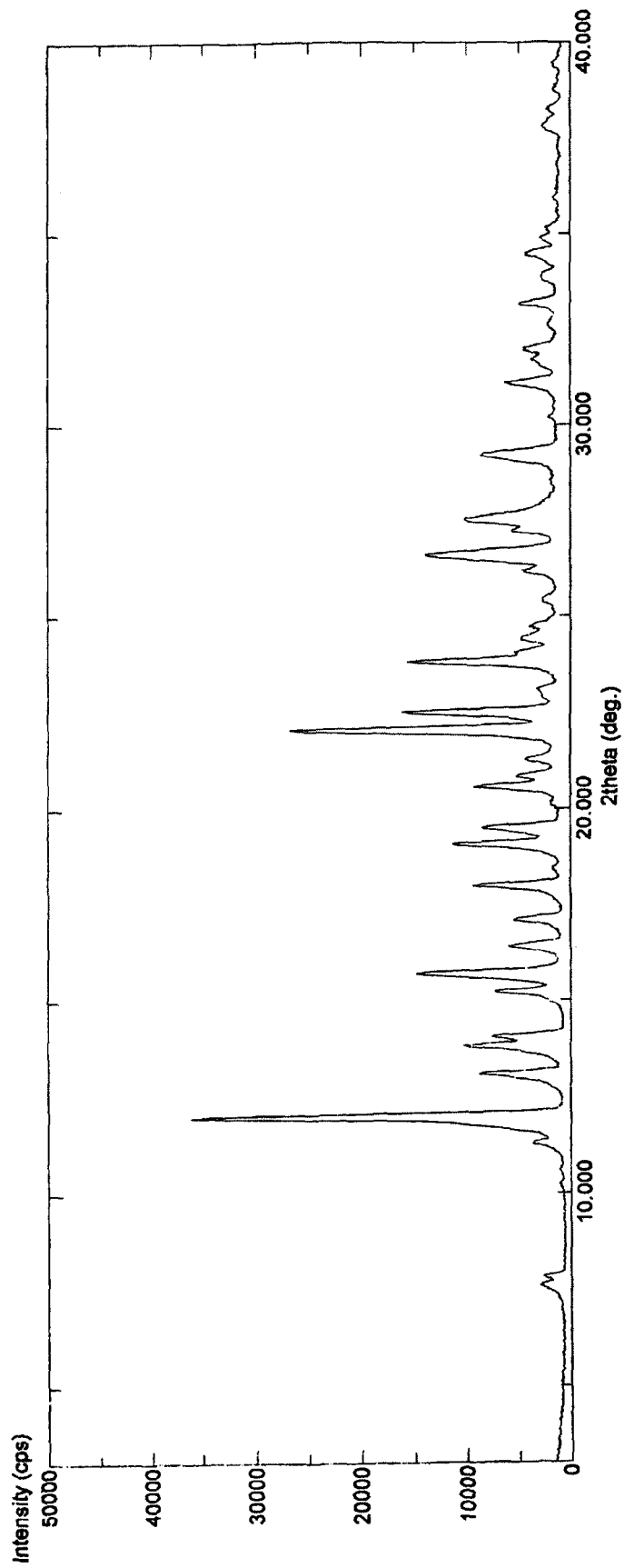
FIG. 7 is an XRPD pattern of the Polymorph I of 3-(4-amino-1-oxo-1,3-dihydro-2H-isoindole-2-yl)-piperidine-2,6-dione of this invention after high temperature test of 60° C. for 10 days.
Figure 8:
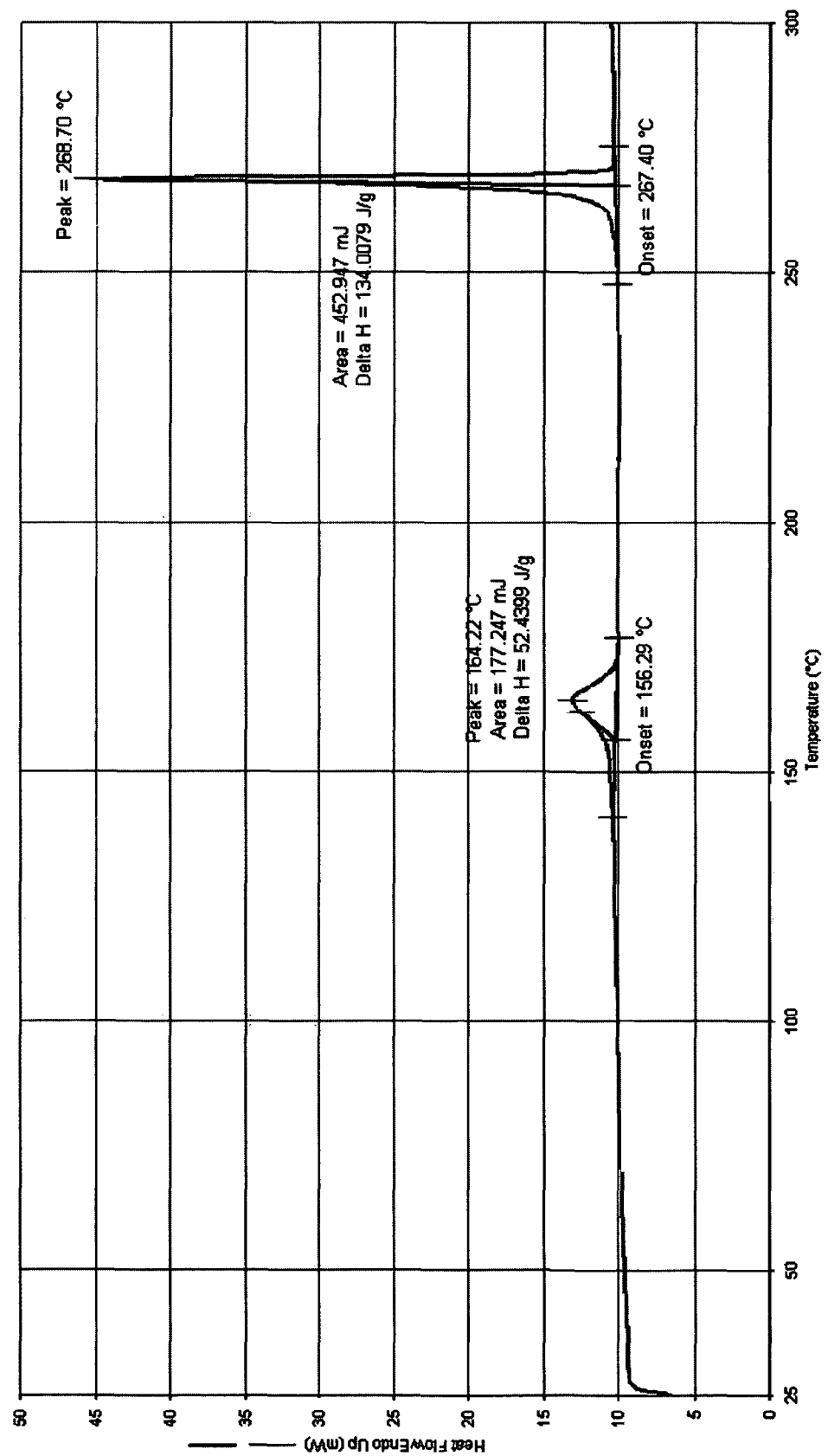
FIG. 8 is a DSC diagram of the Polymorph I of 3-(4-amino-1-oxo-1,3-dihydro-2H-isoindole-2-yl)-piperidine-2,6-dione of this invention after high temperature test of 60° C. for 10 days.

The raw material of Polymorph I of 3-(4-amino-1-oxo-1,3-dihydro-2H-isoindole-2-yl)-piperidine-2,6-dione (hemihydrate) was put into a clean sealed glass bottle and then put in thermostatic drying chamber at 60° C. Sample was tested at the 5$^{th}$ and 10$^{th}$ day respectively and the results were contrasted with that of the Day 0. Results were listed in Tab. 3. After high temperature test of 60° C. for 10 days, the X-ray powder diffraction pattern was shown FIG. 7; DSC diagram was in FIG. 8.

TABLE 3

High Temperature Test (60° C.)

Items

| Time (days) | Appearance | Related substance | Content | Melting point (° C.) |
|---|---|---|---|---|
| 0 | off-white powder | 0.05% | 99.87% | 268.66 |
| 5 | off-white powder | 0.05% | 99.86% | / |
| 10 | off-white powder | 0.06% | 99.84% | 267.32 |

Note:
the variation of relative humidity was between 54% and 62%.

2.3 High Humidity Test

Figure 9:
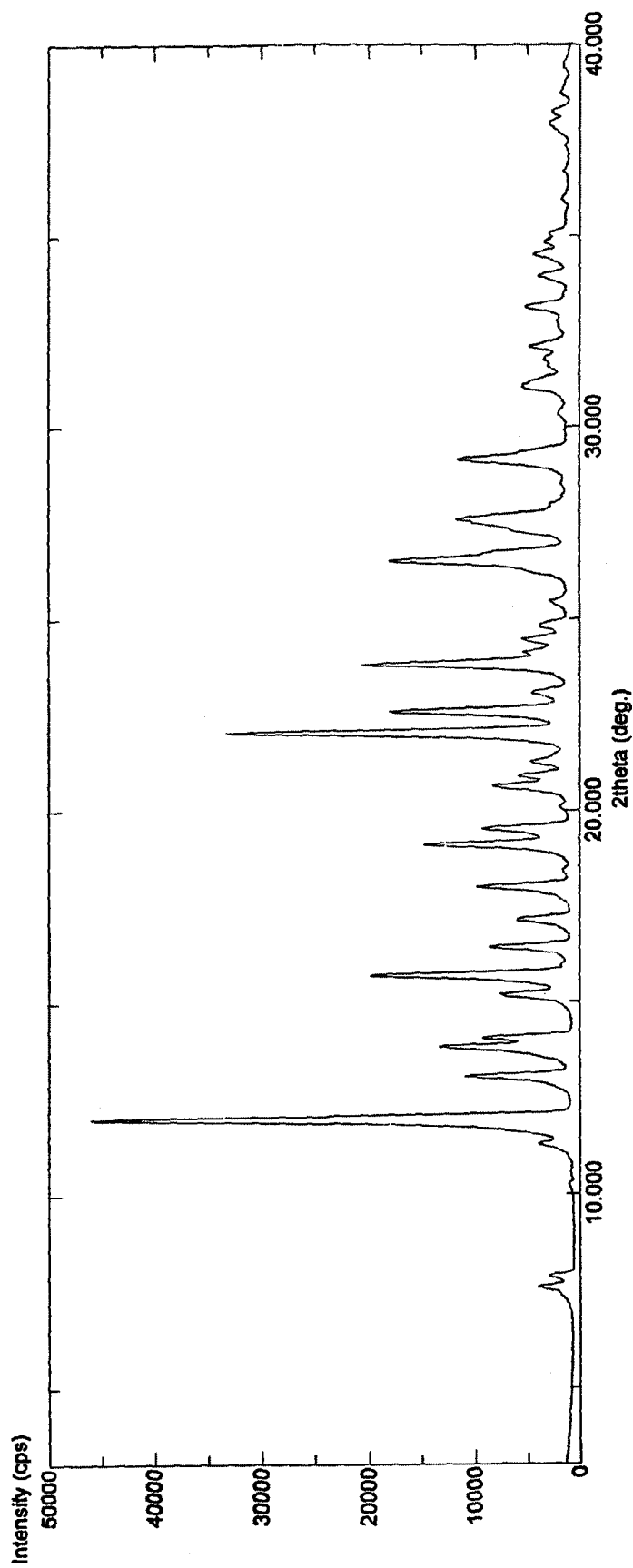
FIG. 9 is an XRPD pattern of the Polymorph I of 3-(4-amino-1-oxo-1,3-dihydro-2H-isoindole-2-yl)-piperidine-2,6-dione of this invention after high humidity for 10 days.
Figures 1, 10:
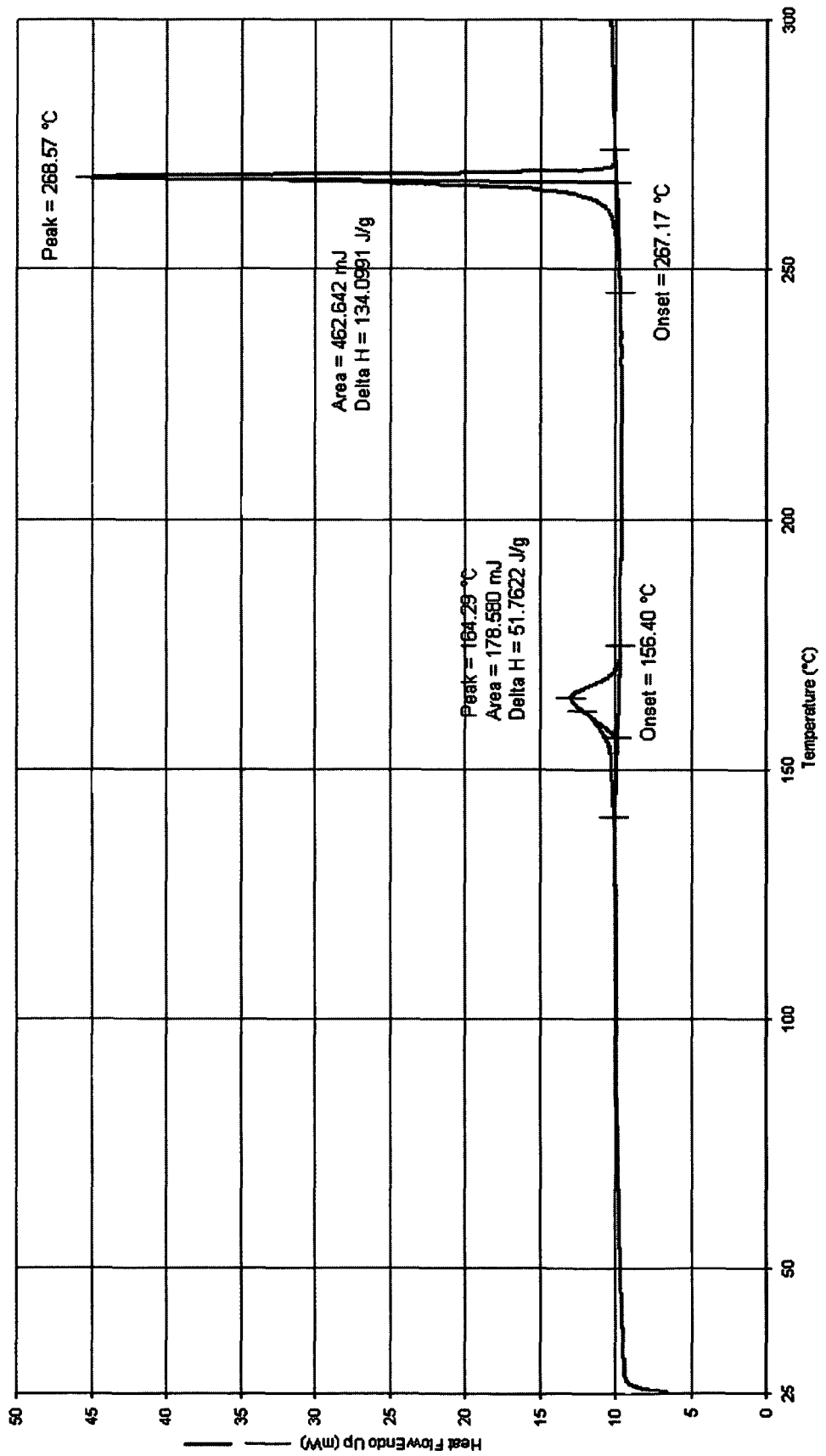
Figures 2, 10:
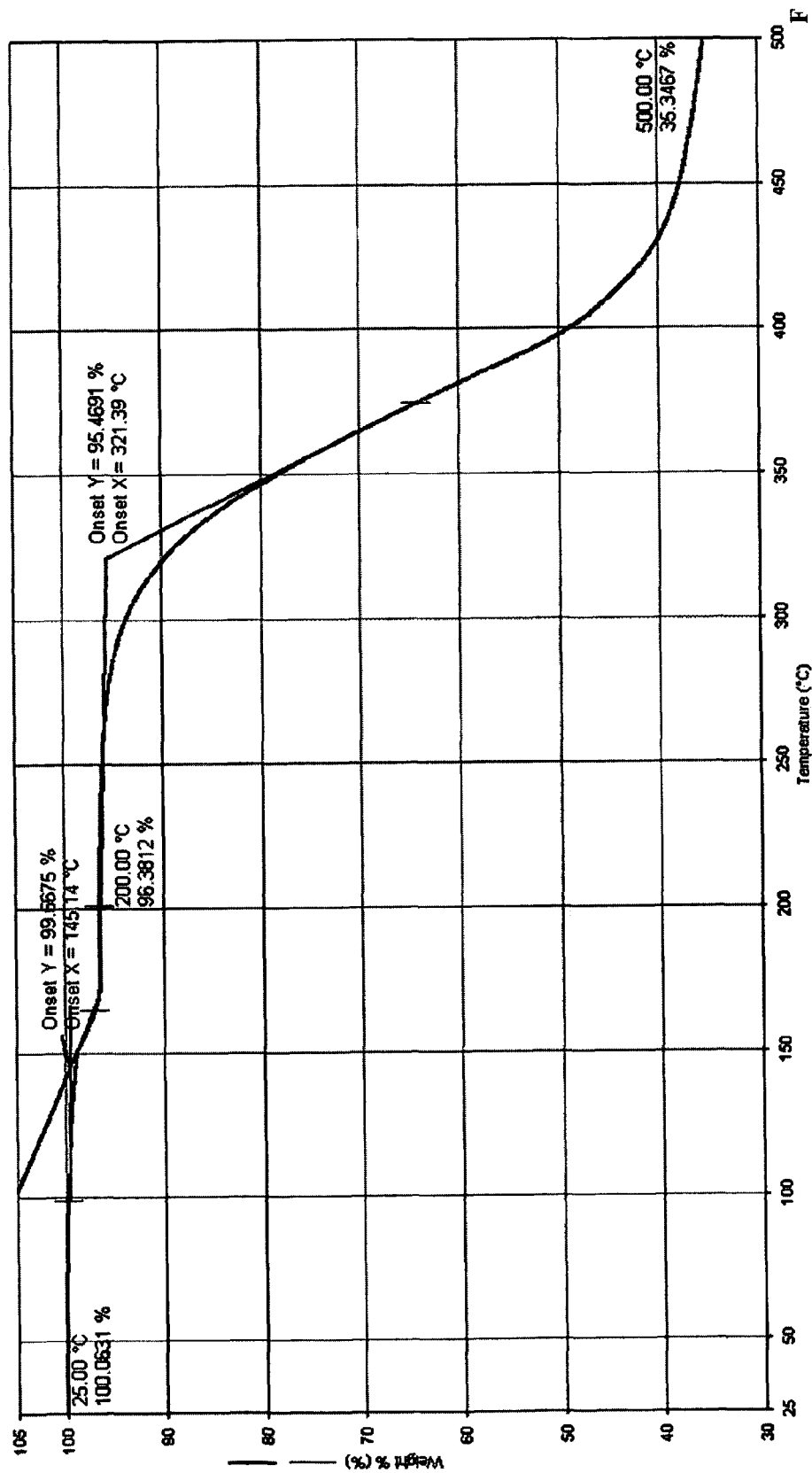

The raw material of Polymorph 1 of 3-(4-amino-1-oxo-1,3-dihydro-2H-isoindole-2-yl)-piperidine-2,6-dione (hemihydrate) was distributed homogeneously in open petri dish with thickness of the raw material not more than 5 mm and put into thermostatic and humidostatic incubator at room temperature (about 25° C.) and 75±5% relative humidity. Sample was tested at the 5$^{th}$ and 10$^{th}$ day respectively and the results were contrasted with that of the Day 0. Results were listed in Tab. 4. After high humidity test of 75±5% relative humidity for 10 days, the X-ray powder diffraction pattern was shown in FIG. 9; DSC diagram was in FIG. 10-1; TGA diagram was in FIG. 10-2.

TABLE 4

High Humidity Test (room temperature and 75 ± 5% relative humidity)

Items

| Time (days) | Appearance | Weight gain of moisture absorption (%) | Content (%) | Melting point (° C.) |
|---|---|---|---|---|
| 0 | off-white powder | / | 99.87 | 268.66 |
| 5 | off-white powder | 0.65 | 99.85 | / |
| 10 | off-white powder | 0.66 | 99.85 | 267.16 |

Note:
the fluctuation of temperature was between 23° C. and 26° C.

2.4 Accelerated Test

Figure 11:
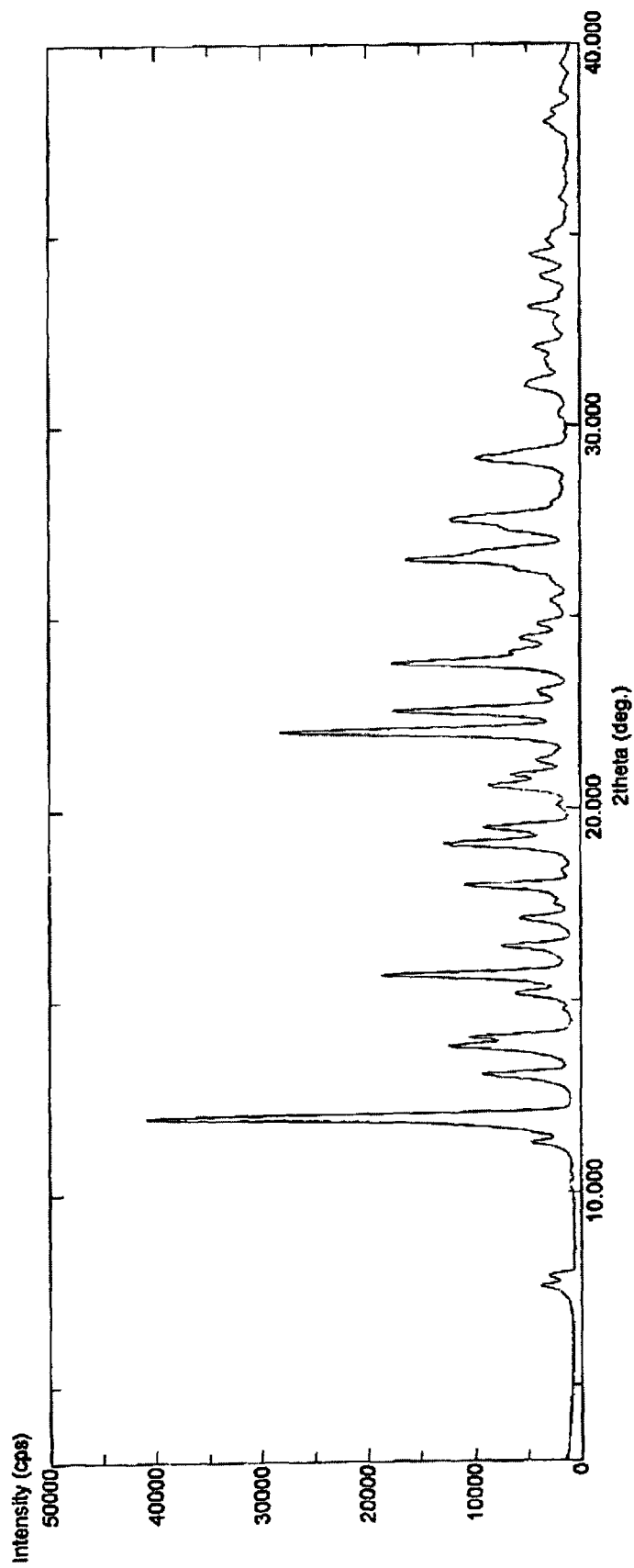
FIG. 11 is an XRPD pattern of the Polymorph I of 3-(4-amino-1-oxo-1,3-dihydro-2H-isoindole-2-yl)-piperidine-2,6-dione of this invention after accelerated test at 40° C. for six months.
Figures 1, 12:
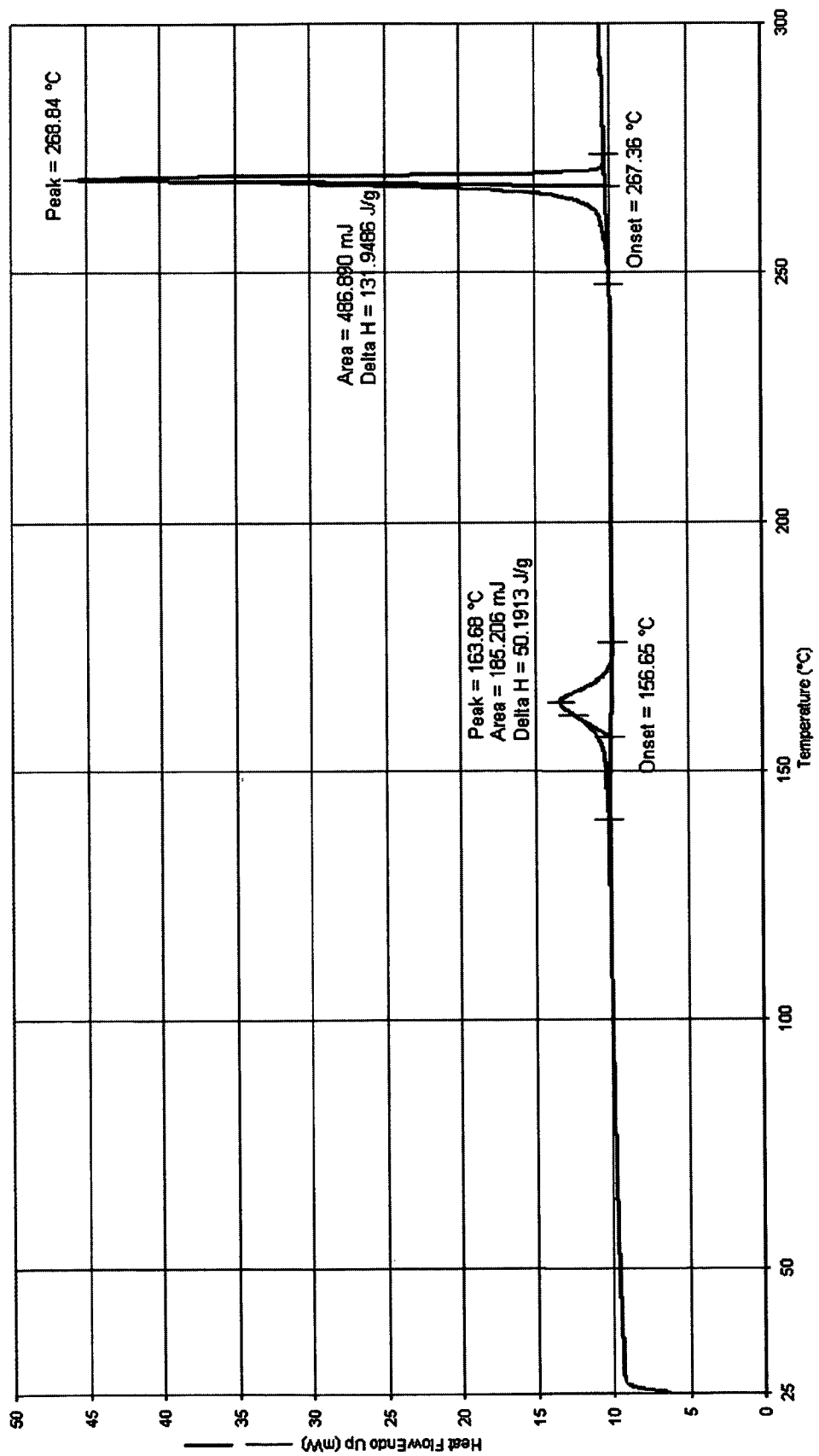
Figures 2, 12:
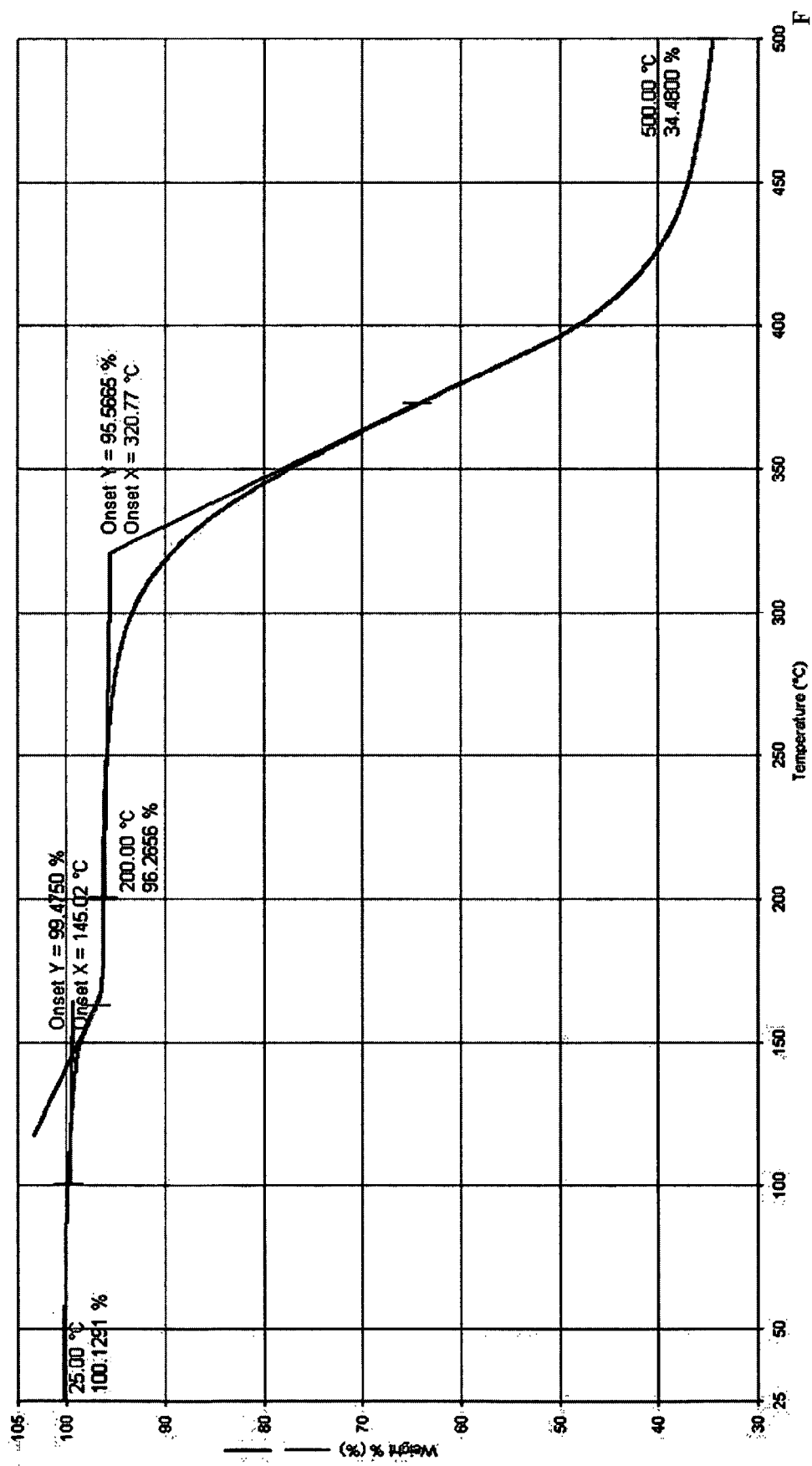

The raw material of Polymorph I of 3-(4-amino-1-oxo-1,3-dihydro-2H-isoindole-2-yl)-piperidine-2,6-dione (hemihydrate) was hermetically packed in plastic bags of polyethylene film and put in thermostatic and humidostatic incubator at 40±2° C. and 75±5% relative humidity for six months. Sample was tested at the end of the 1$^{st}$, 2$^{nd}$, 3$^{rd}$ and 6$^{th}$ month respectively and the results were contrasted with that of the zeroth month. Results were listed in Tab. 5. After accelerated test at 40° C. for six months, the X-ray powder diffraction pattern was shown in FIG. 11; DSC diagram was in FIG. 12-1; TGA diagram was in FIG. 12-2

TABLE 5

Accelerated Test (40° C. and 75% relative humidity)

| Time (months) | Appearance | Related substance (%) | Content (%) | Melting point (° C.) |
|---|---|---|---|---|
| 0 | Off-white powder | 0.05 | 99.87 | 268.66 |
| 1 | Off-white powder | 0.05 | 99.85 | / |
| 2 | Off-white powder | 0.05 | 99.81 | / |
| 3 | Off-white powder | 0.06 | 99.78 | / |
| 6 | Off-white powder | 0.07 | 99.75 | 267.50 |

As is known from above results that in photostability test and high temperature test both appearance and content of Polymorph I of 3-(4-amino-1-oxo-1,3-dihydro-2H-isoindole-2-yl)-piperidine-2,6-dione (hemihydrate) obtained by this invention had few significant variation, which demonstrated the characteristic of stability; in high humidity test, both appearance and content of this product had few obvious change, which verified the characteristic of very slight moisture absorption.

In the observation test of long-term sample storage, crystal transformation was not found, which means that the crystal morphology of this polymorph is relatively stable.

In addition, weight-loss process of the polymorph I happened during a period from 100° C. to 180° C., which could identify the existence of Van Der Waals forces between molecules, calculate weight loss: 100.2825%−96.8165%=3.466% according to TGA scan diagram of the Polymorph I of 3-(4-amino-1-oxo-1,3-dihydro-2H-isoindole-2-yl)-piperidine-2,6-dione (FIG. 3-2), which verified that the Polymorph I of 3-(4-amino-1-oxo-1,3-dihydro-2H-isoindole-2-yl)-piperidine-2,6-dione is hemihydrate.

The characteristics of the Polymorph II of 3-(4-amino-1-oxo-1,3-dihydro-2H-isoindole-2-yl)-piperidine-2,6-dione 1. Solubility Test was performed according to the Examples of Chinese Pharmacopoeia Edition 2005. Method: a definite quantity of the (acetonitrile) solvated Polymorph II of 3-(4-amino-1-oxo-1,3-dihydro-2H-isoindole-2-yl)-piperidine-2,6-dione measured accurately was added into a certain quantity of solvent slowly, while the mixture was shaken strongly for 30 seconds every 5 minutes and the dissolving status within 30 minutes was observed. Results were listed in Tab. 61.

TABLE 6 solubility test of the Polymorph II of 3-(4-amino-1-oxo-1,3-dihydro-2h-isoindole-2-yl)-piperidine-2,6-dione

| Solvent | Sample quantity (g) | Solvent quantity (ml) | Solute Solvent | Dissolving status | Conclusion |
|---|---|---|---|---|---|
| water | 0.0102 | 105 | 1:10294 | cannot fully dissolved | practically insoluble |
| 0.1 mol/L NaOH solution | 0.0515 | 50 | 1:970.9 | fully dissolved | slightly soluble |
| 0.1 mol/L HCl solution | 0.0510 | 5 | 1:98.0 | fully dissolved | sparingly soluble |
| ethanol | 0.0108 | 50 | 1:4629.6 | fully dissolved | very slightly soluble |
| acetonitrile | 0.0114 | 10 | 1:877.2 | fully dissolved | slightly soluble |
| ethyl acetate | 0.0109 | 105 | 1:9633.0 | fully dissolved | very slightly soluble |
| methanol | 0.0107 | 50 | 1:4672.9 | fully dissolved | very slightly soluble |
| Acetic acid | 0.0508 | 5 | 1:98.4 | fully dissolved | sparingly soluble |
| Acetone | 0.0512 | 50 | 1:976.6 | fully dissolved | slightly soluble |
| DMSO | 0.1012 | 1 | 1:9.88 | fully dissolved | freely soluble |
| DMF | 0.1023 | 1 | 1:9.78 | fully dissolved | freely soluble |

The Polymorph II of 3-(4-amino-1-oxo-1,3-dihydro-2h-isoindole-2-yl)-piperidine-2,6-dione was: freely soluble in dimethylsulfoxide and N,N-dimethylformamide; sparingly soluble in acetic acid and 0.1 mol/L HCL solution; slightly soluble in acetonitrile, acetone and 0.1 mol/L NaOH solution; very slightly soluble in methanol, ethanol and ethyl acetate; nearly insoluble in water.

2. Stability 2.1 Photostability Test

Figure 16:
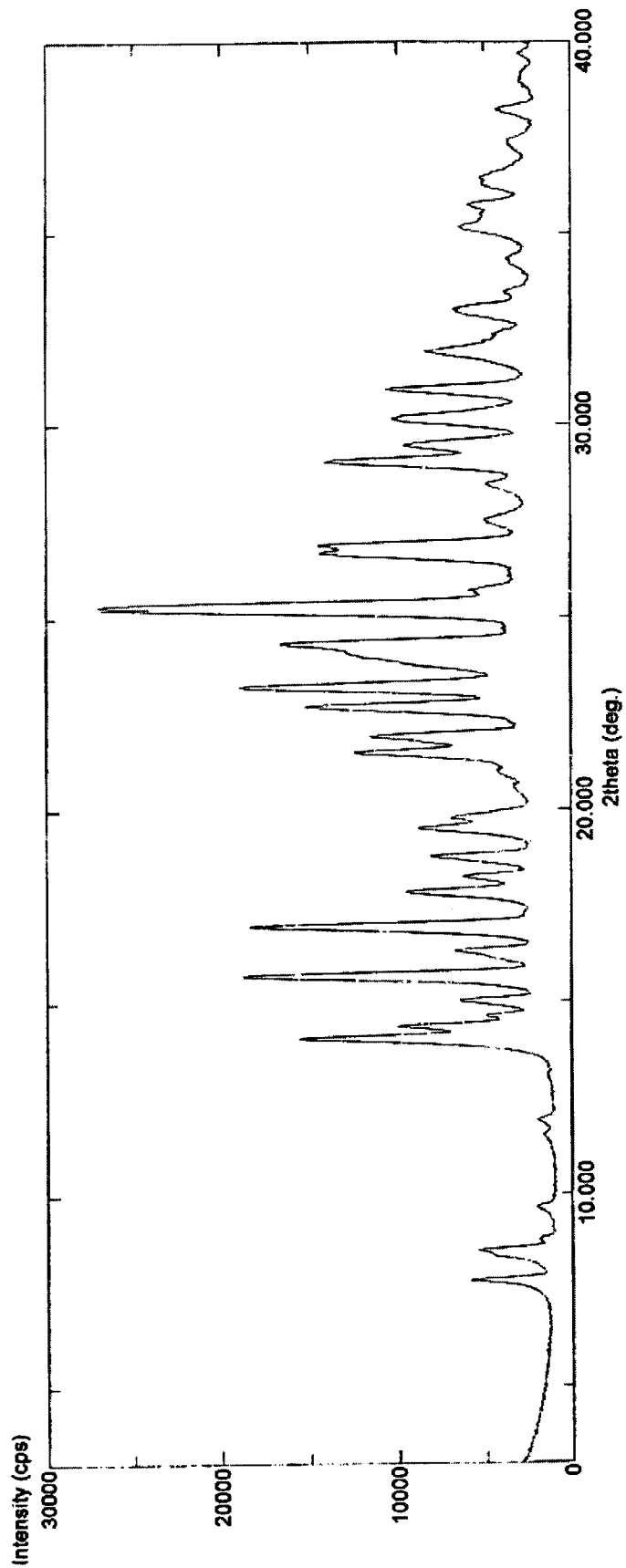
FIG. 16 is an XRPD pattern of the Polymorph II of 3-(4-amino-1-oxo-1,3-dihydro-2H-isoindole-2-yl)-piperidine-2,6-dione of this invention after strong illumination for 10 days.
Figure 17:
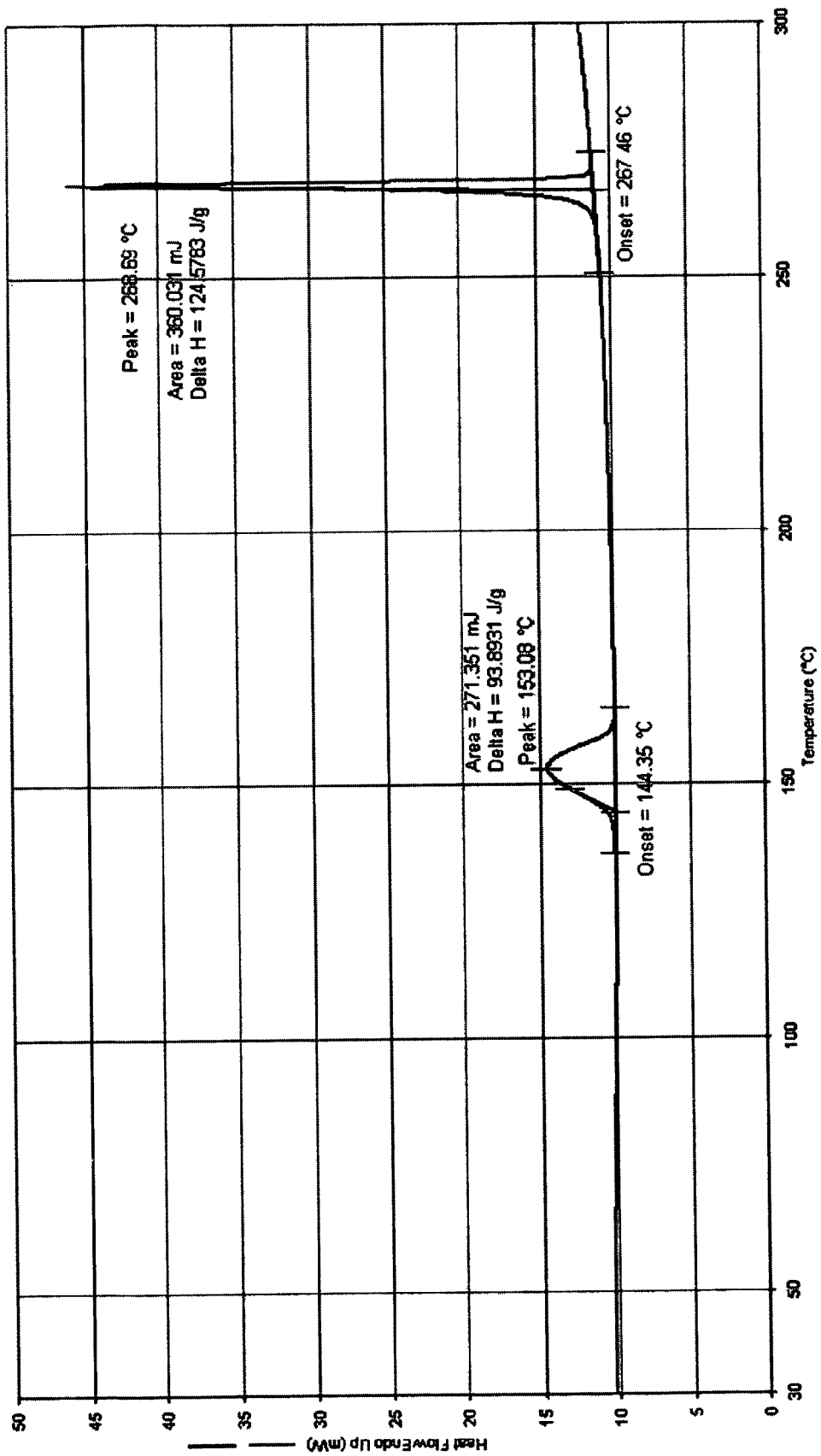
FIG. 17 is a DSC diagram of the Polymorph II of 3-(4-amino-1-oxo-1,3-dihydro-2H-isoindole-2-yl)-piperidine-2,6-dione of this invention after strong illumination for 10 days.

The Polymorph II of 3-(4-amino-1-oxo-1,3-dihydro-2H-isoindole-2-yl)-piperidine-2,6-dione was distributed homogeneously in open petri dish with the thickness of the raw material not more than 5 mm and the distance was adjusted to make illumination intensity at 4500±500 Lx. Sample was tested at the 5$^{th}$ and 10$^{th}$ day respectively and the results were contrasted with that of the Day 0. Results were listed in Tab. 7. After strong illumination for 10 days, the X-ray powder diffraction pattern was shown in FIG. 16; DSC diagram was in FIG. 17

TABLE 7

Photostability Test (4500 ± 500lx)

| Time (days) | Appearance | Related substance (%) | Content (%) | Melting point (° C.) |
|---|---|---|---|---|
| 0 | off-white powder | 0.09 | 99.89 | 269.12 |
| 5 | off-white powder | 0.09 | 99.89 | / |
| 10 | off-white powder | 0.09 | 99.88 | 268.69 |

Note:
the fluctuation of temperature was between 23° C. and 26° C.; relative humidity was between 56% and 63%.

2.2 High Temperature Test

Figure 18:
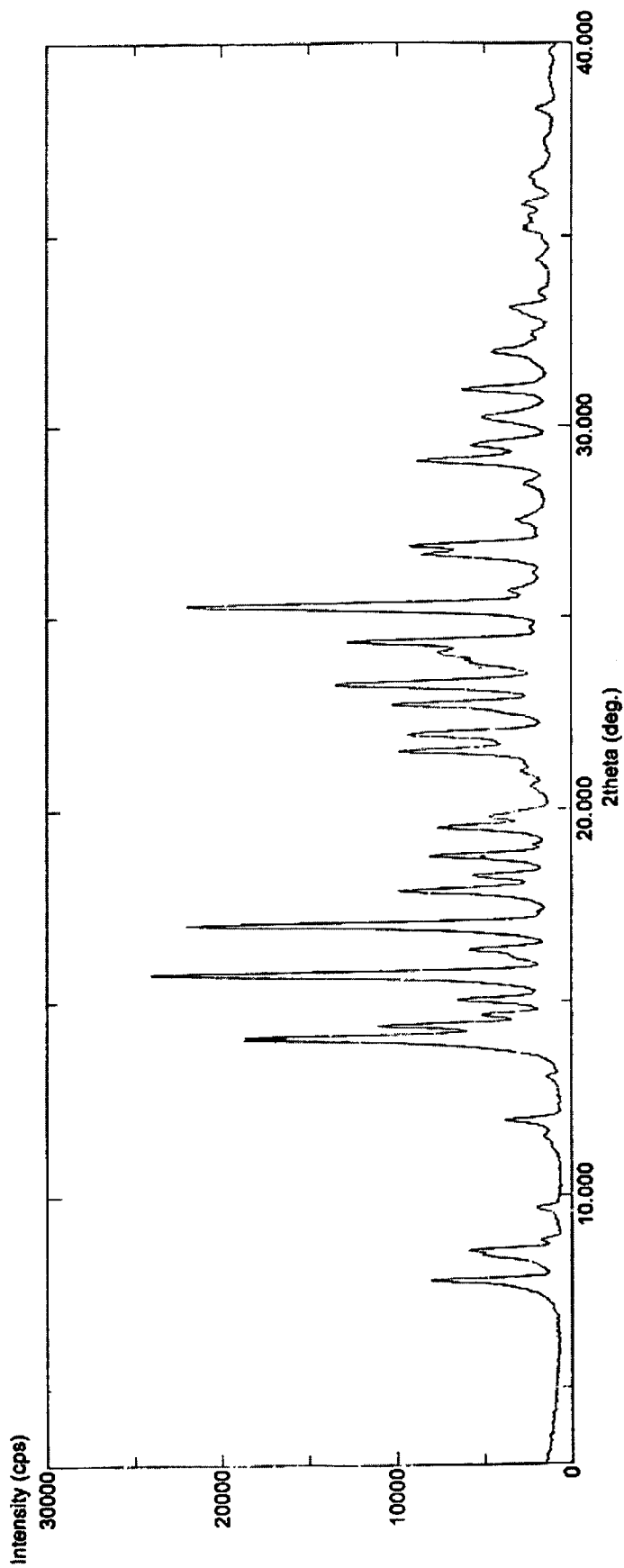
FIG. 18 is an XRPD pattern of the Polymorph II of 3-(4-amino-1-oxo-1,3-dihydro-2H-isoindole-2-yl)-piperidine-2,6-dione of this invention after high temperature test of 60° C. for 10 days.
Figure 19:
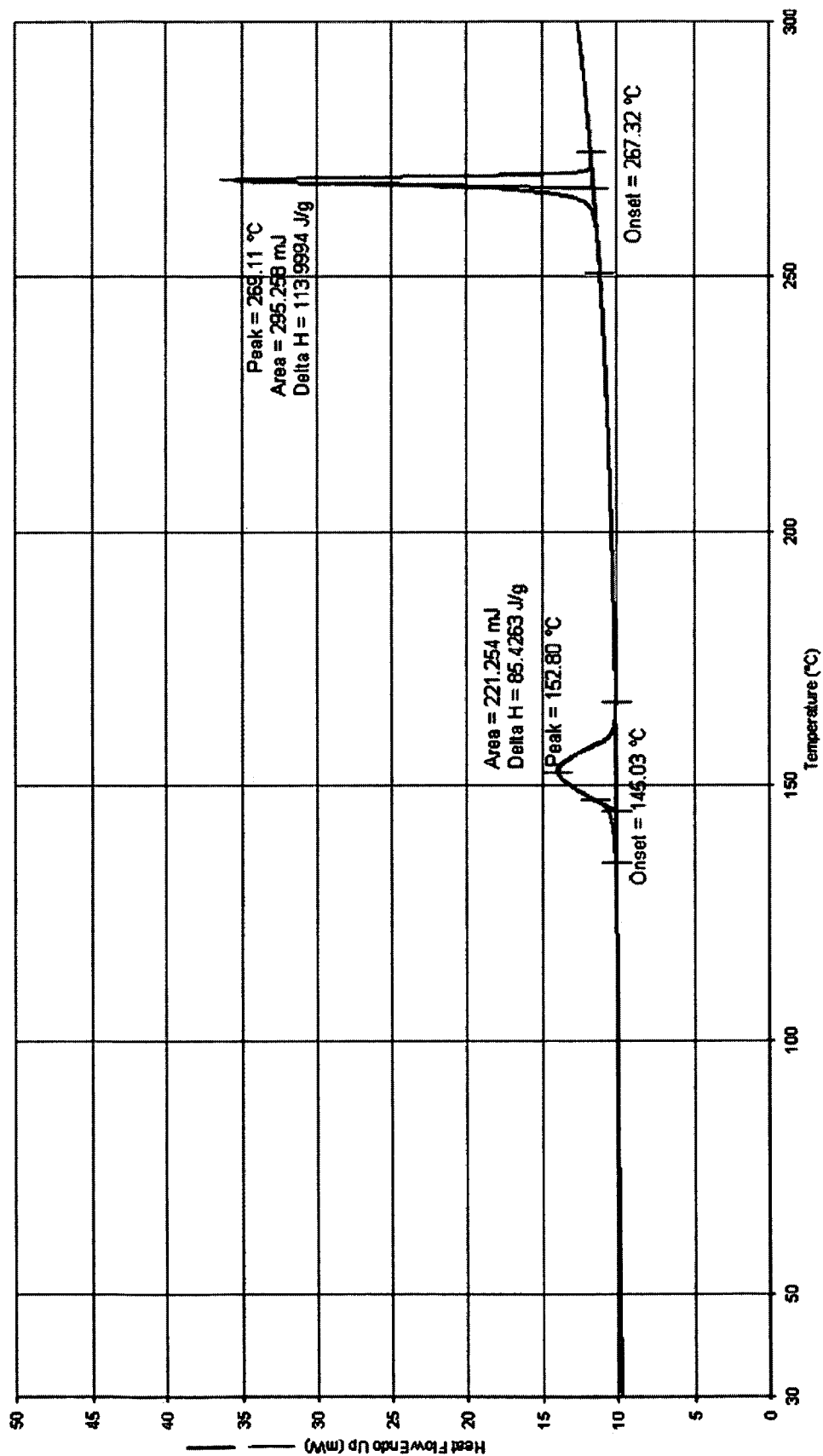
FIG. 19 is a DSC diagram of the Polymorph II of 3-(4-amino-1-oxo-1,3-dihydro-2H-isoindole-2-yl)-piperidine-2,6-dione of this invention after high temperature test of 60° C. for 10 days.

The raw material of Polymorph II of 3-(4-amino-1-oxo-1,3-dihydro-2H-isoindole-2-yl)-piperidine-2,6-dione was put into a clean sealed glass bottle and then put in thermostatic drying chamber at 60° C. Sample was tested at the 5$^{th}$ and 10$^{th}$ day respectively and the results were contrasted with that of the Day 0. Results were listed in Tab. 8. After high temperature test of 60° C. for 10 days, the X-ray powder diffraction pattern was shown in FIG. 18; DSC diagram was in FIG. 19.

TABLE 8

High Temperature Test (60° C.)

| Time (days) | Appearance | Related substance (%) | Content (%) | Melting point (° C.) |
|---|---|---|---|---|
| 0 | Off-white powder | 0.09 | 99.89 | 269.12 |
| 5 | Off-white powder | 0.09 | 99.86 | / |
| 10 | Off-white powder | 0.10 | 99.87 | 269.11 |

Note:
the variation of relative humidity was between 54% and 62%.

2.3 High Humidity Test

Figure 20:
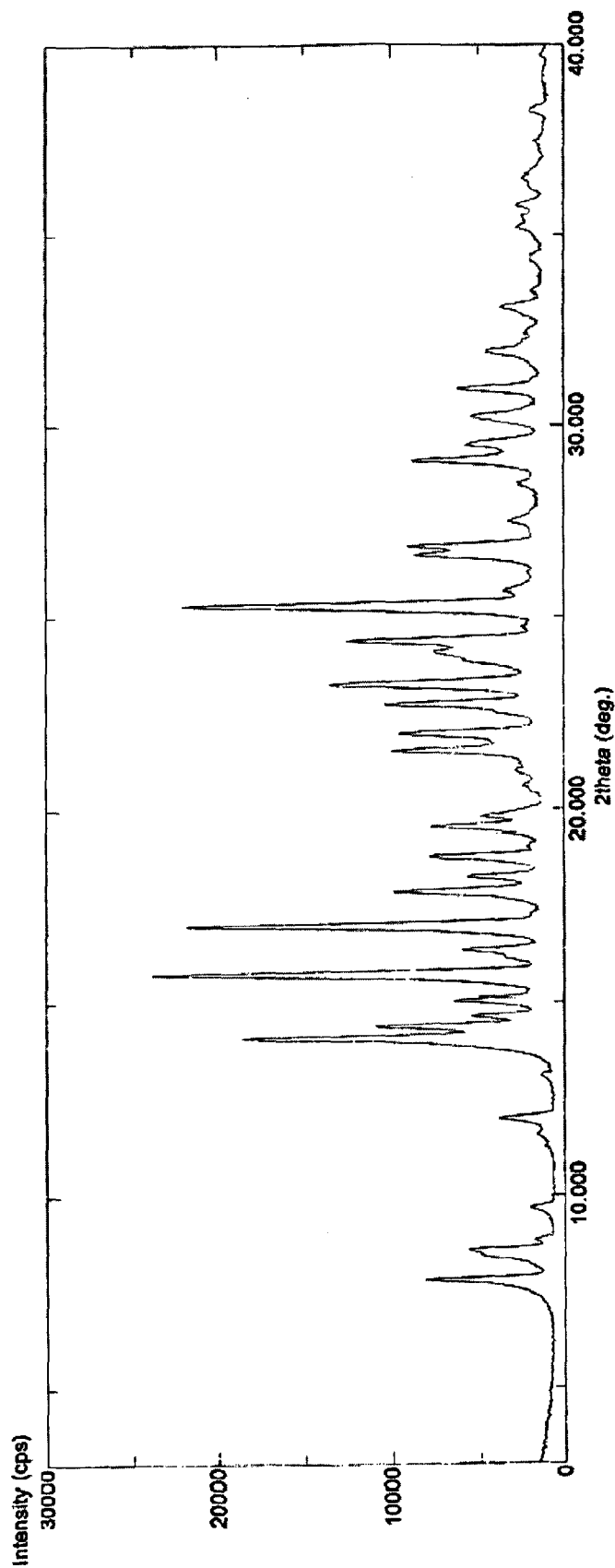
FIG. 20 is an XRPD pattern of the Polymorph II of 3-(4-amino-1-oxo-1,3-dihydro-2H-isoindole-2-yl)-piperidine-2,6-dione of this invention after high humidity for 10 days.
Figures 1, 21:
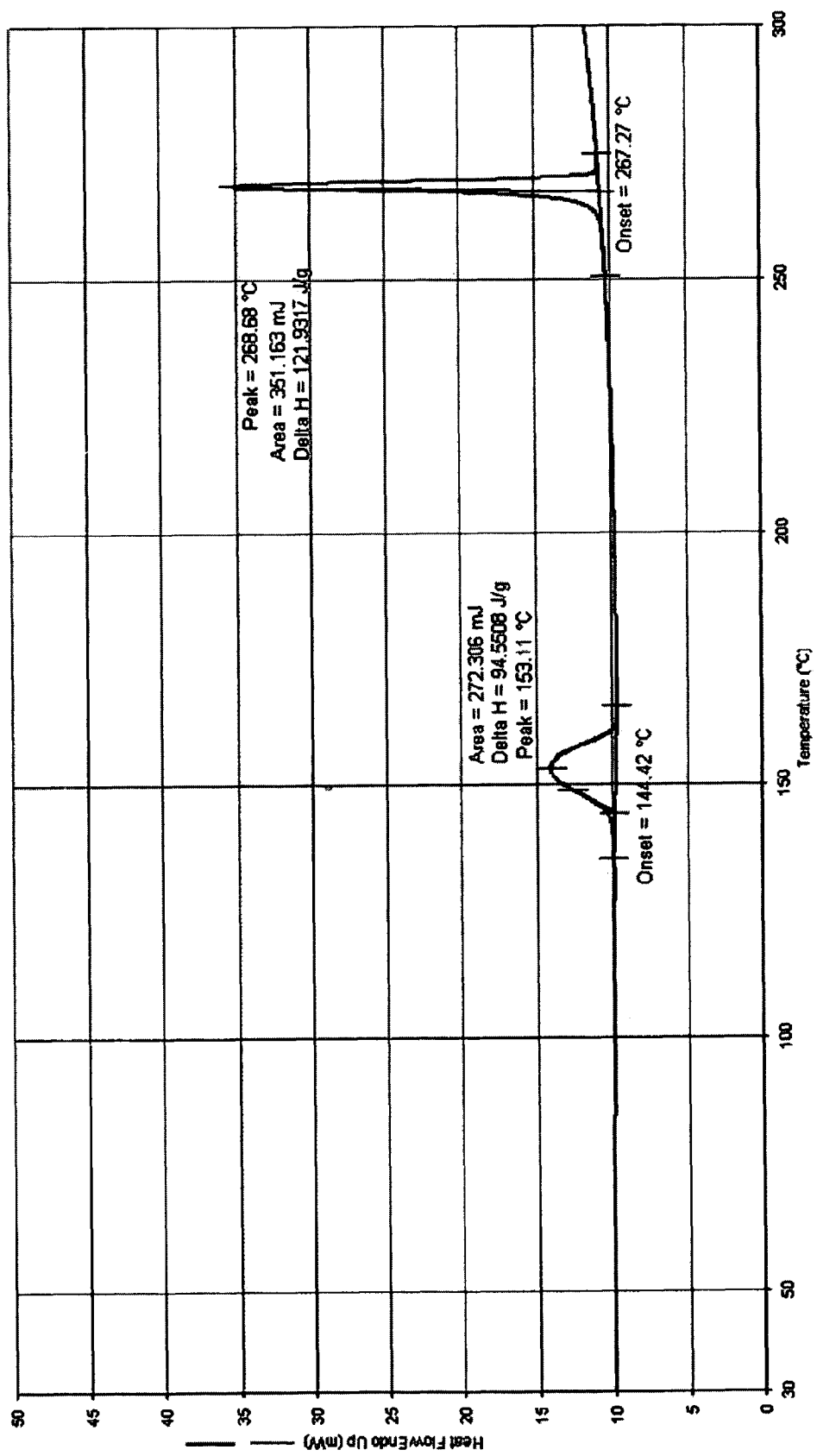
Figures 2, 21:
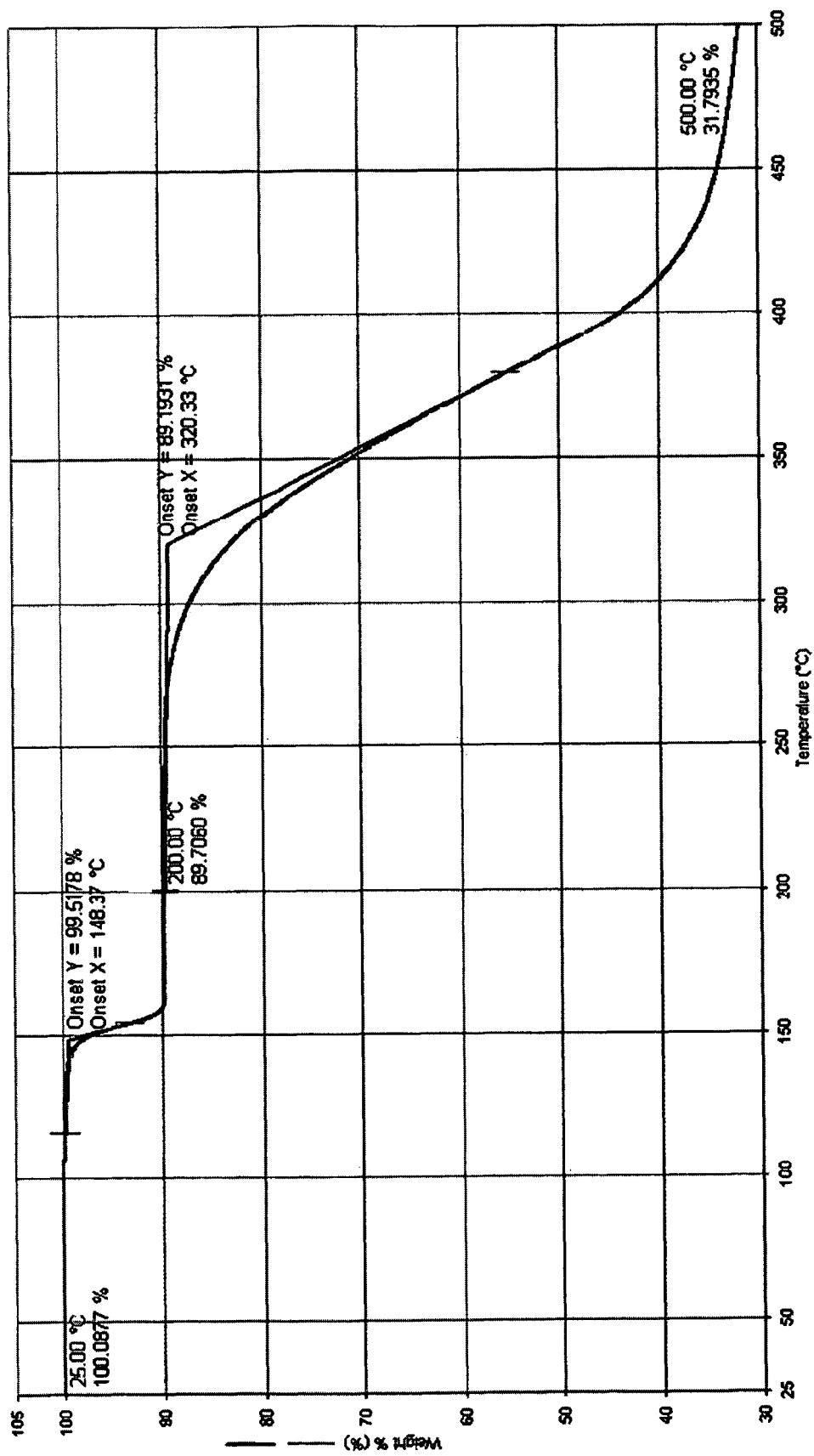

The raw material of Polymorph II of 3-(4-amino-1-oxo-1,3-dihydro-2H-isoindole-2-yl)-piperidine-2,6-dione was distributed homogeneously in open petri dish with thickness of the raw material not more than 5 mm and put into thermostatic and humidostatic incubator at room temperature (about 25° C.) and 75±5% relative humidity. Sample was tested at the $5^{th}$ and $10^{th}$ day respectively and the results were contrasted with that of the Day 0. Results were listed in Tab. 9. After high humidity test of 75±5% relative humidity for 10 days, the X-ray powder diffraction pattern was shown in FIG. 20; DSC diagram was in FIG. 21-1; TGA diagram was in FIG. 21-2.

TABLE 9

High Humidity Test (room temperature and 75 ± 5% relative humidity)

| Time (days) | Appearance | Weight gain of moisture absorption (%) | Content (%) | Melting point (° C.) |
|---|---|---|---|---|
| 0 | off-white powder | / | 99.89 | 269.12 |
| 5 | off-white powder | 1.33 | 99.87 | / |
| 10 | off-white powder | 2.15 | 99.87 | 268.68 |

Note:
the fluctuation of temperature was between 23° C. and 26° C.

2.4 Accelerated Test

Figure 22:
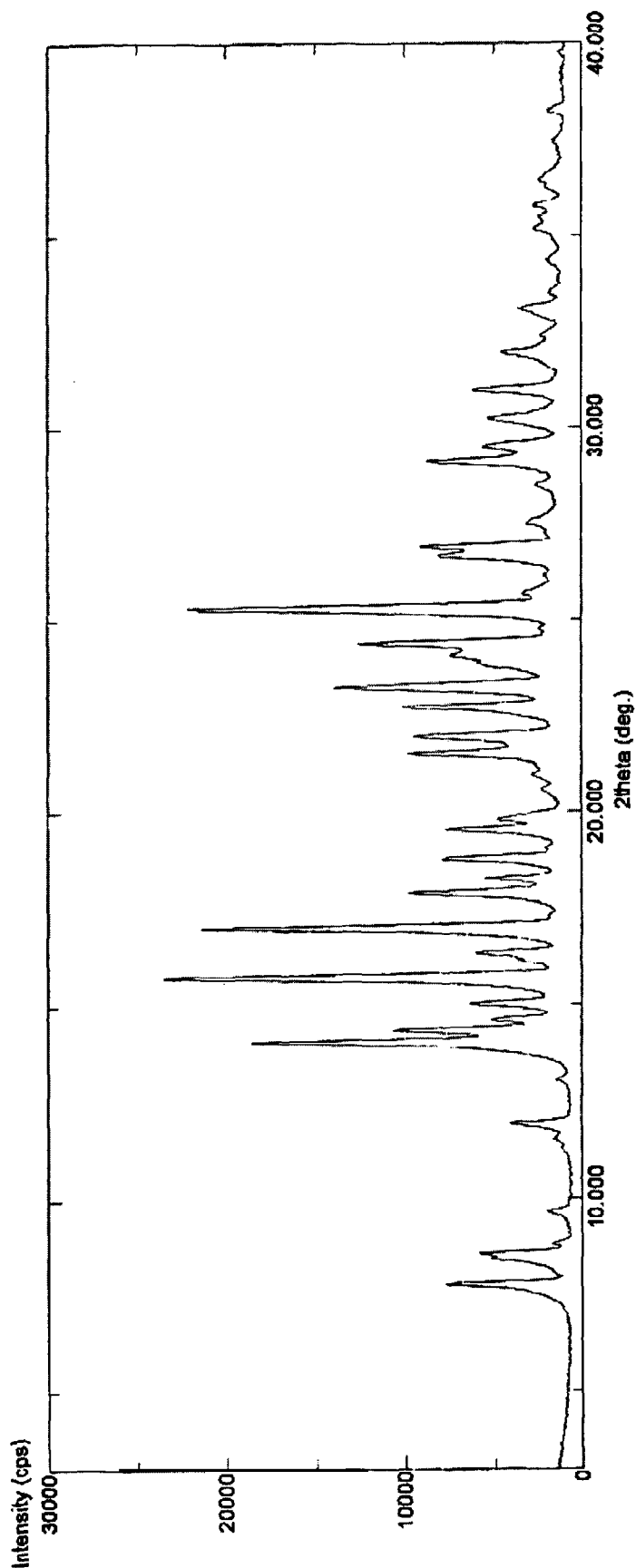
FIG. 22 is an XRPD pattern of the Polymorph II of 3-(4-amino-1-oxo-1,3-dihydro-2H-isoindole-2-yl)-piperidine-2,6-dione of this invention after accelerated test at 40° C. for six months.
Figures 1, 23:
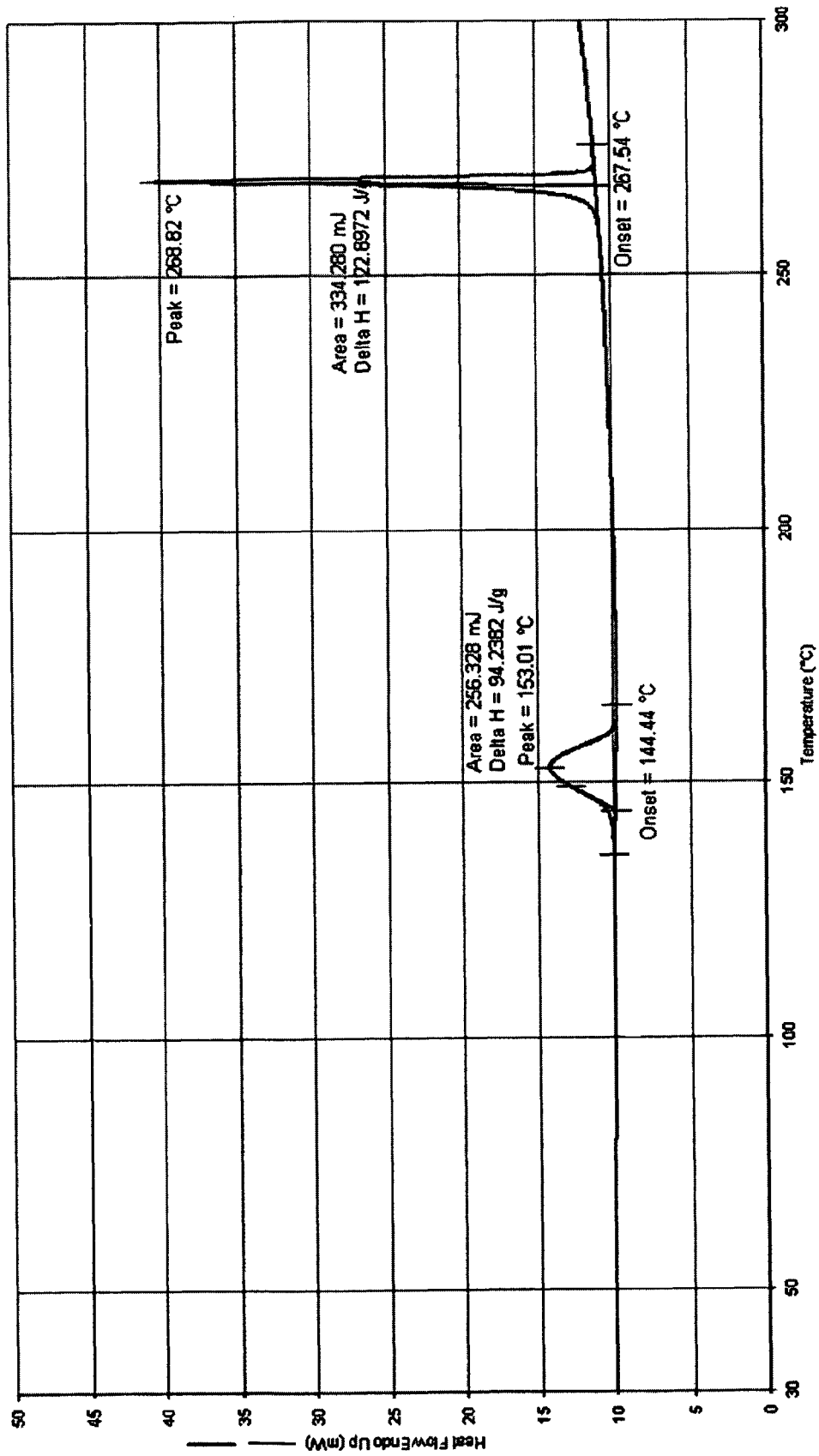
Figures 2, 23:
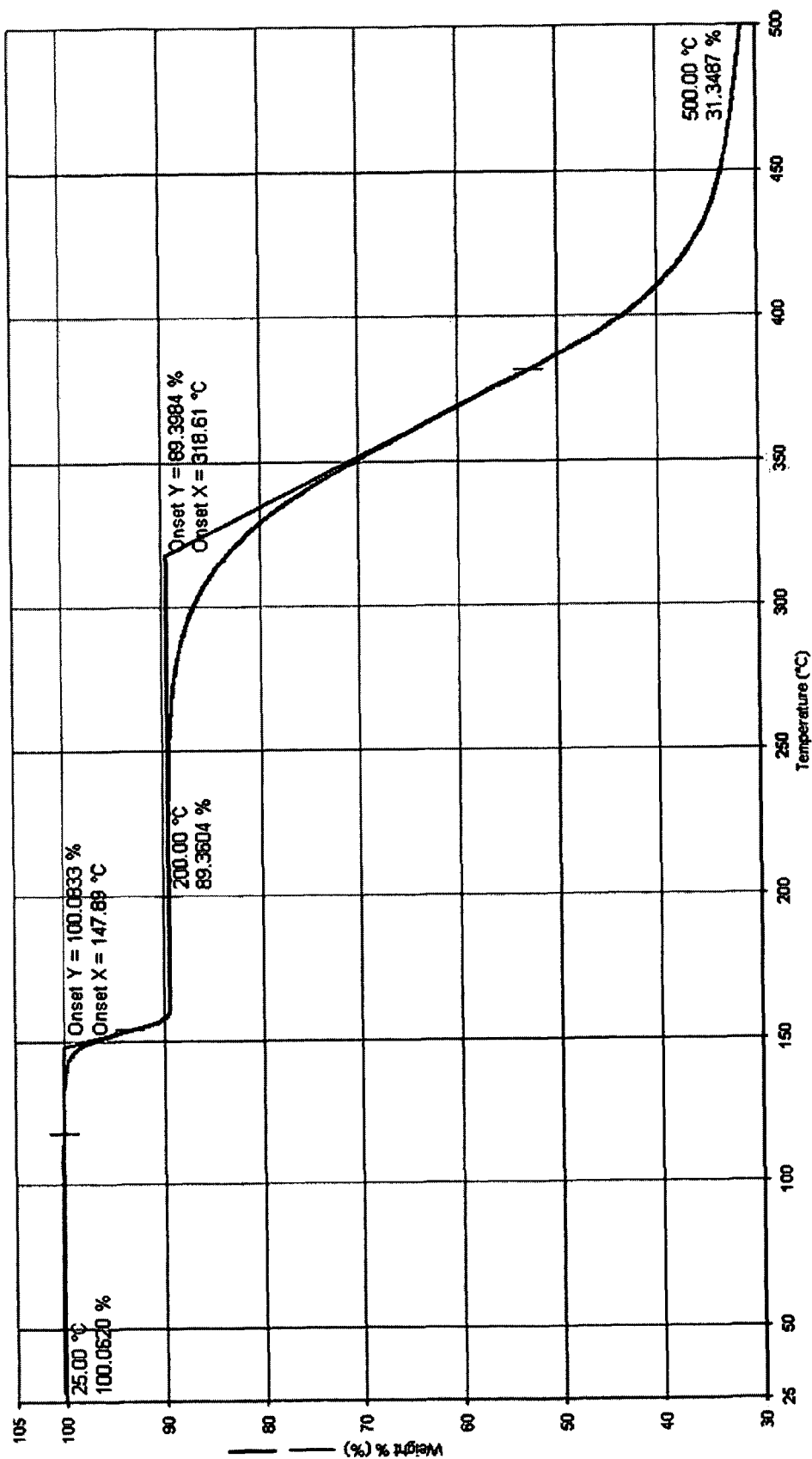

The raw material of Polymorph II of 3-(4-amino-1-oxo-1,3-dihydro-2H-isoindole-2-yl)-piperidine-2,6-dione was hermetically packed in plastic bags of polyethylene film and put in thermostatic and humidostatic incubator at 40±2° C. and 75±5% relative humidity for six months. Sample was tested at the end of the $1^{st}$, $2^{nd}$, $3^{rd}$ and $6^{th}$ month respectively and the results were contrasted with that of the zeroth month. Results were listed in Tab. 10. After accelerated test at 40° C. for six months, the X-ray powder diffraction pattern was shown in FIG. 22; DSC diagram was in FIG. 23-1; TGA diagram was in FIG. 23-2

TABLE 10

Accelerated Test (40° C. and 75% relative humidity)

| Time (months) | Appearance | Related substance (%) | Content (%) | Melting point (° C.) |
|---|---|---|---|---|
| 0 | off-white powder | 0.09 | 99.89 | 269.12 |
| 1 | off-white powder | 0.09 | 99.85 | / |
| 2 | off-white powder | 0.10 | 99.77 | / |
| 3 | off-white powder | 0.10 | 99.72 | / |
| 6 | off-white powder | 0.12 | 99.68 | 268.82 |

As is known from above results that in photostability test and high temperature (60° C.) test both appearance and content of Polymorph II of 3-(4-amino-1-oxo-1,3-dihydro-2H-isoindole-2-yl)-piperidine-2,6-dione obtained by this invention had few significant variation, which verified the characteristic of stability; in high humidity test, both appearance and content of this product had few obvious change, but there is lower moisture absorption. In the observation test of long-term sample storage in high humidity, it was revealed by DSC scanning that a small amount of Polymorph II had transformed to Polymorph I.

The characteristics of the polymorph III of 3-(4-amino-1-oxo-1,3-dihydro-2H-isoindole-2-yl)-piperidine-2,6-dione

1. Solubility

Test was performed according to the Examples of Chinese Pharmacopoeia Edition 2005. Method: a definite quantity of the (acetone) solvated polymorph III of 3-(4-amino-1-oxo-1,3-dihydro-2H-isoindole-2-yl)-piperidine-2,6-dione measured accurately was added into a certain quantity of solvent slowly while the mixture was shaken strongly for 30 seconds every 5 minutes and the dissolving status within 30 minutes was observed. Results were listed in Tab. 11.

TABLE 11 solubility test of the Polymorph III of 3-(4-amino-1-oxo-1,3-dihydro-2H-isoindole-2-yl)-piperidine-2,6-dione

| Solvent | Sample quantity (g) | Solvent quantity (ml) | Solute: Solvent | Dissolving status | Conclusion |
|---|---|---|---|---|---|
| water | 0.0106 | 110 | 1:10377 | cannot fully dissolved | practically insoluble |
| 0.1 mol/L NaOH solution | 0.0512 | 5 | 1:97.7 | fully dissolved | sparingly soluble |
| 0.1 mol/L HCl solution | 0.1030 | 100 | 1:970.9 | fully dissolved | slightly soluble |
| ethanol | 0.0101 | 70 | 1:6930.7 | fully dissolved | very slightly soluble |
| acetonitrile | 0.0524 | 50 | 1:954.2 | fully dissolved | slightly soluble |
| ethyl acetate | 0.0108 | 70 | 1:6481.5 | fully dissolved | very slightly soluble |
| methanol | 0.0115 | 10 | 1:869.6 | fully dissolved | slightly soluble |
| acetic acid | 0.1010 | 9 | 1:89.1 | fully dissolved | sparingly soluble |
| acetone | 0.0522 | 25 | 1:478.9 | fully dissolved | slightly soluble |
| DMSO | 0.1017 | 3 | 1:29.5 | fully dissolved | soluble |
| DMF | 0.1016 | 3 | 1:29.5 | fully dissolved | soluble |

The Polymorph III of 3-(4-amino-1-oxo-1,3-dihydro-2H-isoindole-2-yl)-piperidine-2,6-dione was: soluble in dimethylsulfoxide and N,N-dimethylformamide; sparingly soluble in acetic acid and 0.1 mol/L NaOH solution; slightly soluble in 0.1 mol/L HCL solution, acetonitrile, methanol and acetone; very slightly soluble in water, ethanol and ethyl acetate.

2. Stability

2.1 Photostability Test

Figure 27:
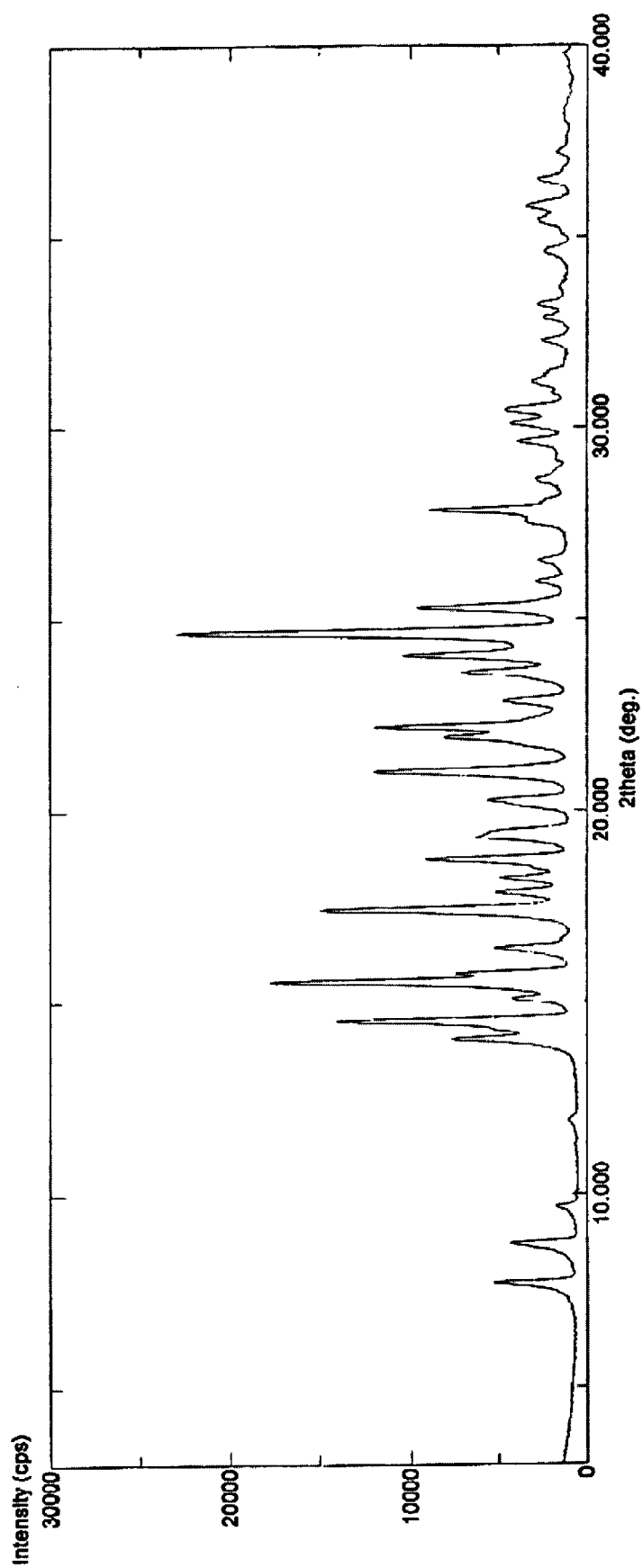
FIG. 27 is XRPD pattern of the Polymorph III of 3-(4-amino-1-oxo-1,3-dihydro-2H-isoindole-2-yl)-piperidine-2,6-dione of this invention after strong illumination for 10 days.
Figure 28:
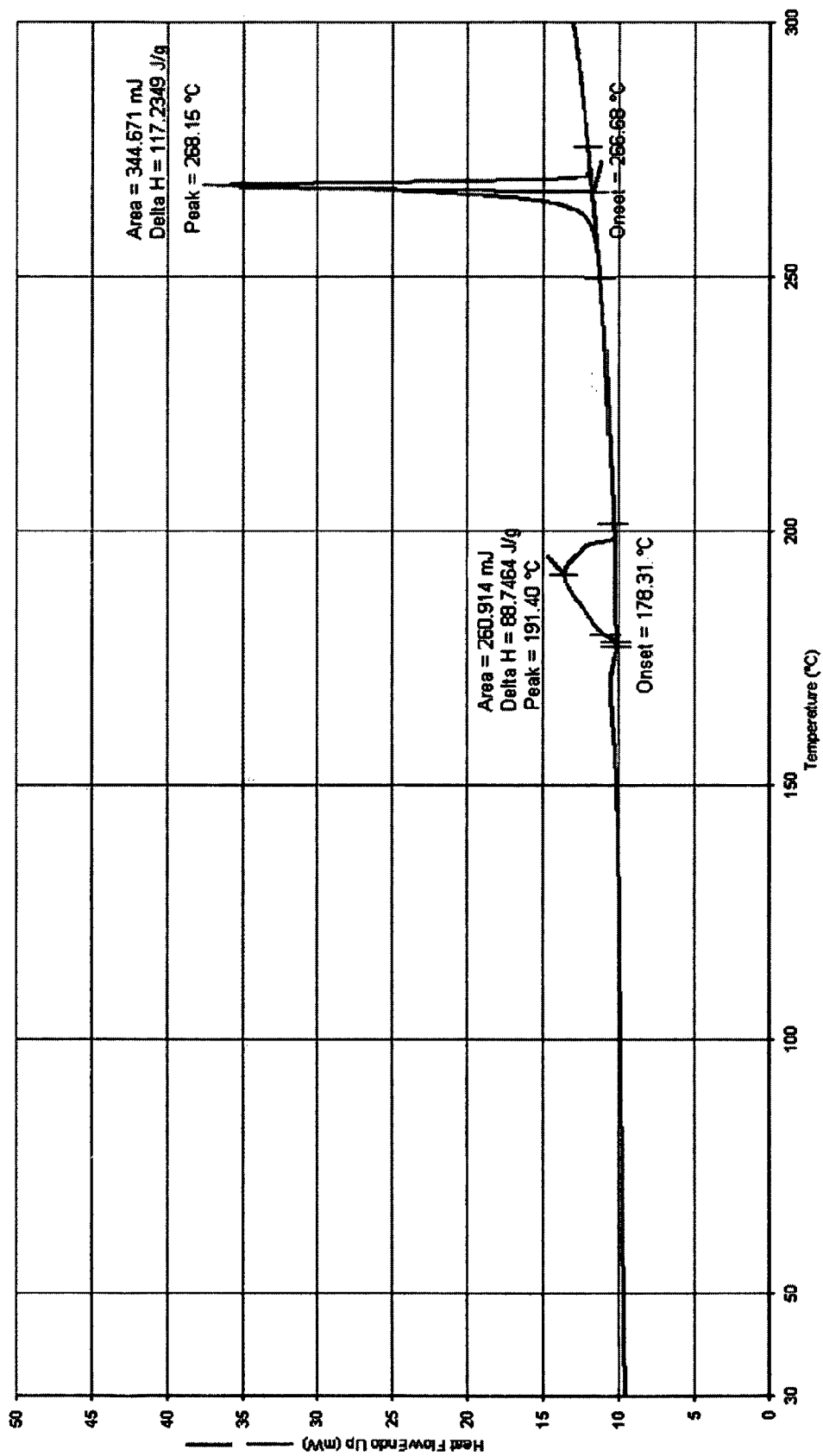
FIG. 28 is DSC diagram of the Polymorph III of 3-(4-amino-1-oxo-1,3-dihydro-2H-isoindole-2-yl)-piperidine-2,6-dione of this invention after strong illumination for 10 days.

The Polymorph III of 3-(4-amino-1-oxo-1,3-dihydro-2H-isoindole-2-yl)-piperidine-2,6-dione was distributed homogeneously in open petri dish with the thickness of the raw material not more than 5 mm and the distance was adjusted to make illumination intensity at 4500±500 Lx. Sample was tested at the $5^{th}$ and $10^{th}$ day respectively and the results were contrasted with that of the Day 0. Results were listed in Tab. 12. After strong illumination for 10 days, the X-ray powder diffraction pattern was shown in FIG. 27; DSC diagram was in FIG. 28

TABLE 12

Photostability Test (4500 ± 500lx)

| Time (days) | Appearance | Items Related substance (%) | Content (%) | Melting point (° C.) |
|---|---|---|---|---|
| 0 | off-white powder | 0.07 | 99.86 | 268.19 |
| 5 | off-white powder | 0.07 | 99.85 | / |
| 10 | off-white powder | 0.07 | 99.85 | 268.15 |

Note:
the fluctuation of temperature was between 23° C. and 26° C.; relative humidity was between 56% and 63%.

2.2 High Temperature Test

Figure 29:
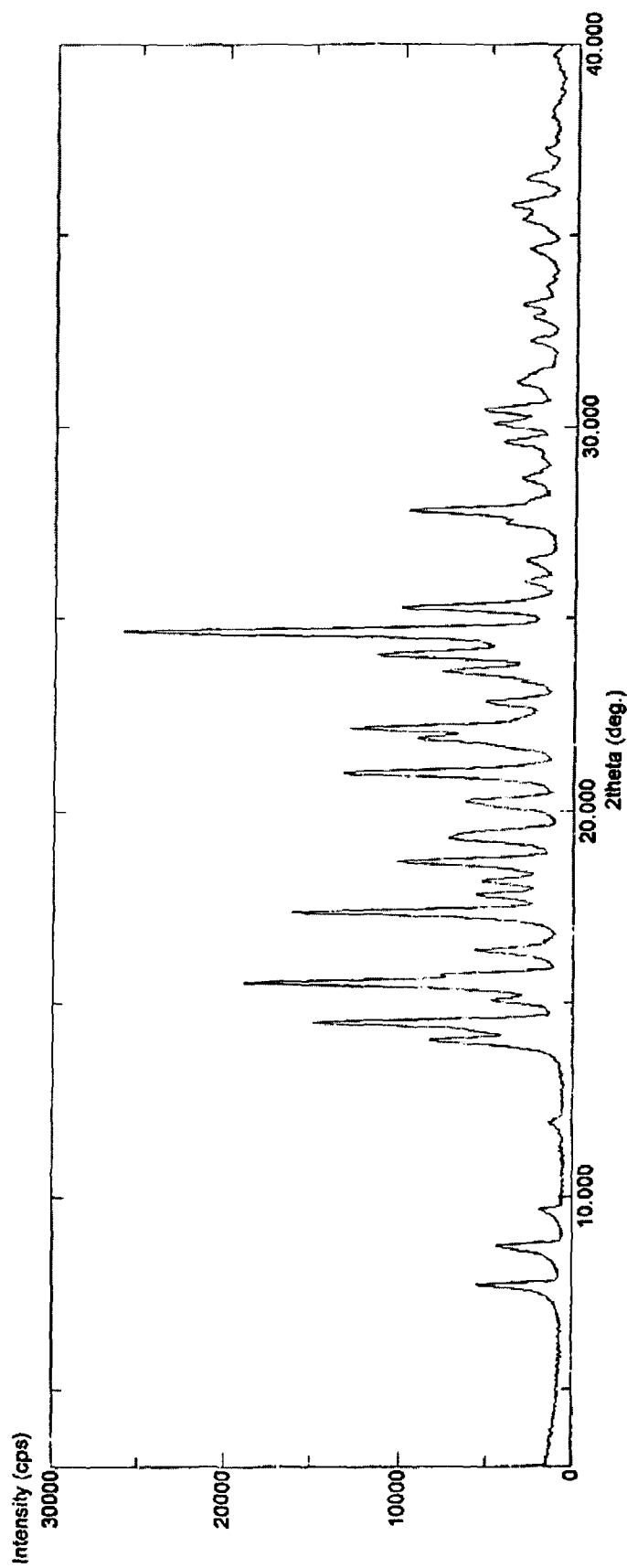
FIG. 29 is an XRPD pattern of the Polymorph III of 3-(4-amino-1-oxo-1,3-dihydro-2H-isoindole-2-yl)-piperidine-2,6-dione of this invention after high temperature test of 60° C. for 10 days.
Figure 30:
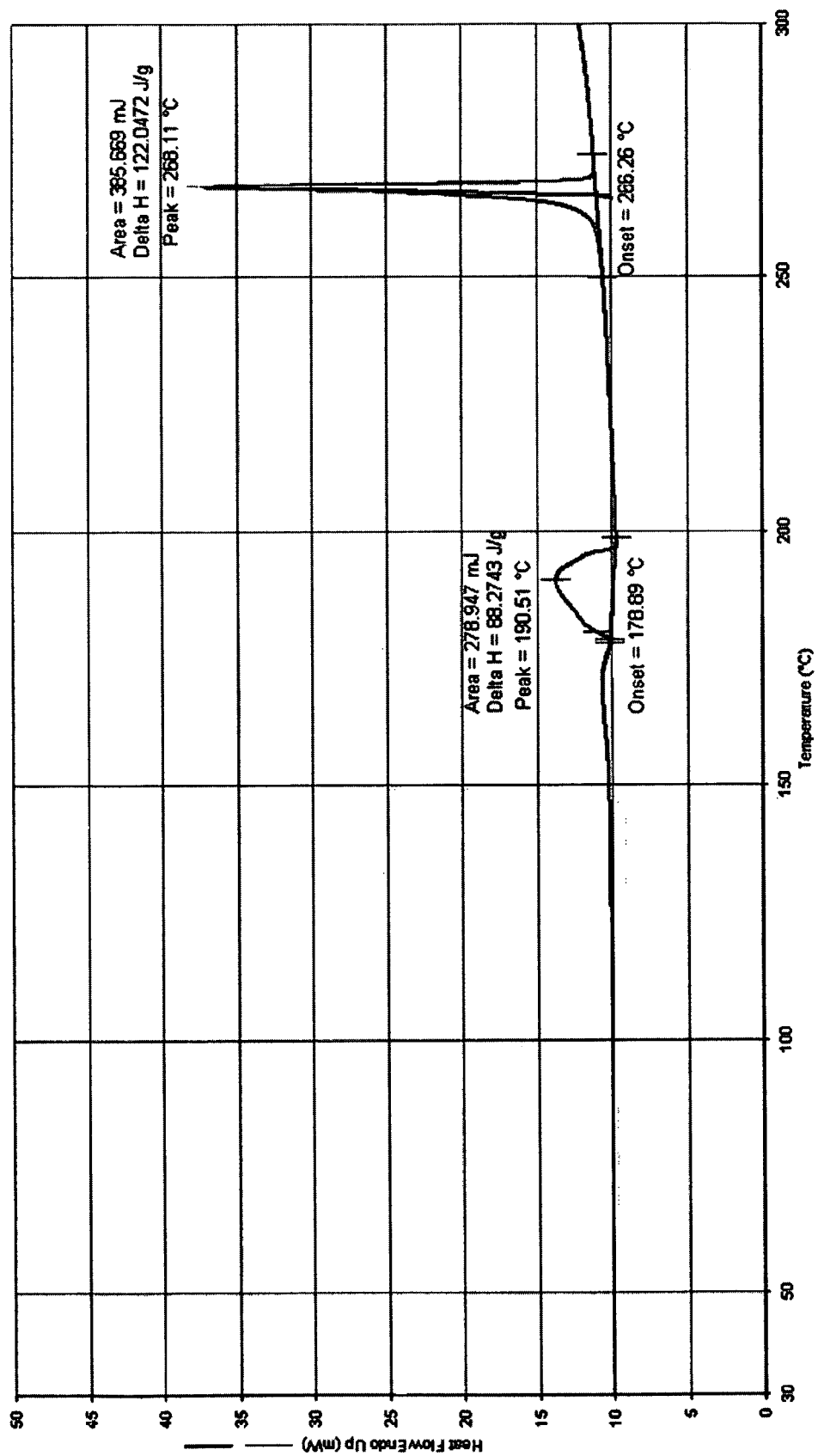
FIG. 30 is a DSC diagram of the Polymorph III of 3-(4-amino-1-oxo-1,3-dihydro-2H-isoindole-2-yl)-piperidine-2,6-dione of this invention after high temperature test of 60° C. for 10 days.

The raw material of Polymorph III of 3-(4-amino-1-oxo-1,3-dihydro-2H-isoindole-2-yl)-piperidine-2,6-dione was put into a clean sealed glass bottle and then put in thermostatic drying chamber at 60° C. Sample was tested at the $5^{th}$ and $10^{th}$ day respectively and the results were contrasted with that of the Day 0. Results were listed in Tab. 13. After high temperature test of 60° C. for 10 days, the X-ray powder diffraction pattern was shown in FIG. 29; DSC diagram was in FIG. 30.

TABLE 13

High Temperature Test (60° C.)

| Time (days) | Appearance | Items Related substance (%) | Content (%) | Melting point (° C.) |
|---|---|---|---|---|
| 0 | off-white powder | 0.07 | 99.86 | 268.19 |
| 5 | off-white powder | 0.07 | 99.84 | / |
| 10 | off-white powder | 0.08 | 99.83 | 268.11 |

Note:
the variation of relative humidity was between 54% and 62%.

2.3 High Humidity Test

Figure 31:
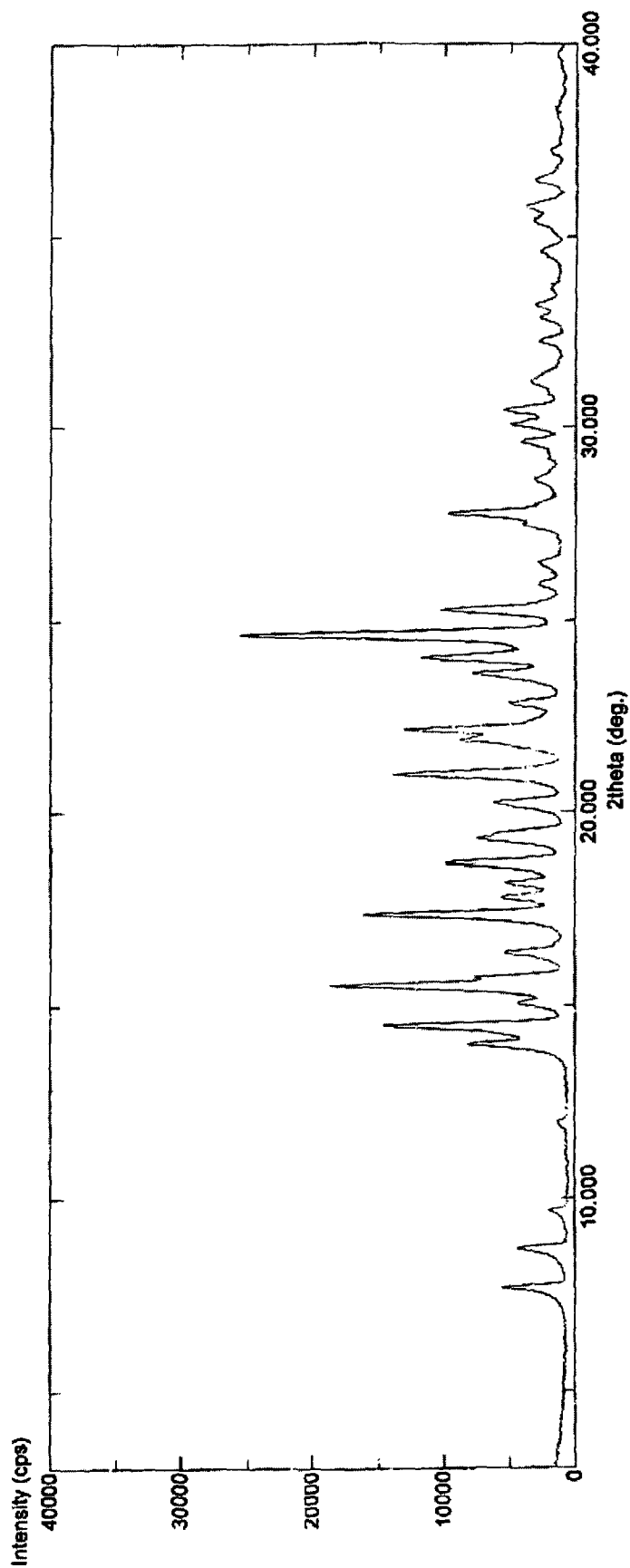
FIG. 31 is an XRPD pattern of the Polymorph III of 3-(4-amino-1-oxo-1,3-dihydro-2H-isoindole-2-yl)-piperidine-2,6-dione of this invention after high humidity for 10 days.
Figures 1, 32:
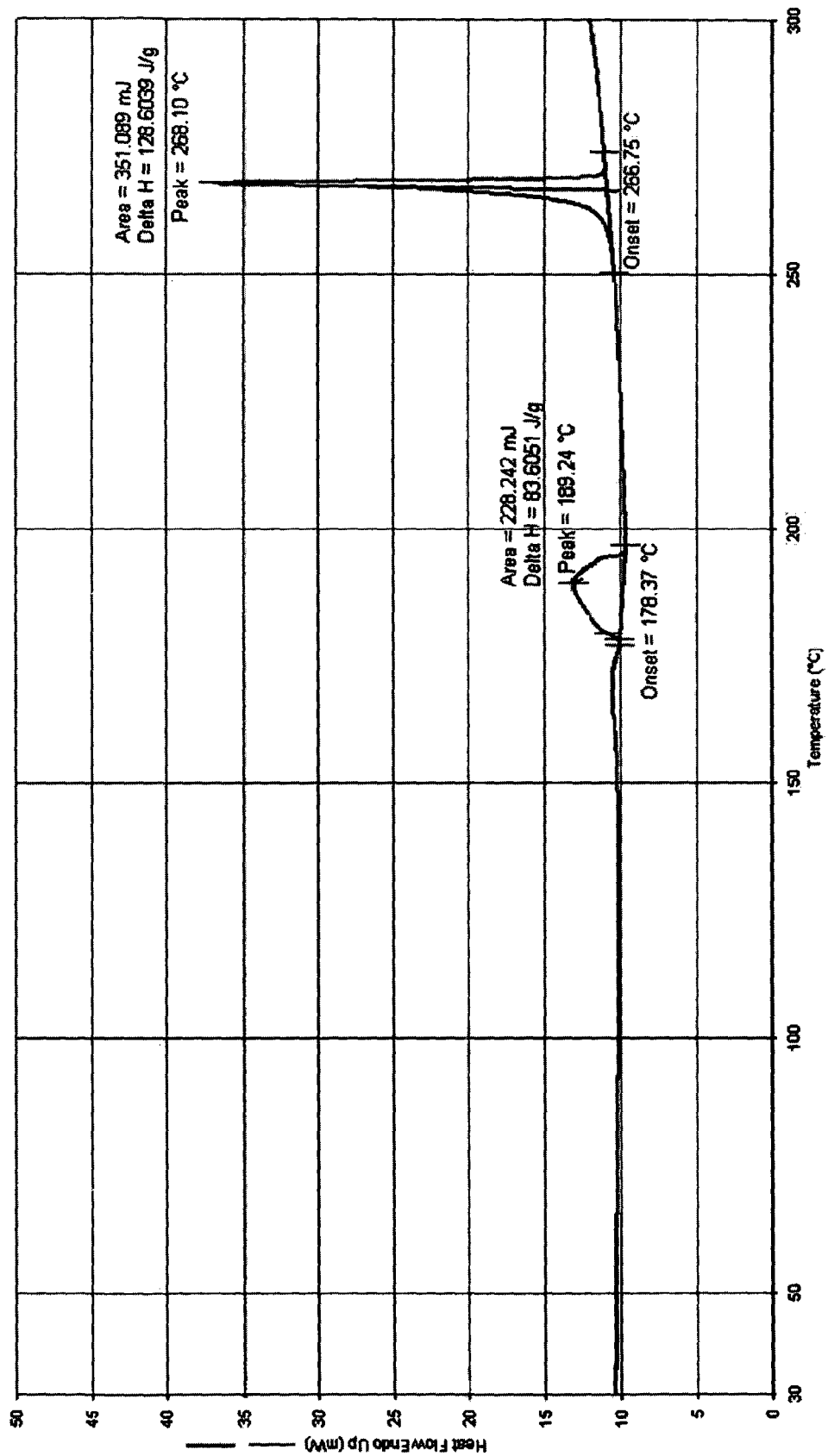
Figures 2, 32:
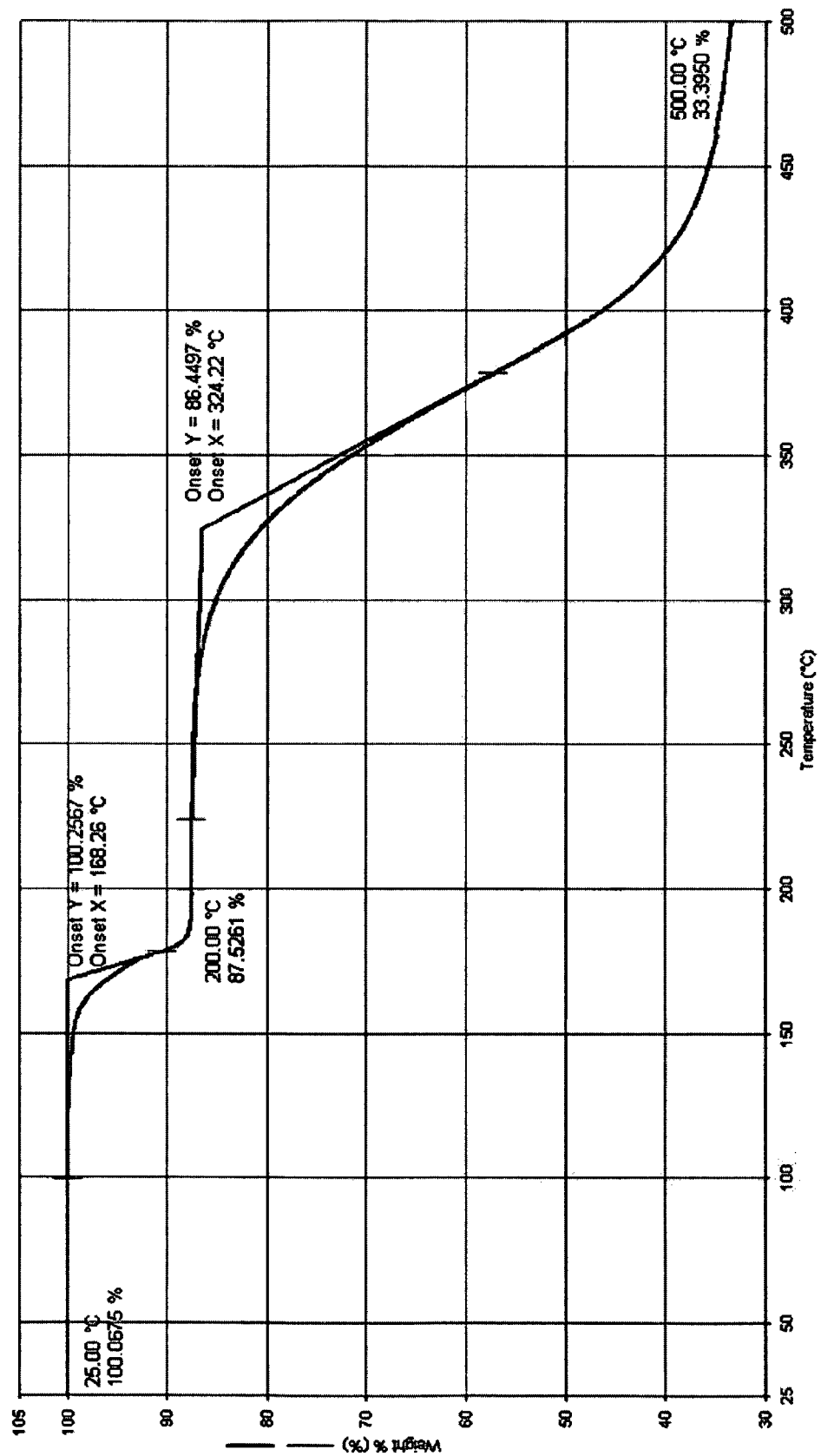

The raw material of Polymorph III of 3-(4-amino-1-oxo-1,3-dihydro-2H-isoindole-2-yl)-piperidine-2,6-dione was distributed homogeneously in open petri dish with thickness of the raw material not more than 5 mm and put into thermostatic and humidostatic incubator at room temperature (about 25° C.) and 75±5% relative humidity. Sample was tested at the $5^{th}$ and $10^{th}$ day respectively and the results were contrasted with that of the Day 0. Results were listed in Tab. 14. After high humidity test of 75±5% relative humidity for 10 days, the X-ray powder diffraction pattern was shown in FIG. 31; DSC diagram was in FIG. 32-1; TGA diagram was in FIG. 32-2.

TABLE 14

High Humidity Test (room temperature and 75 ± 5% relative humidity)

| Time (days) | appearance | Items Weight gain of moisture absorption (%) | Content (%) | Melting point (° C.) |
|---|---|---|---|---|
| 0 | off-white powder | / | 99.86 | 268.19 |
| 5 | off-white powder | 1.25 | 99.83 | / |
| 10 | off-white powder | 1.37 | 99.82 | 268.10 |

Note:
the fluctuation of temperature was between 23° C. and 26° C.

2.4 Accelerated Test

Figure 33:
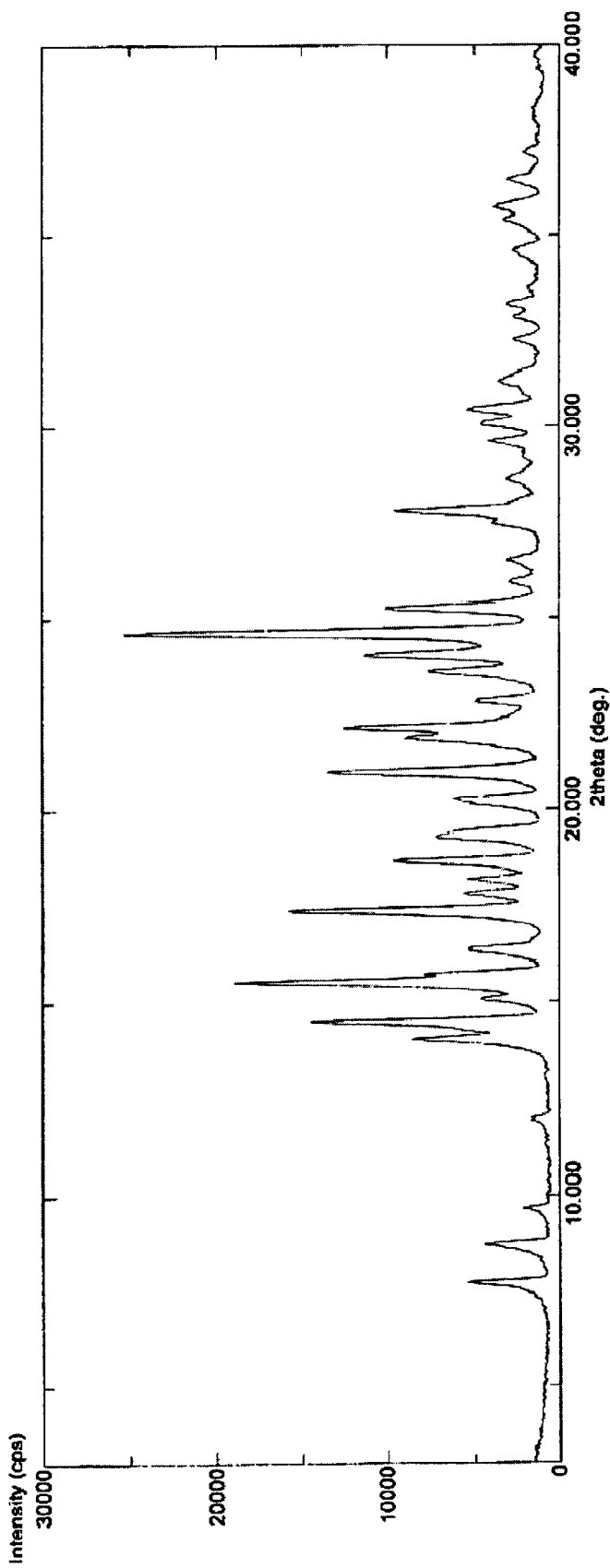
FIG. 33 is an XRPD pattern of the Polymorph III of 3-(4-amino-1-oxo-1,3-dihydro-2H-isoindole-2-yl)-piperidine-2,6-dione of this invention after accelerated test at 40° C. for six months.
Figures 1, 34:
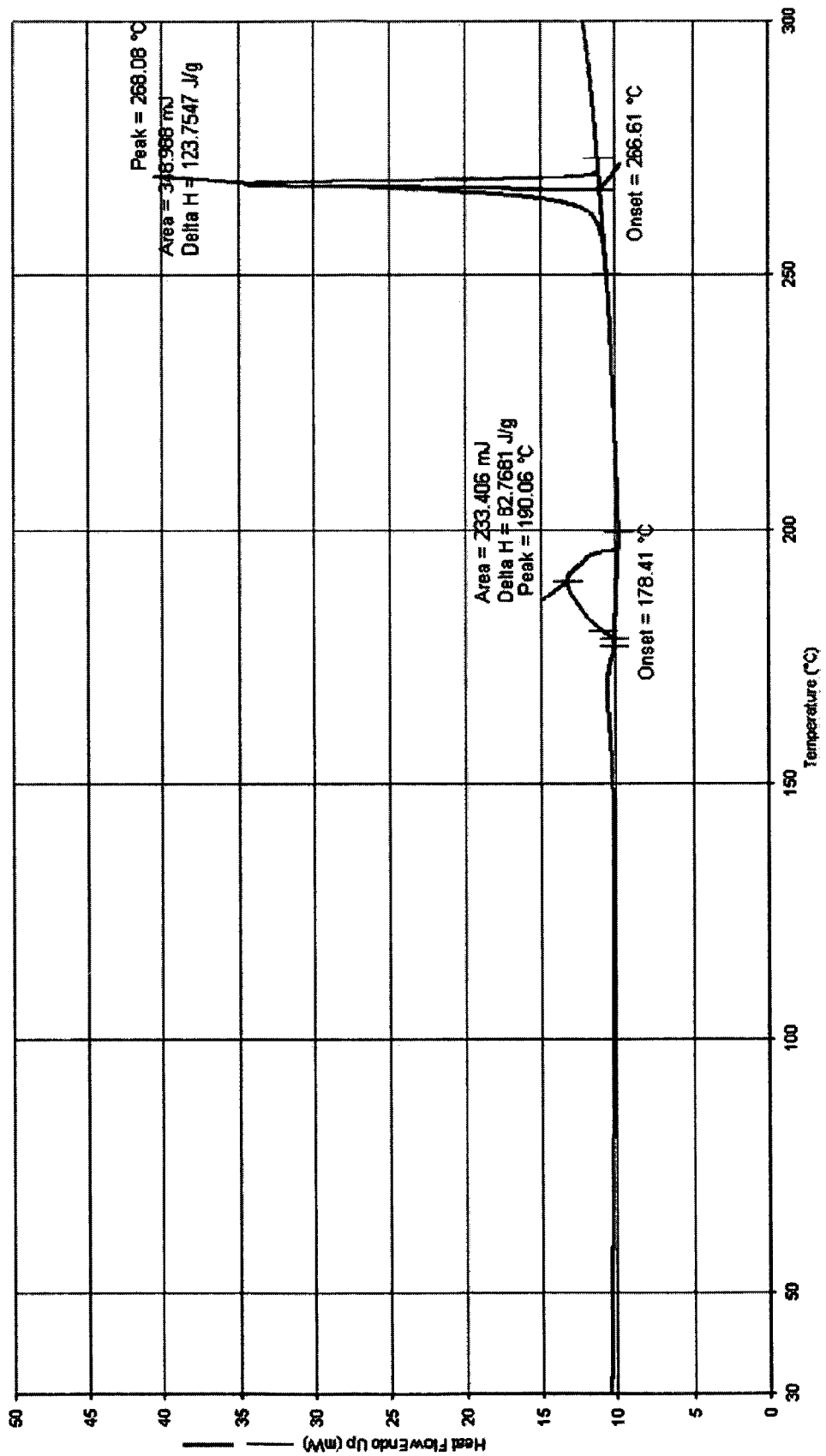
Figures 2, 34:
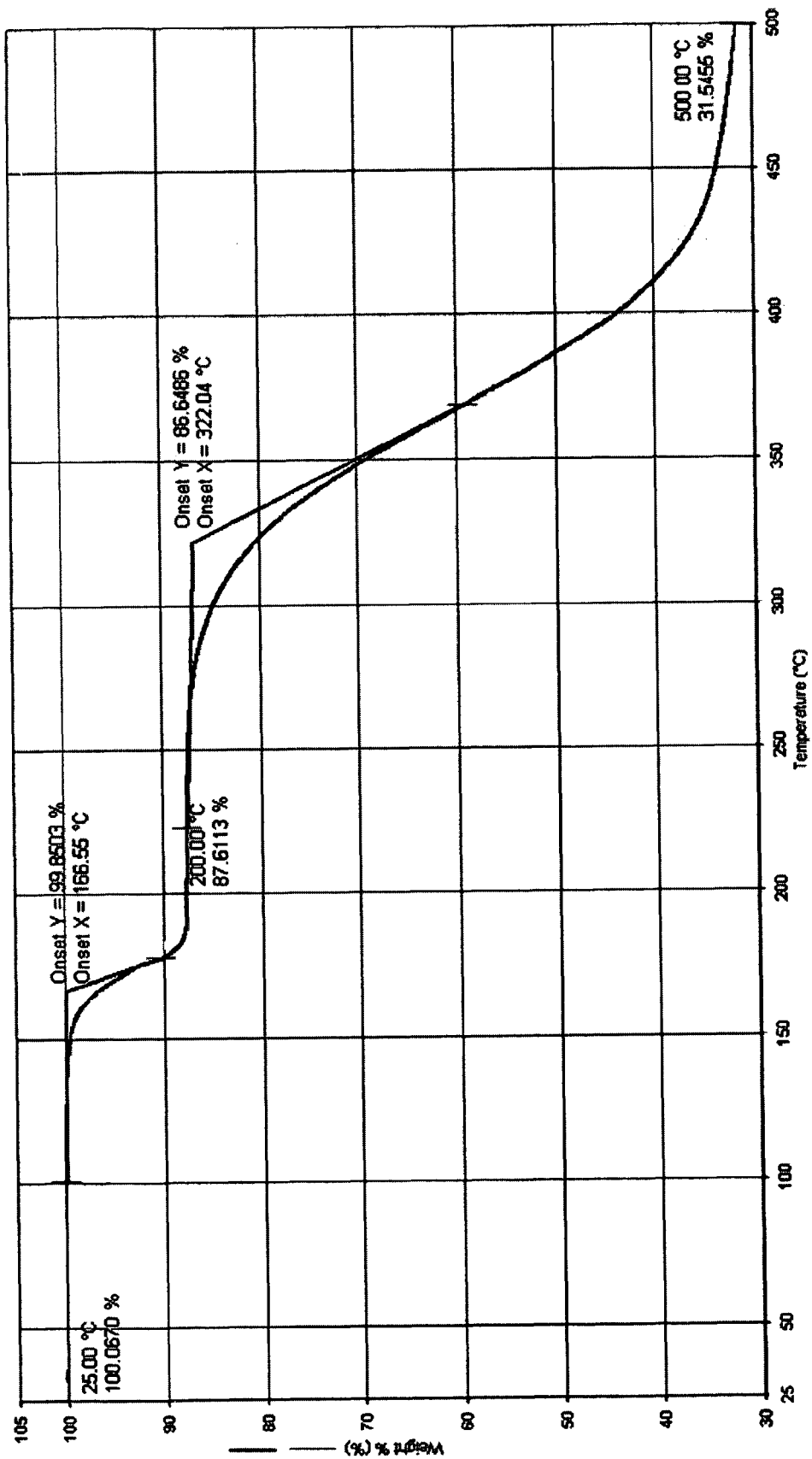
Figure 35:
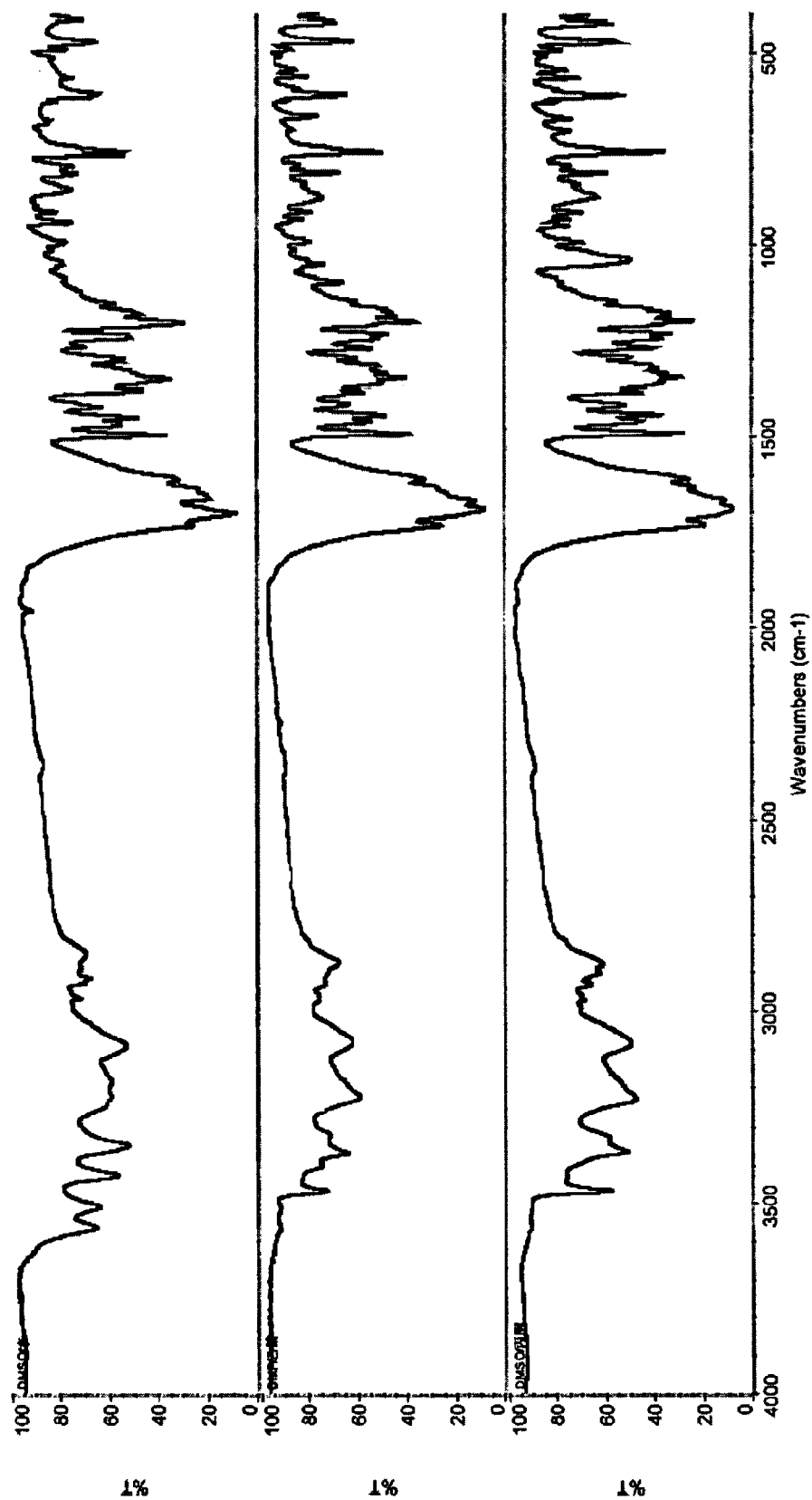
FIG. 35 is a comparative IR spectrum of the Polymorph I, II and III of 3-(4-amino-1-oxo-1,3-dihydro-2H-isoindole-2-yl)-piperidine-2,6-dione of this invention.

The raw material of Polymorph III of 3-(4-amino-1-oxo-1,3-dihydro-2H-isoindole-2-yl)-piperidine-2,6-dione was hermetically packed in plastic bags of polyethylene film and put in thermostatic and humidostatic incubator at 40±2° C. and 75±5% relative humidity for six months. Sample was tested at the end of the $1^{st}$, $2^{nd}$, $3^{rd}$ and $6^{th}$ month respectively and the results were contrasted with that of the zeroth month. Results were listed in Tab. 15. After accelerated test at 40° C. for six months, the X-ray powder diffraction pattern was shown in FIG. 33; DSC diagram was in FIG. 34-1; TGA diagram was in FIG. 34-2

TABLE 15

Short-Time Test (40° C. and 75% relative humidity)

| Time (months) | Appearance | Items Related substance (%) | Content (%) | Melting point (° C.) |
|---|---|---|---|---|
| 0 | off-white powder | 0.07 | 99.86 | 268.19 |
| 1 | off-white powder | 0.07 | 99.81 | / |
| 2 | off-white powder | 0.07 | 99.76 | / |
| 3 | off-white powder | 0.08 | 99.71 | / |
| 6 | off-white powder | 0.08 | 99.62 | 268.08 |

As is known from above results that in illumination test and high temperature (60° C.) test both appearance and content of Polymorph III of 3-(4-amino-1-oxo-1,3-dihydro-2H-isoindole-2-yl)-piperidine-2,6-dione obtained by this invention had few significant variation, which demonstrated the characteristic of stability; in high humidity test, both appearance and content of this product had few obvious change, but there is lower moisture absorption. In the observation test of long-term sample storage in high humidity, it was revealed by DSC scanning that a small amount of Polymorph III had transformed to Polymorph I.

In another embodiment of this invention, it provides pharmaceutical compositions comprising one or more of the Polymorph I, II and III of 3-(4-amino-1-oxo-1,3-dihydro-2H-isoindole-2-yl)-piperidine-2,6-dione and a pharmaceutical excipient; preferably, the pharmaceutical composition contains 500 mg of the polymorph of 3-(4-amino-1-oxo-1,3-dihydro-2H-isoindole-2-yl)-piperidine-2,6-dione; more preferably, it contains 5 mg, 10 mg, 15 mg or 25 mg of the polymorph of 3-(4-amino-1-oxo-1,3-dihydro-2H-isoindole-2-yl)-piperidine-2,6-dione. According to the teaching in the prior art of this field and referring to the patents cited by this invention, the pharmaceutical compositions of this invention could be prepared into all kinds of formulations and the proper pharmaceutical excipient could be selected. For instance, according to the diseases and objects, the pharmaceutical compositions of this invention could be delivered through such administration routes: oral, parenteral (e.g. intramuscular, intraperitoneal, intravenous, intracerebroventricular, intracisternal and subcutaneous injection or infusion), inhalation spray, nasal, vaginal, rectal, sublingual or local delivery; preferably, it is oral solid formulations, such as tablets, granules or capsules.

The pharmaceutical compositions of this invention containing the polymorph of 3-(4-amino-1-oxo-1,3-dihydro-2H-isoindole-2-yl)-piperidine-2,6-dione, could comprises other therapeutic components depending on the needs.

The pharmaceutical composition of this invention was administrated once or multiple times every day on the basis of daily dose, and the daily dose was about from 0.10 mg to 500 mg per day, more preferably from 1 mg to 250 mg per day. Alternatively, the pharmaceutical composition was administrated every two days on the dose of about from 0.10 mg to 150 mg per day or from 1 mg to 250 mg per day.

The diseases and syndromes which can be treated by 3-(4-amino-1-oxo-1,3-dihydro-2H-isoindole-2-yl)-piperidine-2,6-dione of the invention include, but not limited to: myeloproliferative disorder, osteomyelodysplasia syndrome, vasculogenesis, cancer, pain, macular degeneration, asbestosis, anaemia, nervous system disease, dyssomnia, dermatosis, pulmonary hypertension, immune deficiency disorder, parasitic diseases and central lesion etc., and the specific methods and doses could refer to Chinese Patents with the application numbers: 97180299.8, 98805614.3, 03825761.0, 03825567.7, 03813733.X, 03816899.5, 200610150484.3, 200380107531.0, 200710103924.4, 200380108093.X, 200380108398.0, 200480043341.1, 200480038171.8, 200480035556.9, 200480020445.0, 200480043535.1, 200480040004.7, 200480041252.3, 200480042208.4, 200580017546.7, 200580016344.0, 200580020628.7, 200580037220.0, 200580047364.4, 200580046371.2 and 200580047031.1.

The technical advantages of this invention include: although eight polymorphs of 3-(4-amino-1-oxo-1,3-dihydro-2H-isoindole-2-yl)-piperidine-2,6-dione and the preparation methods thereof has been reported in the patent documentation of CN 1871003A, the polymorphs of 3-(4-amino-1-oxo-1,3-dihydro-2H-isoindole-2-yl)-piperidine-2,6-dione prepared by the methods of the Patent CN 1871003A was verified that the polymorph A and the polymorph B had poor chemical stability in 0.1 mol/L diluted HCl solution and in the oxidation destroy experiment, and also the crystal transformation method described in the patent was unsuitable for industrial production.

By the existing technique in patent document CN 1871003A, the preparation method was that: 3-(4-amino-1-oxo-1,3-dihydro-2H-isoindole-2-yl)-piperidine-2,6-dione was added into water or organic solvent (e.g. hexane, toluene, acetone, acetonitrile, methanol and ethyl acetate) where it is practically insoluble for, after dissolved by heating, crystal was precipitated when being cooled or crystal transformed when being stirred for long time in slurrying system of solid-liquid diphase.

1. In U.S. Pat. No. 5,635,517 and Chinese Patent CN 101080400A, to prepare the target 3-(4-amino-1-oxo-1,3-dihydro-2H-isoindole-2-yl)-piperidine-2,6-dione, in the last step of chemical reaction, nitro was reduced by the method of Pd/C hydrogenation to yield the target compound, while the poor solubility of 3-(4-amino-1-oxo-1,3-dihydro-2H-isoindole-2-yl)-piperidine-2,6-dione in all kinds of reaction systems easily led to excess heavy metal in the products obtained by this method;

2. Because 3-(4-amino-1-oxo-1,3-dihydro-2H-isoindole-2-yl)-piperidine-2,6-dione was practically insoluble in water or the organic solvents mentioned above, a large quantity (more than 100 times) of solvent should be used even in the condition of heating. And it was not taken into consideration that harmful organic solvent sorted in or above Class II (e.g. toluene and acetonitrile etc.) should not be tried to use in synthesis of final products to minimize the negative effects of the residual organic solvent in products on human body;

3. By the method of crystal transformation described in the Patents of CN 1871003A and CN 101080400A, the appearance, color and luster of the products can not be improved, for example, from original light yellow to white or off-white;

4. The polymorph A and the polymorph B by the preparation methods of polymorph instructed in patent documents of CN 1871003A and CN 101080400A were easily destroyed to be decomposed within shorter time in 0.1 mol/L diluted HCl solution and in the oxidation destroy, which indicated their poor chemical stability.

5. Crystal transformation technique to prepare polymorphs in patents CN 1871003A and CN 101080400A, which was time-consuming with poor controllability, was unsuitable to industrial production.

In a word, the methods of polymorph preparation in patents CN 1871003A and CN 101080400A were unsuitable to industrial production.

However, this invention provided the methods suitable to industrially manufacturing polymorphs of 3-(4-amino-1-oxo-1,3-dihydro-2H-isoindole-2-yl)-piperidine-2,6-dione, which overcame the problems in existing technique.

In terms of the three new polymorphs of 3-(4-amino-1-oxo-1,3-dihydro-2H-isoindole-2-yl)-piperidine-2,6-dione in this invention, the crystallization conditions were in views of the insolubility of 3-(4-amino-1-oxo-1,3-dihydro-2H-isoindole-2-yl)-piperidine-2,6-dione in most solvents and difficult purification, and easy and feasible preparation methods were adopted:

1. the preparation technique of this invention was simple, quite easy for operation and convenient for industrial production, and the quality of the products was controllable and the polymorphs had good stability suitable to long-term storage;

2. by the methods of crystal transformation, strong-polar impurities were removed easily, resulting in dramatically reduction in related substance;

3. excess or over limit of heavy metal residue could be lowed significantly;

4. the appearance, color and luster of the products could be improved evidently from light yellow to white or off-white;

5. by comparison to the polymorph A described in patent CN1871003A, the Polymorph I of this invention had better stability in water, 0.1 mol/L HCl solution and in the oxidation destroy experiment, where it was substantially undecomposed or decomposition degree was obviously less than that of the polymorph A disclosed in patent CN1871003A. So the polymorph of this invention had more advantages for formulation;

6. by the methods of polymorph preparation in this invention, the amount of organic solvent used in crystal transformation could be reduced greatly, which led to reduced cost of products;

7. by the methods of this invention, water or organic solvents in Class III with low toxicity could be used selectively to prepare the polymorphs of this invention, avoiding the toxic effects on human body by the organic solvents such as toluene and methyl ethyl ketone etc. with high potential toxicity used in the patent CN1871003A.

Due to the above-mentioned advantages, this invention was beneficial to dramatic improvement in products quality and suitable to industrial production.

EXAMPLES

Preparation of the polymorphs of 3-(4-amino-1-oxo-1,3-dihydro-2H-isoindole-2-yl)-piperidine-2,6-dione

Example 1

Preparation of the Polymorph I of 3-(4-amino-1-oxo-1,3-dihydro-2H-isoindole-2-yl)-piperidine-2,6-dione 100 g of 3-(4-amino-1-oxo-1,3-dihydro-2H-isoindole-2-yl)-piperidine-2,6-dione was added into 400 mL DMF (or 300 mL DMSO), and dissolved by stirring and heating. Then 1600 mL water (or a mixed solvents system of 1000 mL water and 600 mL organic solvent, namely a dual or multiple mixture system consisting of water and organic solvent such as acetone, acetonitrile, ethyl acetate, dichloromethane, isopropanol, methanol, ethanol and etc. in which 3-(4-amino-1-oxo-1,3-dihydro-2H-isoindole-2-yl)-piperidine-2,6-dione was insoluble) was added and crystal precipitated when the mixture was stirred and cooled slowly. The solid was recovered and dried under vacuum to yield the Polymorph I of 3-(4-amino-1-oxo-1,3-dihydro-2H-isoindole-2-yl)-piperidine-2,6-dione.

DMF/water system: the product weighted 78 g and yield was 78%;

DMSO/water system: the product weighted 90 g and yield was 90%.

| | Contrasts | |
|---|---|---|
| Items | Index of raw material before transformation | Index of Polymorph I |
| Appearance | Yellow crystal powder | White to off-white crystal powder |
| Related substance | <0.31% | ≤0.05% |
| Heavy metal | ≥20 ppm, ≤50 ppm | ≤10 ppm |
| Water content | 0.097% | 3.613% |
| Melting point | 263.97° C. | 268.86° C. |

Example 2

Preparation of the Polymorph II of 3-(4-amino-1-oxo-1,3-dihydro-2H-isoindole-2-yl)-piperidine-2,6-dione 100 g of 3-(4-amino-1-oxo-1,3-dihydro-2H-isoindole-2-yl)-piperidine-2,6-dione was added into 400 mL anhydrous DMF and dissolved by stirring and heating; then 1800 mL anhydrous ethanol (or 1600-2000 mL sole or mixed solvents consisting of methanol, acetone, ethyl acetate, acetonitrile, dichloromethane and etc.) was added and crystal precipitated when the mixture was stirred and cooled slowly. The solid was recovered and dried under vacuum to yield the Polymorph II of 3-(4-amino-1-oxo-1,3-dihydro-2H-isoindole-2-yl)-piperidine-2,6-dione.

The product weighted 72 g and yield was 72%.

| | Contrasts | |
|---|---|---|
| Items | Index of raw material | Index of polymorph II |
| Appearance | Yellow crystal powder | White to off-white crystal powder |
| Related substance | <0.31% | ≤0.09% |
| Heavy metal | ≥20 ppm, ≤50 ppm | ≤10 ppm |
| Weight loss before 180° C. by TGA | 0.097% | 11.31% |
| Melting by DSC | 263.97° C. | 269.12° C. |

Example 3

Preparation of the Polymorph III of 3-(4-amino-1-oxo-1,3-dihydro-2H-isoindole-2-yl)-piperidine-2,6-dione 100 g of 3-(4-amino-1-oxo-1,3-dihydro-2H-isoindole-2-yl)-piperidine-2,6-dione was added into 300 mL anhydrous DMSO and dissolved by stirring and heating. Then 2000 mL anhydrous ethanol (alternative organic solvent such as methanol, acetone, ethyl acetate, acetonitrile, dichloromethane and etc. in which 3-(4-amino-1-oxo-1,3-dihydro-2H-isoindole-2-yl)-piperidine-2,6-dione was insoluble) was added and crystal precipitated when the mixture was stirred and cooled slowly. The solid was recovered and dried under vacuum to yield the polymorph III of 3-(4-amino-1-oxo-1,3-dihydro-2H-isoindole-2-yl)-piperidine-2,6-dione.

The product weighted 86 g and yield was 86%.

| | Contrasts | |
|---|---|---|
| Items | Index of raw material | Index of polymorph III |
| Appearance | Yellow crystal powder | White to off-white crystal powder |
| Related substance | <0.31% | ≤0.09% |
| Heavy metal | ≥20ppm, ≤50ppm | ≤10 ppm |
| Weight loss before 200° C. by TGA | 0.097% | 12.663% |
| melting point by DSC | 263.97° C. | 268.19° C. |

Example 4

Prescription and Preparation Method of Tablets:

According to the below-mentioned methods, several excipients and the above-mentioned Polymorph I or II or III of 3-(4-amino-1-oxo-1,3-dihydro-2H-isoindole-2-yl)-piperidine-2,6-dione or a mixture of the Polymorph I, II and III in any ratio were formulated into tablets containing 10 mg per tablet.

| | Amount (g/1000 tablets) | |
|---|---|---|
| Raw material and adjunct | Recipe 1 | Recipe 2 |
| 3-(4-amino-1-oxo-1,3-dihydro-2H-isoindole-2-yl)-piperidine-2,6-dione (I, II, III) | 10 g | 10 g |
| anhydrous lactose | 30 g | 15 g |

-continued

| Raw material and adjunct | Amount (g/1000 tablets) | |
|---|---|---|
| | Recipe 1 | Recipe 2 |
| starch | 30 g | 50 g |
| microcrystal cellulose | 20 g | 15 g |
| croscarmellose sodium | 9 g | / |
| sodium carboxylmethyl starch | / | 7 g |
| 10% PVP solution | 50 ml | 40 ml |
| magnesium stearate | 0.25 g | 0.15 g |

The manufacturing method of tablets containing the polymorph I or II or III of 3-(4-amino-1-oxo-1,3-dihydro-2H-isoindole-2-yl)-piperidine-2,6-dione or a mixture of the above-mentioned Polymorph I, II and III in any ratio was: the above-mentioned excipients were mixed homogeneously with the Polymorph I or II or III of 3-(4-amino-1-oxo-1,3-dihydro-2H-isoindole-2-yl)-piperidine-2,6-dione or a mixture of the above-mentioned Polymorph I, II and III in any ratio, and a proper amount of 10% PVP solution was added to form the damp mass, which was then granulated by screening. The moist granules were dried and size stabilized by screening, and then magnesium stearate and talcum powder were added to be homogeneous mixture, which was tableted at last.

Polymorph 1 Tablet—Accumulated Dissolution %

| Time | 1 # | 2 # | 3 # | 4 # | 5 # | average % | SD % | RSD % |
|---|---|---|---|---|---|---|---|---|
| 0 | 0 | 0 | 0 | 0 | 0 | 0 | 0 | 0 |
| 5 | 64.40 | 65.14 | 69.30 | 60.78 | 70.55 | 66.0 | 3.94 | 5.97 |
| 10 | 97.72 | 96.74 | 99.01 | 97.49 | 99.00 | 98.0 | 0.99 | 1.01 |
| 20 | 98.85 | 96.49 | 98.54 | 97.94 | 87.07 | 95.8 | 4.95 | 5.17 |
| 30 | 97.98 | 96.99 | 100.27 | 98.03 | 97.55 | 98.2 | 1.25 | 1.27 |
| 45 | 96.76 | 95.27 | 97.51 | 96.59 | 96.83 | 96.6 | 0.82 | 0.84 |
| 60 | 97.08 | 94.62 | 96.16 | 96.59 | 96.73 | 96.2 | 0.96 | 1.00 |

Example 5

Prescription and Preparation Method of Capsules:

According to the below-mentioned methods, several excipients and the Polymorph I or II or III of 3-(4-amino-1-oxo-1,3-dihydro-2H-isoindole-2-yl)-piperidine-2,6-dione or a mixture of the above-mentioned polymorphs in any ratio were formulated into capsules containing 10 mg per capsule.

| Raw material and adjunct | Amount (g/1000 capsules) | | |
|---|---|---|---|
| | Recipe 1 | Recipe 2 | Recipe 3 |
| 3-(4-amino-1-oxo-1,3-dihydro-2H-isoindole-2-yl)-piperidine-2,6-dione (I, II, III) | 10 g | 10 g | 10 g |
| anhydrous lactose | 30 g | 50 g | / |
| starch | 30 g | / | 60 g |
| microcrystal cellulose | 30 g | 40 g | 25 g |
| croscarmellose sodium | / | 6.5 g | 7.5 |
| sodium carboxylmethyl starch | 8 g | / | / |
| 10% PVP solution | 45 ml | 55 ml | 35 ml |
| magnesium stearate | 0.3 g | 0.2 g | 0.25 g |

The manufacturing method of capsules containing the Polymorph I or II or III of 3-(4-amino-1-oxo-1,3-dihydro-2H-isoindole-2-yl)-piperidine-2,6-dione or a mixture of the above-mentioned Polymorph I, II and III in any ratio was: the above-mentioned excipients were mixed homogeneously with the Polymorph I or II or III of 3-(4-amino-1-oxo-1,3-dihydro-2H-isoindole-2-yl)-piperidine-2,6-dione or a mixture of the above-mentioned three polymorphs in any ratio and a proper amount of 10% PVP solution was added to form the moist granules, which were dried and size stabilized by screening. Then magnesium stearate was added to be homogeneous mixture, which was capsuled. Alternatively, without granulation the homogeneous mixture of 3-(4-amino-1-oxo-1,3-dihydro-2H-isoindole-2-yl)-piperidine-2,6-dione and above-mentioned excipients was screened and capsuled directly.

Polymorph I Capsule—Accumulated Dissolution %

| Time | 1 # | 2 # | 3 # | 4 # | 5 # | average % | SD % | RSD % |
|---|---|---|---|---|---|---|---|---|
| 0 | 0 | 0 | 0 | 0 | 0 | 0 | 0 | 0 |
| 5 | 60.86 | 59.90 | 35.00 | 50.84 | 22.77 | 45.9 | 16.57 | 36.12 |
| 10 | 91.04 | 93.30 | 85.66 | 91.23 | 83.92 | 89.0 | 4.02 | 4.51 |
| 20 | 94.08 | 96.78 | 92.84 | 95.18 | 93.02 | 94.4 | 1.64 | 1.73 |
| 30 | 95.38 | 96.14 | 93.62 | 95.42 | 93.56 | 94.8 | 1.17 | 1.23 |
| 45 | 93.02 | 95.66 | 93.91 | 94.11 | 93.00 | 93.9 | 1.09 | 1.16 |
| 60 | 94.63 | 94.10 | 93.38 | 93.83 | 92.08 | 93.6 | 0.97 | 1.03 |

Comparative Test

The methods of destruction experiment of the Polymorph I of this invention (hereinafter referred to as "Polymorph I") contrasting with the Polymorph A and B of 3-(4-amino-1-oxo-1,3-dihydro-2H-isoindole-2-yl)-piperidine-2,6-dione prepared by the method in CN 1871003A (hereinafter referred to as "Polymorph A" and "polymorph B") and results of stability are followed:

Table 16: results of stability of Polymorph A, Polymorph B and Polymorph I in destruction test

| Conditions Results | Polymorph kind | | |
|---|---|---|---|
| | Polymorph A | Polymorph B | Polymorph I |
| Major impurities in raw materials before destruction | Total impurities: 0.06% tR5.948  0.01% tR6.855  0.01% tR11.165  0.04% | Total impurities: 0.07% tR5.921  0.01% tR6.847  0.01% tR11.165  0.05% | Total impurities: 0.04% tR5.872  0.01% tR10.961  0.03% |
| Major impurities generated by oxidation destruction | Total impurities: 0.82% tR5.655  0.39% tR10.401  0.08% tR32.318  0.08% tR35.098  0.14% | Total impurities: 0.89% tR5.649  0.36% tR10.397  0.11% tR32.302  0.10% tR35.063  0.13% | Total impurities: 0.16% tR5.660  0.09% tR10.372  0.03% tR32.279  0.01% tR35.082  0.02% |
| Major impurities generated by 0.1 mol/L | Total impurities: 1.13% | Total impurities: 1.22% | Total impurities: 0.62% |

-continued

| Conditions Results | Polymorph kind | | | | | |
|---|---|---|---|---|---|---|
| | Polymorph A | | Polymorph B | | Polymorph I | |
| acid destruction for 1 hour | tR4.722 | 0.33% | tR4.717 | 0.33% | tR4.737 | 0.20% |
| | tR7.378 | 0.72% | tR7.367 | 0.72% | tR7.381 | 0.41% |
| | tR11.100 | 0.04% | tR11.096 | 0.04% | tR11.067 | 0.01% |

Procedure:

Acid destruction: 50 mg of sample weighted accurately was added into measuring flask of 100 mL, and 10 mL 0.1 mol/L HCl solution was added. After standing at room temperature for 1 hour, an equal amount of 0.1 mol/L NaOH solution was added for neutralization. Then the mixture was diluted with mobile phase to scale and shook to be homogeneous, and determined by HPLC.

Oxidation destruction: 50 mg of sample weighted accurately was added into measuring flask of 100 mL, and 10 mL 30% $H_2O_2$ was added. After standing at room temperature for 2 hour, the mixture was diluted with mobile phase to scale and shook to be homogeneous, and determined by HPLC.

Related Substances Determination

HPLC conditions and system applicability: octadecylsilane bonded silica as the filler; 0.01 mol/L of potassium dihydrogen phosphate (adjusted to pH 3.5 by phosphoric acid)-methanol-acetonitrile (80:15:5) as the mobile phase; detection wavelength was 240 nm; the number of theoretical plates should be not less than 2000, calculated according to the peak of lenalidomide. The resolution of the peak of 3-(4-amino-1-oxo-1,3-dihydro-2H-isoindole-2-yl)-piperidine-2, 6-dione from the peaks of adjacent impurities should meet requirements.

Determination method: sample was dissolved in mobile phase to be the solution containing 0.5 mg per 1 mL. 20 μL of such solution was injected into liquid chromatograph and chromatogram was recorded until fourfold the retention time of major component peak. If there were impurities peaks in the chromatogram of sample solution, total impurities and sole impurity were calculated by normalization method on the basis of peak area.

As is revealed in the experimental results, by comparison with Polymorph A and Polymorph B, Polymorph I of this invention had better stability whether in the acid condition or in the oxidating condition, indicating that Polymorph I was more suitable to be made into pharmaceuticals.

The invention claimed is:

1. A Crystalline Form I of 3-(4-amino-1-oxo-1,3-dihydro-2H-isoindole-2-yl)-piperidine-2,6-dione hemihydrate, characterized by diffraction peaks at in its X-ray powder diffraction pattern using Cu—Kα radiation as follows:

| Peak Number | 2θ | Flex Width | d-Value | Intensity | L/LO |
|---|---|---|---|---|---|
| 1 | 11.940 | 0.212 | 7.4060 | 17891 | 84 |
| 2 | 13.020 | 0.235 | 6.7940 | 5996 | 28 |
| 3 | 13.780 | 0.188 | 6.4210 | 6550 | 31 |
| 6 | 15.620 | 0.235 | 5.6685 | 9017 | 42 |

-continued

| Peak Number | 2θ | Flex Width | d-Value | Intensity | L/LO |
|---|---|---|---|---|---|
| 9 | 17.960 | 0.259 | 4.9349 | 5895 | 28 |
| 10 | 19.080 | 0.235 | 4.6476 | 8374 | 39 |
| 11 | 19.480 | 0.235 | 4.5531 | 6273 | 30 |
| 12 | 20.580 | 0.235 | 4.3121 | 6162 | 29 |
| 15 | 21.980 | 0.235 | 4.0405 | 21530 | 100 |
| 16 | 22.520 | 0.259 | 3.9449 | 13747 | 64 |
| 18 | 23.760 | 0.259 | 3.7417 | 15053 | 70 |
| 19 | 24.400 | 0.212 | 3.6450 | 5016 | 24 |
| 21 | 26.440 | 0.282 | 3.3682 | 15819 | 74 |
| 22 | 27.520 | 0.353 | 3.2384 | 11455 | 54 |
| 23 | 29.060 | 0.306 | 3.0702 | 11190 | 52 |
| 24 | 30.980 | 0.306 | 2.8842 | 6238 | 29 |
| 25 | 32.000 | 0.376 | 2.7945 | 4934 | 23 |
| 26 | 33.040 | 0.306 | 2.7089 | 5313 | 25 |
| 28 | 34.440 | 0.259 | 2.6019 | 5469 | 26 | and having an endothermic peak at about 164.68° C. and maximal endothermic transformation at about 268.86° C. in its DSC diagram.

2. The Crystalline Form I according to claim 1, characterized by absorption peaks at about 3561.4 cm$^{-1}$, 3507.4 cm$^{-1}$, 3424.2 cm$^{-1}$, 3345.8 cm$^{-1}$, 3091.0 cm$^{-1}$, 2912.5 cm$^{-1}$, 1697.8 cm$^{-1}$, 1658.8 cm$^{-1}$, 1610.0 cm$^{-1}$, 1494.3 cm$^{-1}$, 1349.5 cm$^{-1}$, 1201.4 cm$^{-1}$ in its infrared spectrum in KBr disc.

3. The Crystalline Form I according to claim 1, which X-ray powder diffraction pattern is as shown in FIG. 1.

4. A pharmaceutical compositions comprising the Crystalline Form I of 3-(4-amino-1-oxo-1,3-dihydro-2H-isoindole-2-yl)-piperidine-2,6-dione according to claim 1.

5. A preparation method of the Crystalline Form I according to claim 1 includes the following steps:
 (1) 3-(4-amino-1-oxo-1,3-dihydro-2H-isoindole-2-yl)-piperidine-2,6-dione is added into dimethylformamide, and dissolved by stirring and heating;
 (2) a mixed solvent system of purified water and organic solvent is added, wherein, the mentioned organic solvent is acetone, acetonitrile, ethyl acetate, dichloromethane, isopropanol, methanol, or ethanol;
 (3) solid is precipitated by stirring and cooling down slowly; and
 (4) recover the solid and dry it under vacuum.

6. The preparation method of claim 5, wherein a volume to weight ratio of dimethylformamide to 3-(4-amino-1-oxo-1, 3-dihydro-2H-isoindole-2-yl)-piperidine-2,6-dione is over 1:1, and a volume ratio of the mixed solvent system to dimethylformamide is over 1:1.

* * * * *